US009186487B2

(12) United States Patent
Dubrul et al.

(10) Patent No.: US 9,186,487 B2
(45) Date of Patent: Nov. 17, 2015

(54) MEDICAL DEVICE AND METHOD

(71) Applicant: Genesis Technologies LLC, Grand Junction, CO (US)

(72) Inventors: William R. Dubrul, Jefferson City, MT (US); Brent D. Seybold, Santa Clara, CA (US); Mark L. Mathis, Fremont, CA (US); Philip M. Leopold, North Barrington, IL (US); Richard E. Fulton, Grand Junction, CO (US)

(73) Assignee: GENESIS TECHNOLOGIES LLC, Grand Junction, CO (US)

( * ) Notice: Subject to any disclaimer, the term of this patent is extended or adjusted under 35 U.S.C. 154(b) by 0 days.

(21) Appl. No.: 13/725,871

(22) Filed: Dec. 21, 2012

(65) Prior Publication Data
US 2013/0110152 A1 May 2, 2013

Related U.S. Application Data

(63) Continuation of application No. 12/477,371, filed on Jun. 3, 2009, which is a continuation-in-part of application No. 10/824,779, filed on Apr. 15, 2004, now abandoned.

(51) Int. Cl.
*A61B 17/22* (2006.01)
*A61B 17/24* (2006.01)
(Continued)

(52) U.S. Cl.
CPC .......... *A61M 25/104* (2013.01); *A61B 10/0266* (2013.01); *A61B 17/11* (2013.01);
(Continued)

(58) Field of Classification Search
CPC ..... A61F 2/01; A61F 2002/011; A61F 2/013; A61F 2/95; A61M 25/0119; A61M 25/0074; A61B 17/12022; A61B 17/12109; A61B 17/22; A61B 17/22032; A61B 17/221; A61B 2017/22079
USPC ........ 606/200, 113–114, 127–128, 1.11, 108, 606/198
See application file for complete search history.

(56) References Cited

U.S. PATENT DOCUMENTS 2,230,226 A 2/1941 Auzin
2,259,488 A 10/1941 Raiche
(Continued)

FOREIGN PATENT DOCUMENTS

EP 0 983 749 A2 3/2000
FR 2 312 264 12/1976
(Continued)

OTHER PUBLICATIONS

Office Action for U.S. Appl. No. 10/765,564 mailed on Oct. 9, 2007.
(Continued)

*Primary Examiner* — Darwin Erezo
*Assistant Examiner* — Lindsey Bachman
(74) *Attorney, Agent, or Firm* — Wilson Sonsini Goodrich & Rosati

(57) ABSTRACT

A vessel-occluding medical device for the use in diagnosis and/or treatment of cardiovascular disease in the human body includes an outer tube, an inner tube slidably housed within the outer tube, and a tubular sleeve comprising a generally U-shaped, direction reversing region, which moves along the length of the tubular sleeve, to assume radially contracted and radially expanded state as the inner and outer tubes move between the first and second positions. When the tubular sleeve is in the radially expanded state, the inner portion of the tubular sleeve has a funnel-shaped surface and a longitudinally-extending opening to permit material to pass therethrough for receipt of material into the inner tube.

2 Claims, 30 Drawing Sheets

(51) Int. Cl.

| | |
|---|---|
| *A61B 17/26* | (2006.01) |
| *A61M 25/10* | (2013.01) |
| *A61B 17/11* | (2006.01) |
| *A61B 17/12* | (2006.01) |
| *A61B 17/221* | (2006.01) |
| *A61B 17/3205* | (2006.01) |
| *A61M 25/01* | (2006.01) |
| *A61B 6/00* | (2006.01) |
| *A61B 10/02* | (2006.01) |
| *A61B 17/34* | (2006.01) |
| *A61B 18/14* | (2006.01) |
| *A61B 19/00* | (2006.01) |
| *A61B 17/00* | (2006.01) |

(52) U.S. Cl.
CPC ..... *A61B17/12022* (2013.01); *A61B 17/12109* (2013.01); *A61B 17/12113* (2013.01); *A61B 17/12122* (2013.01); *A61B 17/12172* (2013.01); *A61B 17/221* (2013.01); *A61B 17/32056* (2013.01); *A61B 19/54* (2013.01); *A61B 6/502* (2013.01); *A61B 10/02* (2013.01); *A61B 17/22004* (2013.01); *A61B 17/3421* (2013.01); *A61B 18/14* (2013.01); *A61B 19/38* (2013.01); *A61B 2017/00287* (2013.01); *A61B 2017/00955* (2013.01); *A61B 2017/1107* (2013.01); *A61B 2017/1135* (2013.01); *A61B 2017/1205* (2013.01); *A61B 2017/2212* (2013.01); *A61B 2017/2215* (2013.01); *A61B 2017/22034* (2013.01); *A61B 2017/22067* (2013.01); *A61B 2017/22079* (2013.01); *A61B 2018/1407* (2013.01); *A61B 2019/5404* (2013.01); *A61B 2019/5408* (2013.01); *A61B 2019/5462* (2013.01); *A61M 25/0119* (2013.01)

(56) References Cited

U.S. PATENT DOCUMENTS

| | | | |
|---|---|---|---|
| 3,050,066 A | 8/1962 | Koehn | |
| 3,831,587 A | 8/1974 | Boyd | |
| 3,978,863 A | 9/1976 | Fettel et al. | |
| 3,996,938 A | 12/1976 | Clark, III | |
| 4,030,503 A | 6/1977 | Clark, III | |
| 4,372,293 A | 2/1983 | Vijil-Rosales | |
| 4,401,124 A | 8/1983 | Guess et al. | |
| 4,425,908 A | 1/1984 | Simon | |
| 4,445,892 A | 5/1984 | Hussein et al. | |
| 4,573,966 A | 3/1986 | Weikl et al. | |
| 4,581,017 A | 4/1986 | Sahota | |
| 4,582,061 A | 4/1986 | Fry | |
| 4,606,347 A | 8/1986 | Fogarty et al. | |
| 4,608,965 A | 9/1986 | Anspach et al. | |
| 4,611,594 A | 9/1986 | Grayhack et al. | |
| 4,650,466 A | 3/1987 | Luther | |
| 4,696,304 A | 9/1987 | Chin | |
| 4,794,925 A | 1/1989 | Mori | |
| 4,794,928 A | 1/1989 | Kletschka | |
| 4,799,495 A | 1/1989 | Hawkins et al. | |
| 4,820,270 A | 4/1989 | Hardcastle et al. | |
| 4,858,810 A | 8/1989 | Intlekofer | |
| 4,869,259 A | 9/1989 | Elkins | |
| 4,895,560 A | 1/1990 | Papantonakos | |
| 4,921,478 A | 5/1990 | Solano et al. | |
| 4,921,484 A | 5/1990 | Hillstead | |
| 4,946,440 A | 8/1990 | Hall | |
| 4,977,897 A | 12/1990 | Hurwitz | |
| 5,011,488 A | 4/1991 | Ginsburg | |
| 5,048,530 A | 9/1991 | Hurwitz | |
| 5,059,166 A | 10/1991 | Fischell et al. | |
| 5,081,997 A | 1/1992 | Bosley et al. | |
| 5,092,839 A | 3/1992 | Kipperman | |
| 5,100,425 A | 3/1992 | Fischell et al. | |
| 5,102,415 A * | 4/1992 | Guenther et al. | 606/159 |
| 5,108,420 A | 4/1992 | Marks | |
| 5,112,347 A | 5/1992 | Taheri | |
| 5,135,484 A | 8/1992 | Wright | |
| 5,171,305 A | 12/1992 | Schickling et al. | |
| 5,176,659 A | 1/1993 | Mancini | |
| 5,183,463 A | 2/1993 | Debbas | |
| 5,192,290 A | 3/1993 | Hilal | |
| 5,209,727 A | 5/1993 | Radisch | |
| 5,213,569 A | 5/1993 | Davis | |
| 5,221,269 A | 6/1993 | Miller et al. | |
| 5,250,060 A | 10/1993 | Carbo et al. | |
| 5,275,611 A | 1/1994 | Behl | |
| 5,312,360 A | 5/1994 | Behl | |
| 5,328,471 A | 7/1994 | Slepian | |
| 5,329,942 A | 7/1994 | Gunther et al. | |
| 5,336,205 A | 8/1994 | Zenzen et al. | |
| 5,342,306 A | 8/1994 | Don Michael | |
| 5,370,660 A | 12/1994 | Weinstein et al. | |
| 5,380,273 A | 1/1995 | Dubrul et al. | |
| 5,380,284 A | 1/1995 | Don Michael | |
| 5,382,259 A | 1/1995 | Phelps et al. | |
| 5,383,466 A | 1/1995 | Partika | |
| 5,383,897 A | 1/1995 | Wholey | |
| 5,419,774 A | 5/1995 | Willard et al. | |
| 5,431,676 A | 7/1995 | Dubrul et al. | |
| 5,437,631 A | 8/1995 | Janzen | |
| 5,441,485 A | 8/1995 | Peters | |
| 5,443,454 A | 8/1995 | Tanabe et al. | |
| 5,456,667 A | 10/1995 | Ham | |
| 5,483,976 A | 1/1996 | McLaughlin et al. | |
| 5,490,521 A | 2/1996 | Davis et al. | |
| 5,496,275 A | 3/1996 | Sirhan et al. | |
| 5,497,782 A | 3/1996 | Fugoso | |
| 5,498,236 A | 3/1996 | Dubrul et al. | |
| 5,518,498 A | 5/1996 | Lindenberg et al. | |
| 5,540,658 A | 7/1996 | Evans et al. | |
| 5,549,626 A | 8/1996 | Miller et al. | |
| 5,571,135 A | 11/1996 | Fraser et al. | |
| 5,591,204 A | 1/1997 | Janzen et al. | |
| 5,606,979 A | 3/1997 | Hodgson | |
| 5,611,345 A | 3/1997 | Hibbeln | |
| 5,626,614 A | 5/1997 | Hart | |
| 5,643,282 A | 7/1997 | Kieturakis | |
| 5,653,684 A | 8/1997 | Laptewicz et al. | |
| 5,653,689 A | 8/1997 | Buelna et al. | |
| 5,662,671 A | 9/1997 | Barbut et al. | |
| 5,662,703 A * | 9/1997 | Yurek et al. | 623/1.12 |
| 5,683,411 A | 11/1997 | Kavteladze et al. | |
| 5,683,451 A | 11/1997 | Lenker et al. | |
| 5,709,697 A | 1/1998 | Ratcliff et al. | |
| 5,709,704 A | 1/1998 | Nott et al. | |
| 5,713,848 A | 2/1998 | Dubrul et al. | |
| 5,730,733 A | 3/1998 | Mortier et al. | |
| 5,733,294 A | 3/1998 | Forber | |
| 5,738,652 A | 4/1998 | Boyd et al. | |
| 5,749,883 A | 5/1998 | Halpern | |
| 5,766,135 A | 6/1998 | Terwilliger | |
| 5,766,203 A | 6/1998 | Imran et al. | |
| 5,769,795 A | 6/1998 | Terwilliger | |
| 5,769,871 A | 6/1998 | Mers Kelly et al. | |
| 5,779,672 A | 7/1998 | Dormandy | |
| 5,795,308 A | 8/1998 | Russin | |
| 5,797,960 A | 8/1998 | Stevens et al. | |
| 5,814,064 A | 9/1998 | Daniel et al. | |
| 5,827,324 A | 10/1998 | Cassell et al. | |
| 5,833,650 A | 11/1998 | Imran | |
| 5,843,022 A | 12/1998 | Willard et al. | |
| 5,846,251 A | 12/1998 | Hart | |
| 5,851,210 A | 12/1998 | Torossian | |
| 5,853,422 A | 12/1998 | Huebsch et al. | |
| 5,868,708 A | 2/1999 | Hart et al. | |
| 5,897,567 A | 4/1999 | Ressemann et al. | |
| 5,908,435 A | 6/1999 | Samuels | |
| 5,928,260 A | 7/1999 | Chin et al. | |
| 5,935,139 A | 8/1999 | Bates | |
| 5,997,503 A | 12/1999 | Willis et al. | |
| 6,001,118 A | 12/1999 | Daniel et al. | |
| 6,027,520 A | 2/2000 | Tsugita et al. | |

(56) References Cited

U.S. PATENT DOCUMENTS

| | | | |
|---|---|---|---|
| 6,053,876 | A | 4/2000 | Fisher |
| 6,053,900 | A * | 4/2000 | Brown et al. .................. 604/500 |
| 6,086,605 | A | 7/2000 | Barbut et al. |
| 6,096,053 | A | 8/2000 | Bates |
| 6,156,005 | A | 12/2000 | Theron |
| 6,161,034 | A | 12/2000 | Burbank et al. |
| 6,206,868 | B1 | 3/2001 | Parodi |
| 6,221,006 | B1 | 4/2001 | Dubrul et al. |
| 6,221,086 | B1 | 4/2001 | Forber |
| 6,231,544 | B1 | 5/2001 | Tsugita et al. |
| 6,238,412 | B1 | 5/2001 | Dubrul et al. |
| 6,258,115 | B1 | 7/2001 | Dubrul |
| 6,277,083 | B1 | 8/2001 | Eggers et al. |
| 6,287,271 | B1 | 9/2001 | Dubrul et al. |
| 6,356,782 | B1 | 3/2002 | Sirimanne et al. |
| 6,361,545 | B1 | 3/2002 | Macoviak et al. |
| 6,375,634 | B1 | 4/2002 | Carroll |
| 6,413,235 | B1 | 7/2002 | Parodi |
| 6,450,989 | B2 | 9/2002 | Dubrul et al. |
| 6,540,768 | B1 | 4/2003 | Diaz et al. |
| 6,544,278 | B1 * | 4/2003 | Vrba et al. .................... 606/198 |
| 6,602,204 | B2 | 8/2003 | Dubrul et al. |
| 6,605,102 | B1 | 8/2003 | Mazzocchi et al. |
| 6,635,068 | B1 | 10/2003 | Dubrul et al. |
| 6,699,260 | B2 | 3/2004 | Dubrul et al. |
| 6,740,094 | B2 | 5/2004 | Maitland et al. |
| 6,994,677 | B1 | 2/2006 | Buehlmann et al. |
| 7,201,770 | B2 | 4/2007 | Johnson et al. |
| 7,220,269 | B1 | 5/2007 | Ansel et al. |
| 7,232,432 | B2 | 6/2007 | Fulton et al. |
| 7,422,579 | B2 | 9/2008 | Wahr et al. |
| 2002/0007130 | A1 | 1/2002 | Burbank et al. |
| 2002/0016555 | A1 | 2/2002 | Ritchart et al. |
| 2002/0019640 | A1 | 2/2002 | McGuckin, Jr. |
| 2002/0022859 | A1 | 2/2002 | Hogendijk |
| 2002/0026201 | A1 | 2/2002 | Foerster et al. |
| 2002/0045916 | A1 | 4/2002 | Gray et al. |
| 2002/0095169 | A1 | 7/2002 | Maitland et al. |
| 2002/0165574 | A1 | 11/2002 | Ressemann et al. |
| 2002/0165598 | A1 | 11/2002 | Wahr et al. |
| 2003/0023204 | A1 | 1/2003 | Vo et al. |
| 2003/0114879 | A1 * | 6/2003 | Euteneuer et al. ............ 606/200 |
| 2004/0153117 | A1 | 8/2004 | Clubb et al. |
| 2004/0181237 | A1 * | 9/2004 | Forde et al. .................... 606/108 |
| 2004/0199202 | A1 | 10/2004 | Dubrul et al. |
| 2004/0260332 | A1 | 12/2004 | Dubrul et al. |
| 2005/0059993 | A1 * | 3/2005 | Ramzipoor et al. .......... 606/200 |
| 2005/0187570 | A1 | 8/2005 | Nguyen |
| 2007/0126161 | A1 | 6/2007 | Gray et al. |
| 2007/0142858 | A1 | 6/2007 | Bates |
| 2007/0233175 | A1 | 10/2007 | Zaver et al. |
| 2010/0030256 | A1 | 2/2010 | Dubrul et al. |
| 2010/0114113 | A1 | 5/2010 | Dubrul et al. |
| 2014/0188127 | A1 | 7/2014 | Dubrul et al. |
| 2014/0236219 | A1 | 8/2014 | Dubrul et al. |

FOREIGN PATENT DOCUMENTS

| | | |
|---|---|---|
| FR | 2312264 A1 | 12/1976 |
| FR | 2 380 018 | 9/1978 |
| FR | 2380018 A1 | 9/1978 |
| GB | 2020557 | 11/1979 |
| GB | 2020557 A | 11/1979 |
| WO | 80/01343 | 6/1980 |
| WO | 8001343 A1 | 6/1980 |
| WO | 80/01353 | 7/1980 |
| WO | 8001353 A1 | 7/1980 |
| WO | 94/24946 | 11/1994 |
| WO | 9424946 A1 | 11/1994 |
| WO | 96/01591 | 1/1996 |
| WO | 9601591 A1 | 1/1996 |
| WO | 9923952 | 5/1999 |
| WO | 9923952 A1 | 5/1999 |
| WO | WO 99/44506 | 9/1999 |
| WO | WO 00/12009 | 3/2000 |
| WO | WO 00/12010 | 3/2000 |
| WO | 02/087677 | 11/2002 |
| WO | 02087677 A2 | 11/2002 |

OTHER PUBLICATIONS

Velocimed, "Proxis, Embolic Protection System", http://www.velocimed.com/proxis.htm (visited Jun. 2, 2004), 4pp., (2003).
Supplementary European Search Report mailed Jul. 23, 2008—EP Application No. 04759873.5-2310: filed Apr. 15, 2004.
Office Action for U.S. Appl. No. 10/747,813 Mailed on Jan. 10, 2008.
Office Action for U.S. Appl. No. 10/747,813 Mailed on Jul. 26, 2007.
Office Action for U.S. Appl. No. 10/747,813 Mailed on Sep. 19, 2007.
Office Action for U.S. Appl. No. 10/765,564 Mailed Oct. 9, 2007.
Office Action for U.S. Appl. No. 10/866,980 Mailed on Oct. 5, 2007.
Velocimed, "Proxis, Embolic Protection System", http://www.velocimed.com/proxis.htm (visited Jun. 2, 2004). 4pp., (2003).
Office Action for U.S. Appl. No. 10/747,813 mailed on Jan. 10, 2008. (6 pages).
Supplementary European Search Report mailed Jul. 23, 2008 for EP Application No. 04759873.5, filed Apr. 15, 2004. (4 pages).
Velocimed, "Proxis, Embolic Protection System", http://www.velocimed.com/proxis.htm (visited May 2, 2004), (2003). (4 pages).
Final Office Action for U.S. Appl. No. 12/477,371 Mailed on Jun. 29, 2012.
Final Office Action for U.S. Appl. No. 12/477,371 Mailed on May 20, 2014.
Office Action for U.S. Appl. No. 12/477,371 Mailed on Nov. 8, 2011.
Office Action for U.S. Appl. No. 12/477,371 Mailed on Sep. 27, 2013.
U.S. Appl. No. 14/554,348, filed Nov. 26, 2014, Fulton.
Office action dated Nov. 20, 2014 for U.S. Appl. No. 14/201,371.
U.S. Appl. No. 14/645,830, filed Mar. 12, 2015, Fulton.

* cited by examiner

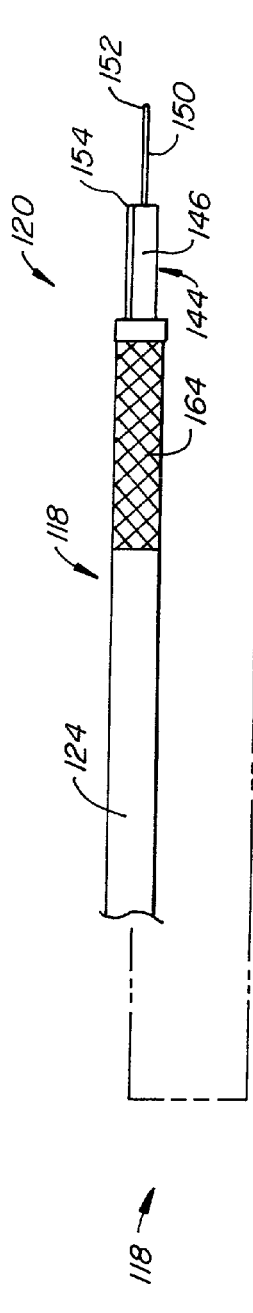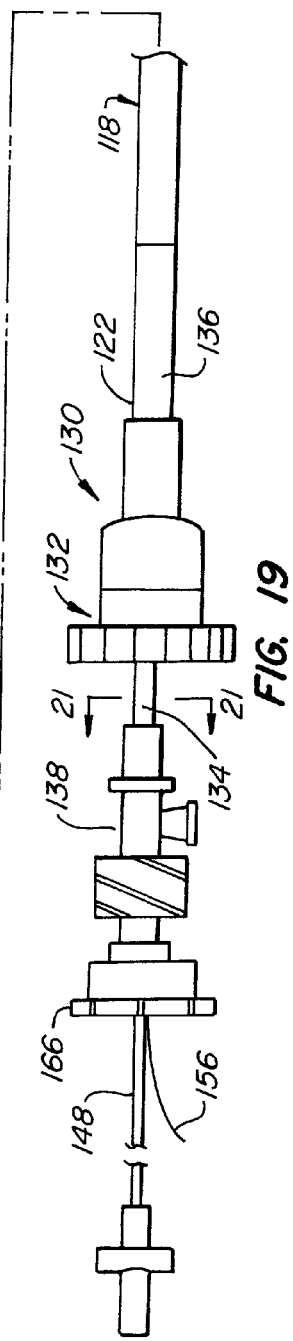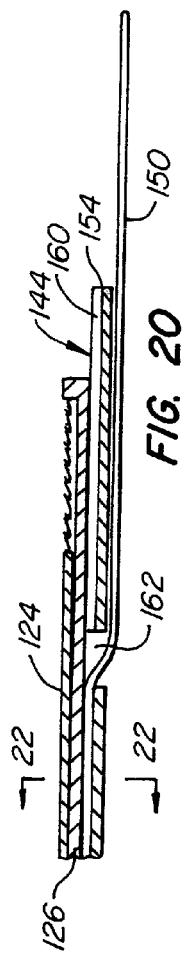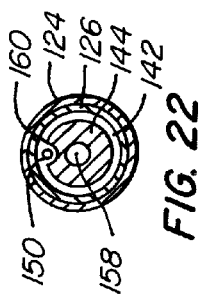

MEDICAL DEVICE AND METHOD

CROSS-REFERENCE TO OTHER APPLICATIONS

This application is a continuation of U.S. patent application Ser. No. 12/477,371 filed 3 Jun. 2009, which is a continuation in part of U.S. patent application Ser. No. 10/824,779 filed 15 Apr. 2004.

FEDERALLY SPONSORED RESEARCH OR DEVELOPMENT

None.

BACKGROUND OF THE INVENTION

Occlusive vascular disease is a common ailment in people resulting in enormous costs to the health care system. Blood clots and their accompanying plaque buildup are the most common type of occlusion. Removal of this disease from the body has been studied for several years and many techniques (devices and methods) have been studied and practiced. Sometimes the diseased/stenosed areas of the vessels may be removed by use of Embolectomy, Atherectomy, thrombolysis, etc. or angioplasty and/or stenting can repair the diseased vessel but all of these are not always effective. The deposit of sinuous plaque (arteriosclerosis) to the inner wall of arteries usually precedes clot formation. Several expensive devices (dilatation balloons, stents, mechanical cutters, etc.) have been introduced to fight this vascular occlusive disease, but none of which has proven to be the 'magic bullet' to treat this ubiquitous disease. Even when effective, these technologies often are effective for a short period of time. Because of the various problems with all of the techniques and approaches to solving this medical condition, there exists no particular method or device that is considered the most accepted mode of treatment.

Unfortunately, cancer too is a common ailment resulting in over 1,500 deaths every day in the U.S. (550,000 every year; the number two killer in the U.S. after vascular disease). Therapy modalities for cancer are plentiful and continued to be researched with vigor. Still, the preferred treatment continues to be physical removal of the cancer. When applicable, surgical removal is preferred (breast, colon, brain, lung, kidney, etc.). Often these cancers occur in the body channels that are actually not dissimilar to occlusions in the vasculature.

Even though there are many techniques and devices known in the art for removing blockages in the tubular channels of the body and/or for bypassing them with autogenous or synthetic means (both surgically and via a percutaneous, less invasive technique) and other passageways of the human body as well as removing other diseased tissue, there is a need to removed the diseased tissue and re-join healthy pieces of the tissue once the diseased tissue has been removed. This removed tissue may be removed because of many reasons some of which are (but certainly not limited to) cancerous or potentially cancerous material, vascular disease (or potential vascular disease), trauma to tissue, congenital disease of the tissue, etc.

BRIEF SUMMARY OF THE INVENTION

A first aspect of the invention is directed to a catheter/dilator assembly comprising a catheter assembly, a dilator and a compression element. The catheter assembly comprises a catheter, having a proximal catheter end, a distal catheter end, a lumen, and an outer catheter surface, and a material-directing element, movable between radially expanded and radially collapsed states, secured to and extending past the distal catheter end, the material-directing element having an axial length when in the radially collapsed state. The dilator comprises a hollow shaft within the lumen of the catheter, the hollow shaft having an outer shaft surface, a proximal shaft end, a distal shaft end and a recessed region in the outer shaft surface at the distal shaft end. The recessed region and the material-directing element are generally aligned with one another. A compression element covers the material-directing element to temporarily retain the material-directing element in a radially collapsed state. The recessed region is sized for receipt of at least substantially the entire axial length of the material-directing element so to reduce the radial cross-sectional dimension of the assembly at the material-directing element.

A second aspect of the invention is directed to a method for assembling a catheter/dilator assembly. A catheter assembly is selected. The catheter assembly comprises a catheter, having a proximal catheter end, a distal catheter end, a lumen, and an outer catheter surface, and a material-directing element, movable between radially expanded and radially collapsed states, secured to and extending past the distal catheter end. The material-directing element has an axial length when in the radially collapsed state. A hollow shaft of a dilator is inserted through the proximal catheter end and into the lumen of the catheter. A recess formed in the distal shaft end of the hollow shaft is positioned to underlie the material-directing element. The material-directing element is placed in the radially collapsed state. A first sleeve is slid in a proximal direction to a first position covering the distal shaft end of the dilator and over the material-directing element to maintain the material-directing element in the radially collapsed state.

A third aspect of the invention is directed to a dilator assembly. An elongate dilator comprises proximal and distal portions, a dilator tip at the distal portion, and a dilator lumen extending from the dilator tip to at least a first position along the dilator. The dilator also comprises a guide wire pathway extending from a second position at the proximal portion of the dilator to the first position. The dilator has an opening at the first position connecting the guide wire pathway and the dilator lumen. A flexible guide wire extends along the guide wire pathway, through the opening, through the dilator lumen and out of the dilator tip.

A fourth aspect of the invention is directed to a rapid exchange dilator assembly. A catheter comprises a catheter lumen extending between a distal catheter end and a proximal catheter end. An elongate dilator, removably housed within the catheter lumen, comprises a proximal portion extending to a proximal dilator end, a distal portion extending to a dilator tip, and a dilator lumen extending from the dilator tip to at least a first position along the dilator. The dilator comprises a guide wire pathway extending from the proximal portion of the dilator to the first position. The dilator has an opening at the first position connecting the guide wire pathway and the dilator lumen. A flexible guide wire, comprising a guide wire proximal end and a guide wire distal end, extends along the guide wire pathway, through the opening, through the dilator lumen and out of the dilator tip. The guide wire proximal end and the proximal dilator end are positioned proximally of the proximal catheter end, the guide wire distal end and the distal dilator end are positioned distally of the distal catheter end. Therefore, when the assembly is at a desired position within a body, the dilator can be removed leaving the catheter and guide wire in position.

A fifth aspect of the invention is directed to a method for providing access to a target site within a tubular structure of a patient. A distal catheter end of a first, guide catheter is positioned at a first position within a tubular structure of a patient. A rapid exchange dilator assembly is passed into the first catheter, the rapid exchange dilator assembly comprising a second catheter, the second catheter comprising a removable dilator, a guide wire and a second catheter lumen, the second catheter lumen housing the dilator and the guide wire. The dilator is removed from the patient leaving the second catheter and the guide wire within the patient. An operational device is passed through the second catheter for performing a procedure at the target site.

A sixth aspect of the invention is directed to funnel catheter comprising an outer tube, an inner tube slidably located within the outer tube, and a tubular sleeve having first and second ends and movable between a radially expanded, use state and a radially contracted, deployment state. The first end of the sleeve is secured to a distal end of the outer tube. The second end of the sleeve is secured to a distal end of the inner tube. The sleeve has a movable, generally U-shaped direction-reversing region so that when the first and second ends move relative to one another the position of the direction-reversing region moves relative to the distal ends of the inner and outer tubes, the direction-reversing region constituting the distal funnel catheter end.

A seventh aspect of the invention is directed to a method for deploying a material-directing element within a tubular structure within a patient. A funnel catheter, having a distal funnel catheter end, is selected. The funnel catheter comprises an outer tube, an inner tube slidably located within the outer tube, a tubular sleeve having first and second ends and movable between a radially expanded, use state and a radially contracted, deployment state, the first end of the sleeve being secured to a distal end of the outer tube, the second end of the sleeve being secured to a distal end of the inner tube. The sleeve has a movable, generally U-shaped direction-reversing region, the direction-reversing region constituting the distal funnel catheter end. The funnel catheter is deployed with the sleeve in a reduced diameter, deployment state and with the sleeve being generally parallel to the outer and inner tubes. The direction-reversing region is positioned at a chosen position within a tubular structure within a patient. The distal ends of the inner and outer tubes are moved relative to one another causing: the position of the direction-reversing region to move relative to the first and second ends, the sleeve to form a distally-opening material-directing funnel, the funnel having a distal funnel portion and a proximal funnel portion, and the distal funnel portion to contact the inner wall of the tubular structure.

An eight aspect of invention is directed to method for making a funnel catheter. Material is wound onto a mandril to create a tubular braided sleeve having a proximal portion, a distal portion, a proximal end, and a distal end. The tubular braided sleeve is removed from the mandril. The proximal end is secured to a first position on an outer tube and the distal end is secured to a second position on an inner tube to create a funnel catheter.

A ninth aspect of the invention is directed to a balloon funnel catheter comprising a shaft, having an end, a main lumen and an inflation lumen, and an annular balloon mounted to the end of the shaft and fluidly coupled to the inflation lumen for movement between a radially contracted, uninflated state and a radially expanded, inflated state. The balloon defines an open region opening into the main lumen when in the inflated state. The balloon extends distally past the end of the shaft when in the inflated state.

A tenth aspect of the invention is directed to a method for securing a tubular braid to a tube. A first end of a tubular braid is brought into engagement with an end portion of a tube, said end portion comprising a temporarily softenable tube material. The temporarily softenable tube material is then softened. The end portion of the tube and the first end of the tubular braid are merged into one another to create a tube material/tubular braid matrix.

An eleventh aspect of the invention is directed to a method for controlling the shape of a radially expandable and contractible tubular braid device. A radially expanded shape is chosen for the braid device when the braid device is in a radially expanded state, the radially expanded shape having a length and different cross-sectional dimensions at selected positions along the length. A material is selectively applied to at least some of the selected positions along the braid device. The stretch resistance of the material is adjusted according to the selected positions. Therefore, the different stretch resistances at the selected positions cause the braid device to assume the chosen radially expanded shape when the braid device is in the radially expanded state.

A twelfth aspect of the invention is directed to a method for imparting a shape to a thermoplastic membrane. At least a portion of a radially expandable device is surrounded with a thermoplastic membrane. The radially expandable device is radially expanded to a chosen expanded configuration thereby reshaping the thermoplastic membrane to assume an expanded state corresponding to the chosen expanded configuration. A set is imparted to the thermoplastic membrane while in the expanded state.

A thirteenth aspect of the invention is directed to an anastomotic medical device comprising a tube, having first and second ends and a lumen extending therebetween, and an anchor member at the first end for securing the first end to a first tubular structure of a patient, the first tubular structure having a first open interior, with the first open interior opening into the lumen.

A fourteenth aspect of the invention is directed to an anastomotic medical assembly comprising first and second anastomotic medical devices. The first anastomotic medical device comprises a first tube, having first and second ends and a first lumen extending therebetween, and a first anchor member at the first end of the first tube for securing the first end of the first tube to a first tubular structure of a patient. The first tubular structure has a first open interior, with the first open interior opening into the first lumen. The second anastomotic medical device comprises a second tube, having first and second ends and a first lumen extending therebetween, and a second anchor member at the first end of the second tube for securing the first end of the second tube to a second tubular structure of a patient. The second tubular structure has a second open interior, with the second open interior opening into the second lumen. The second ends of the first and second tubes are connected to one another to create a fluid path between the first and second anchor members. Therefore, the first and second open interiors of the first and second tubular structures of the patient may be fluidly connected.

Various features and advantages of the invention will appear from the following description in which the preferred embodiments have been set forth in detail in conjunction with the accompanying drawings.

BRIEF DESCRIPTION OF THE DRAWINGS

FIG. 19 is an enlarged side view of the proximal and distal portions of a rapid exchange dilator assembly;

FIG. 20 is a partial cross sectional view of the distal end of the assembly of FIG. 19;

FIGS. 21 and 22 are cross sectional views taken along lines 21-21 and 22-22 of FIGS. 19 and 20, respectively;

DETAILED DESCRIPTION OF THE INVENTION

Figure 1:
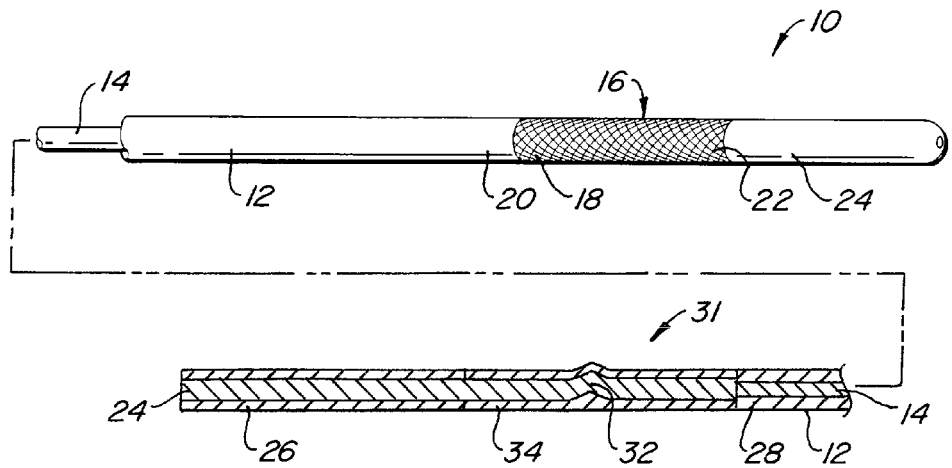
FIGS. 1 and 2 illustrate an expandable element guide wire in radially contracted and radially expanded states.

There is a continuing need for improved medical devices and methods to meet some or all the following objectives.

The first objective is to reduce cost. This is particularly important in recent years where it is clear for safety and sanitary reasons that these will be single use devices. A device, even though it performs a function in some improved manner, will not be widely used if it is considerably more costly than the alternatives available.

A second objective is to provide a device that is simple to use and in a very real sense simple to understand. This will encourage its adoption and use by medical personnel. It will also tend to keep cost low.

The third objective is to provide a device that entails a procedure with which the medical profession is familiar so that the skills that have been learned from previous experience will continue to have applicability.

A fourth objective relates to the effectiveness and thoroughness with which the device performs, such as blockage removal or anastomotic device placement. For example, it is important that a maximum amount of the blockage be removed; recognizing that no device is likely to provide one hundred percent removal. With regard to bypassing or re-joining, it is important that an optimum amount of the tissue be removed and therefore replaced; recognizing that no device is likely to provide one hundred percent optimization.

A fifth objective concerns safety; a matter, which is often so critical as to trump the other considerations. It is important to avoid tissue trauma. In many circumstances, it is critically important to, for example, avoid breaking up a blockage in a fashion that leads to flushing elements of the blockage throughout the body involved. In the case of using an anastomatic device in the tubular channels of the body, it is critically that the joining of the anastomosis does so while minimizing tissue trauma. Often this trauma is not realized immediately after surgery. Even further, leakage must be kept near zero.

There are trade-offs in design considerations to achieve the above five interrelated objectives. Extreme simplicity and a very simple procedure might over compromise safety. Addressing all of these considerations calls for some trade-off between the objectives.

Clot Dragger Lock

One aspect of the instant invention relates to a locking mechanism for the blocking or engaging element. Of particular relevance is the locking mechanism of the engaging element. One such preferred embodiment incorporates an interference fit when and inner and outer slidable elongate member is used. Once deployed, the force required to keep the engaging element is usually small in relation to the force required to deploy (in the case of a non-self-expanding mechanism). In this case, a slight interference fit between the inner and outer slidable elongate members can be overcome easily by the interventionalist, but when the engaging or blocking element is deployed (partially or fully), the interference fit creates enough force of the system to remained deployed. The same invention could be used in the case where either the engaging element or blocking element is self-expanding, but in this case the interference fit would keep either element in the un-deployed, un-expanded condition.

This aspect is particularly useful for the engaging element because such an interference fit can be constructed particularly small. In the case of where the matter removal system of the instant invention is used percutaneously (through the skin) and a needle is used for the initial entry of the engaging element, it may be inserted through the small needle (usually 19, 18 or 21 gauge needle that is typically used for such intervention) and then deployed. In this case the needle is removed and it needs to be removed over the elongate shaft of the engaging element (wire guide). In order for it to be removed easily, the locking mechanism must be small or negligible with respect to the shaft of the elongate engaging element. A preferred embodiment of this locking mechanism in the case where the engaging element has an inner elongate member is to put a slight bend or kink in the inner member that interferes/impinges against an outer tubular elongate member. In particular, there may be three components to the outer tubular elongate member to facilitate said locking of the engaging element. The first component is the main and longest part of the shaft of the elongate member. This material can be matched to the required characteristics required for the shaft such as torqueability, steeriblity, flexural modulus, softness, stiffness, etc. This first component may be attached to the proximal side of the engaging element mechanism, but not attached to the inner tubular or wire elongate member contained within. The second component could be located proximal to the main shaft. This embodiment would be a handle type tubular element that would be sized to fit the physician's fingers, approximately 0.5-2.0 inches in length. It would not be glued or otherwise attached to the inner member. It would be manufactured of a material that might be different from the main shaft where characteristics of the first and second component could be different. The outside surface of this handle may be roughened or have some high friction coating put on it that would aid with the physician grasping the handle. This second component may require some 'stiffness' in it in such a case where the inner tubular or wire elongate member is kinked or otherwise bent. This second material may be harder or stiffer so that the kink on the inner member that prevents axial motion does not flex or distort the material. This second material stiffness might be such that it is important that the kink or bend in the inner member interfere enough and have enough force to hold the expanding element in place once deployed (or un-deployed in the case of the expanding mechanism being in the smaller unexpanded condition). Further, to create the appropriate interference, the inner diameter of this second component could be even smaller than the inner tubular or wire elongate member. It is possible to design an inner diameter of this second component to be 0.0001 to 0.002 inches smaller in diameter than the inner elongate member. This interference fit would be sufficient to hold the expanding mechanism expanded or unexpanded yet the interference force would not be too great that the physician could not overcome the force easily to deploy or un-deploy the mechanisms. Further a combination of smaller or equal or slightly larger inner diameter of this second component than the diameter of the inner elongate member could be coupled with the kink/bend/ferrule or other diametrical addition such as a drop of glue or epoxy to cause a brief interference fit could be used for locking either expandable mechanism.

The third component may be approximately the same outside diameter of the first and second component, but would like be glued or otherwise attached to the inner tubular member by glue or other adhesive, heat staking (or melting the polymeric handle to the inner member) or a 'pressed' interference fit so that this third component would move in tandem with the inner elongate member.

Hence in such a configuration, the physician would use his/her two hands (two fingers on each hand) to deploy and un-deploy and lock and unlock the expanding and contracting mechanisms respectively. This is accomplished by the physician grasping the third component with one hand and the second component with the second hand and pulling the two components apart so that a space would be created between the two components nearly equal to the distance that is changed from the deploying/undeploying distal element.

To aid with ease of use, the two handles may be color coded so that the physician would realize the difference between the two handles and for education in training them to use the locking mechanism.

Figure 2:
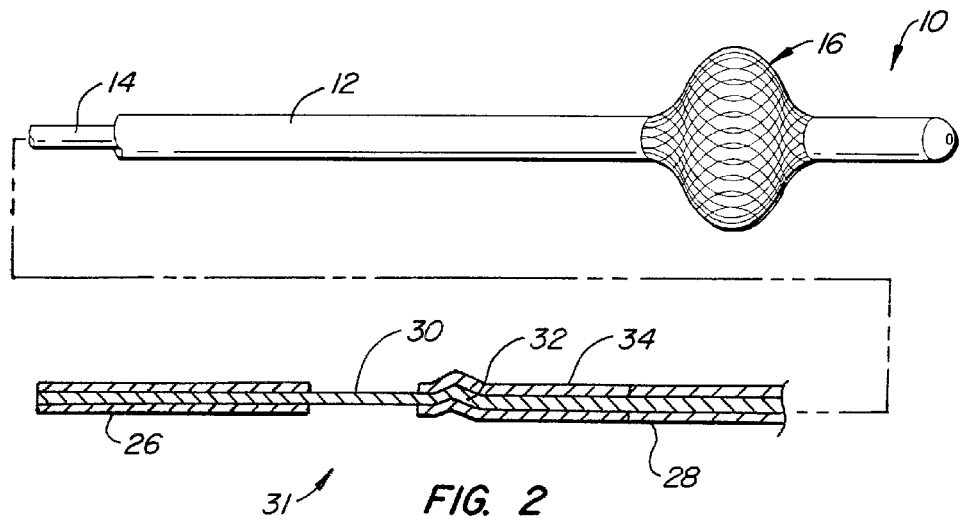
Figure 3:
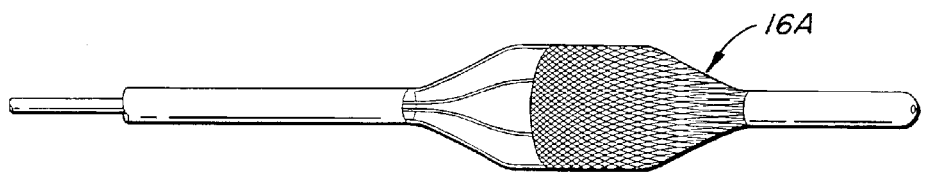
FIG. 3 illustrates an alternative embodiment of the expandable element guide wire of FIG. 2.

FIGS. 1 and 2 illustrate an expandable element guide wire 10 comprising outer and inner guide wires 12, 14. A braided expandable element 16 has a proximal end 18 secured to the distal end 20 of outer guide wire 12 and a distal end 22 secured to the distal end 24 of inner guide wire 14. The proximal end 24 of inner guide wire 14 has a deployment grip 26 secured thereto. The proximal end 28 of outer guide wire 12 is spaced apart from deployment grip 26 to create a locking region 30. Relative movement between the outer and inner guide wires 12, 14 can be restricted by a guide wire lock 31. Guide wire lock 31 includes a kink 32 in inner guide wire 14 along region 30 and a kink engagement sleeve 34 slidably mounted on region 30 of inner guide wire 14. Kink engagement sleeve 34 may be secured to outer guide wire 12 or not. A suggested in FIG. 2, pulling on inner guide wire deployment grip 26 to separate proximal ends 24, 28, while maintaining kink engagement sleeve 34 adjacent to proximal end 28 of outer guide wire 12, causes kink 32 to move within the deformable kink engagement sleeve 34. The resistance to kink 32 moving within kink engagement sleeve 34 maintains expandable element 16 at the radially contracted condition of FIG. 1 or at any of a range of radially expanded conditions, such as that shown in FIG. 2. Expandable element 16 may be another type of expandable element, such as a malecot type of expandable element (that is a tube having a number of longitudinally extending slits) or a wire basket/expandable braid expandable element 16A as shown in FIG. 3. Also, kink 32 could be replaced by other types of a engagement sleeve-deforming structure, such as a ball or ring of material positioned along locking region 30.

Catheter/Dilator Assembly and Method

Another aspect of this invention is particularly adapted to the removal of blockages or particulate (matter) in hollow tissues. This aspect combines a catheter having a blocking feature that block the annulus between the catheter and the vessel or other hollow tissue. Said catheter may have an inner support wire having an occlusion-engaging element also.

Said support wire extends through the catheter, through or around the occlusion, and at its distal end has an annular braided element attached thereto or a malecot style element with two or more slits in a tube. The support wire is a dual element support wire having a core and an annular shell that slides on the core. The distal end of the core is attached to the distal end of the annular braided element (or slit-tube/malecot) and the distal end of the shell is attached to the proximal end of the annular braided element (or slit-tube/malecot). Thus movement of the core and shell relative to one another moves the braided element from a radially retracted position, which is useful for insertion through the catheter to a radially expanded position, which expands it to the sidewall of the graft. When the annular engaging element is in its radially compressed state, it can be passed through or around the occlusion together with the rest of the wire to reside on the distal end of the occlusion. When the engaging element is expanded and moved proximally (that is, in a retrograde fashion), it will engage the occlusion and force the occlusion into the catheter. Alternatively, no motion of the engaging element may be required if aspiration is applied. Further, aspiration and proximal motion of the engaging element may be used together in a synergistic fashion to remove the occlusion.

The distal end of the catheter is proximal of the occlusion and contains a blocking mechanism that extends radially from the distal end of the catheter to the wall of the graft or body passageway. This catheter-blocking element also has a radially retracted insertion state and a radially expanded blocking state. The blocking element is a multi-wing malecot type device, which may be covered by a thin elastomeric film or membrane. An alternative design of the blocking element is a mechanism of tubular mesh braid, which may be covered as well.

This malecot (or the mechanism of tubular mesh braid) is bonded to the distal end of the catheter or an integral part of the catheter. The blocking element (or the engaging element for that matter) is deployed in several different ways: 1.) The distal tip of the dilator, over which the catheter is inserted, has a slightly increased diameter. This tip is in the nature of a ferrule. When the dilator is removed or pulled in a retrograde (out of the body), the ferrule abuts against the distal end of the multi-wing malecot (or tubular mesh braid) pushing this blocking element from its radially compressed state into its radially expanded state. 2.) Alternatively, the tip of the dilator can be bonded to the catheter with a breakaway bond so that when the dilator is removed, the blocking element is expanded in a similar fashion. In this radially expanded state, the malecot (or tubular mesh braid) and its film cover (if required) blocks the annulus around the catheter so that the occluded blood, emboli, plaque or other obstruction which is being removed is forced into the catheter where it is aspirated, obliterated or otherwise removed. 3.) Further, both the blocking element or the engaging element could be formed of such materials that have a memory and hence are self-expanding. These materials are varied from polymers to metals including, but certainly not limited to: PEBAX, nylons, polyurethanes, polyethylenes (HDPE, UHWPE, LDPE, or any blend of the aforementioned polyethylenes), PET, NiTi, MYLAR, (Nickel Titanium Alloy; with or without TWSM (Two Way Shape Memory or superelastic properties). In the case of self-expanding blocking or engaging elements, the larger, expanded configuration could be constrained by an outer tube to keep it in a smaller unexpanded configuration; alternatively an inner support member could be used to keep the elements in the smaller unexpanded configuration. 4.) Even further, both the blocking and engaging elements can be deployed by moving two slidable elongated elements with respect to one another. This motion of the two slidable elements would cause the blocking or engaging element to become expanded and/or unexpanded.

Dilator Recess

Another aspect of the instant invention is related to the expanding mechanism on the blocking or engaging element, but likely more pertinent to that of the blocking element on the catheter or tubular device. This aspect is related to decreasing the space required for placement of the blocking element in the un-deployed, unexpanded condition. In the case where a percutaneous entry is made into a hollow organ, the most common approach to entry is a technique known as 'dilation' or more specifically the 'Seldinger Approach' to dilatation (after a Dr. Seldinger in the mid 1900's). This is where the interventionalist uses a needle to enter the body, then a guidewire is placed through the needle and the needle is removed as stated above. Then an assembly known as a dilator/sheath assembly is inserted over the guide wire and into the body. The dilator/sheath assembly is made up of an inner dilator with a hole though the middle of the usually somewhat solid cylindrical dilatory for inserting the guidewire there through. The dilator is tapered like a cone usually on a small degree taper approximately 4-20 degrees. The sheath consists of a thin walled tube usually made from PTFE, FEP, polyurethane, PEBAX or similar material and fits snugly over the inner dilator. Conventionally, once the physician dilates into the body, the inner dilator is removed so that the physician has access to the body thorough the thin walled dilatory (0.004-0.018 inches thick). How this relates to the instant invention is interesting in that the inner dilator usually tends to be somewhat 'solid' in it's cylindrical configuration, but it can have a recess or groove in the cylindrical portion of the dilator for a certain portion of the dilator usually located near the distal end of the device. This recess or groove is a convenient place for the expanding blocking (or engaging for that matter) element to rest in while the device is being placed within the body. This placement of the blocking or engaging element for that matter allows more material to be placed in the device without increasing the overall diameter of the device which is particularly important so that the physician does not have to make an access site/puncture/hole into the body larger than what is absolutely necessary. This dilator may have a lumen with a side port to enable the monorail configuration described below under Rapid Exchange. A long dilator configuration can be used to support devices traversing vessels spanning the length of the human body. By incorporating the monorail feature, the dilator can be removed from a device and guidewire that is only slightly longer than the dilator shaft.

Figure 4:
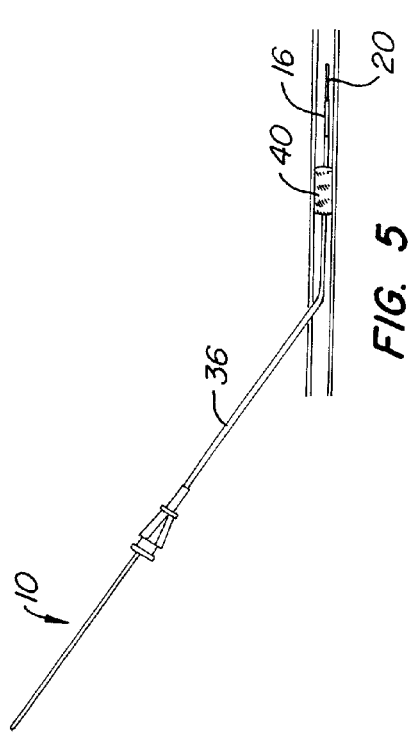
FIG. 4 illustrates a needle inserted into a graft near an occlusion.
Figure 5:
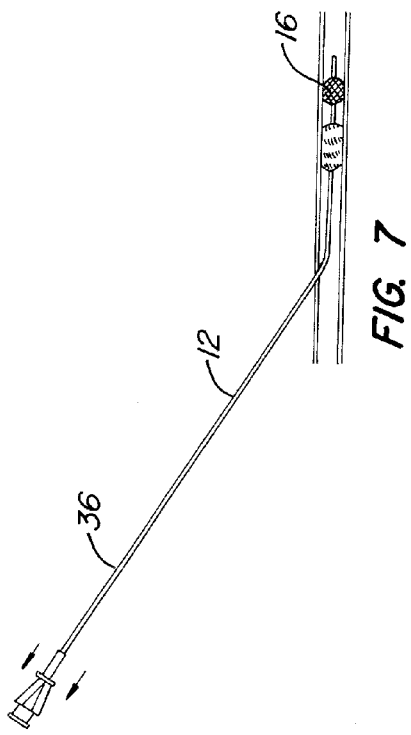
FIGS. 5-7 illustrate insertion of an expandable element guide wire through the needle of FIG. 4, expanding the expandable element and then removing the needle leaving the guide wire in place.
Figure 6:
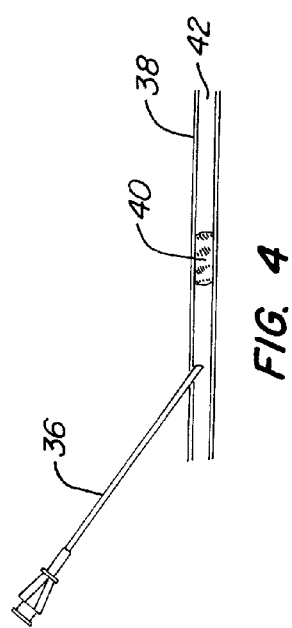
Figure 7:
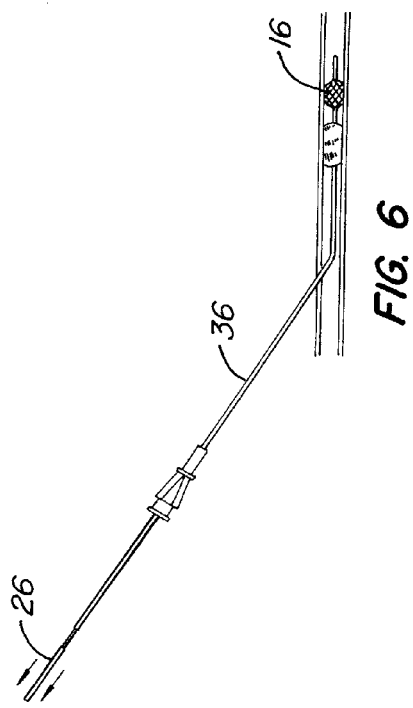

FIGS. 4-18A illustrate novel method and apparatus in conjunction with an exemplary thromboectomy procedure. FIG. 4 illustrates a needle 36 inserted into a graft 38, or other tubular structures such as a blood vessel, having an occlusion 40 within a lumen 42. An expandable element guide wire 10 is shown in FIG. 5 passing into lumen 42 with the aid of needle 36 with expandable element 16, in a radially contracted state, positioned distally of occlusion 40. FIG. 6 illustrates expandable element 16 placed in a radially expanded state by pulling on deployment grip 26. FIG. 7 illustrates removal of needle 36 while leaving guide wire 10 in place.

Figure 8:
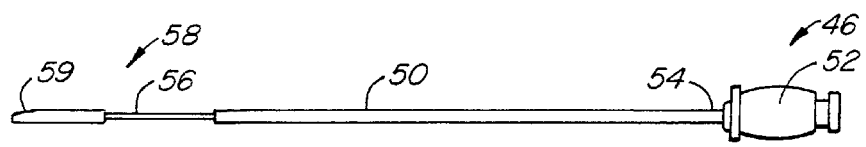
FIG. 8 illustrates a recessed dilator.
Figure 9:
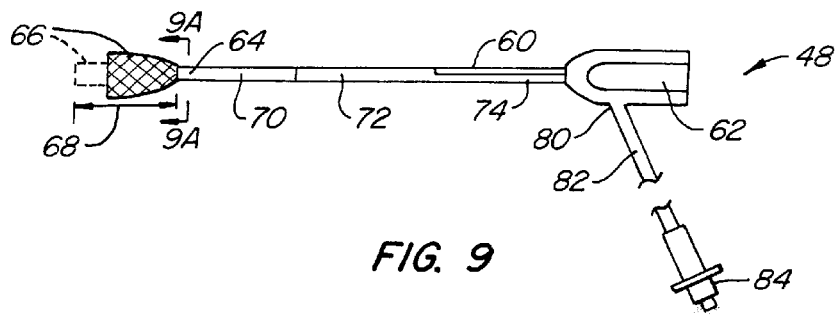
FIG. 9 illustrates a funnel catheter assembly.

FIG. 8 illustrates a recessed dilator 46 to be used with the funnel catheter assembly 48 of FIG. 9. Dilator 46 includes a hollow shaft 50 having a fitting 52 at a proximal shaft end 54 and a recess 56 at a distal shaft end 58. Shaft 50 terminates at a tip 59.

Figure 9A:
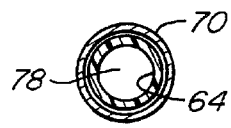
FIG. 9A is a cross sectional view taken long line 9A-9A of FIG. 9.
Figure 10:
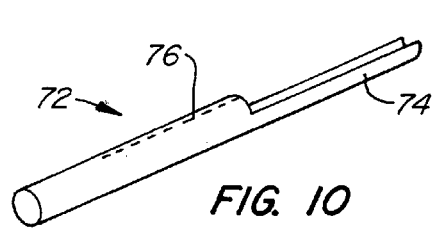
FIG. 10 is an isometric view of the split stopper sleeve of FIG. 9.

FIGS. 9, 9A and 10 illustrate funnel catheter assembly 48 to include a catheter 60 extending from a proximal catheter end 62 to a distal catheter end 64. A radially collapsible funnel element 66 extends from distal catheter end 64. Funnel element 66 is preferably a braided funnel element having a normally radially expanded state, shown in solid lines in FIG. 9, and a radially collapsed state, shown in dashed lines in FIG. 9. Funnel element 66 has an axial length 68 in its radially collapsed state. Funnel catheter assembly 48 also includes a compression sleeve 70 and a split stopper sleeve 72, both slidably mounted on catheter 60. Split stopper sleeve 72 is also illustrate in FIG. 10 and has a cutaway proximal sleeve portion 74 and a weakened region 76, the purpose for which will be discussed below. Catheter 60 has a lumen 78, see FIG. 9A, for receipt of hollow shaft 50. Proximal catheter end 62 has a port 80 connected to a tube 82 with a fitting 84 at the end of the tube. This permits fluid or other flowable material to be directed through lumen 78.

Figure 11:
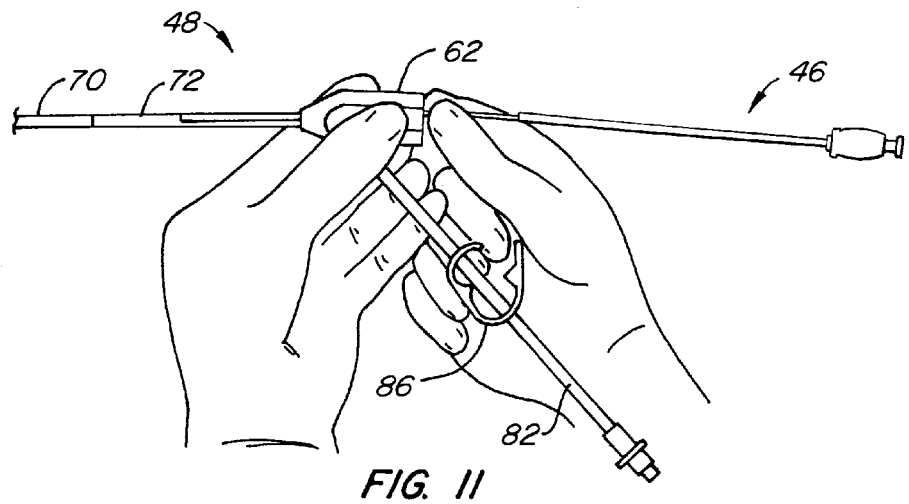
FIG. 11 shows inserting the recessed dilator of FIG. 8 into the funnel catheter assembly of FIG. 9 to create a funnel catheter/dilator subassembly.
Figure 12:
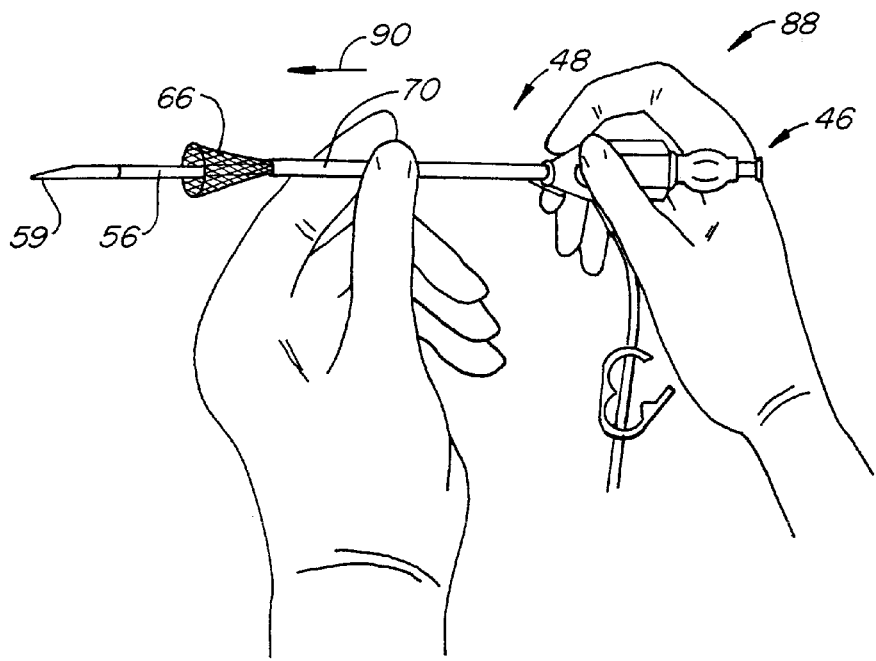
FIGS. 12 and 13 show movement of the compression sleeve over the funnel element of FIG. 11.
Figure 13:
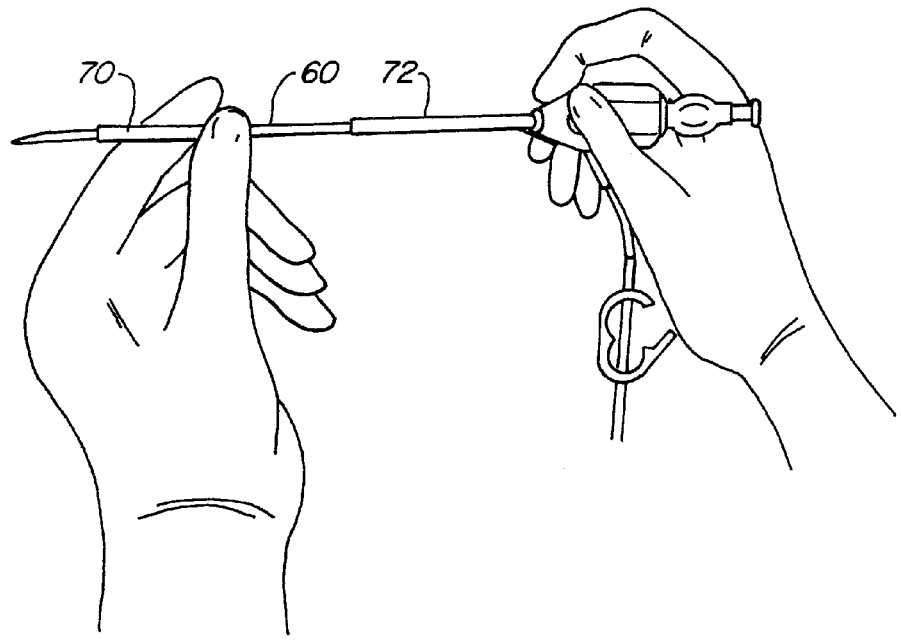

FIG. 11 illustrates a user inserting tip 60 of shaft 50 of recessed dilator 46 into proximal catheter end 62 of funnel catheter assembly 48. A tube clamp 86 is shown mounted along tube 82. FIG. 12 illustrates recessed dilator 46 fully inserted into funnel catheter assembly 48 to create a funnel catheter/dilator subassembly 88. Funnel element 66 is shown aligned with and overlying recess 56 with the user preparing to slide compression sleeve 70 in the direction of arrow 90. FIG. 13 shows compression sleeve 70 fully covering funnel element 66 and leaving a portion of catheter 60 between the compression sleeve and split stopper sleeve 72 exposed. The provision of recess 56 and the alignment of funnel 66 with recess 56 help to minimize the outside diameter of subassembly 88, thus helping to minimize patient trauma.

Figure 14:
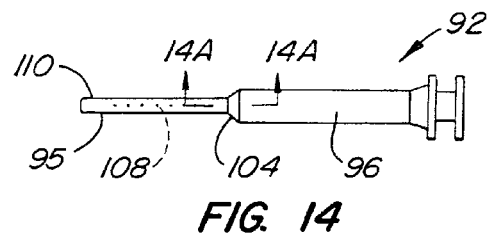
FIG. 14 is an enlarged side view of a tearaway sleeve.
Figure 14A:
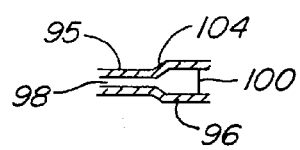
FIG. 14A is a cross sectional view taken long line 14A-14A of FIG. 14.
Figure 15:
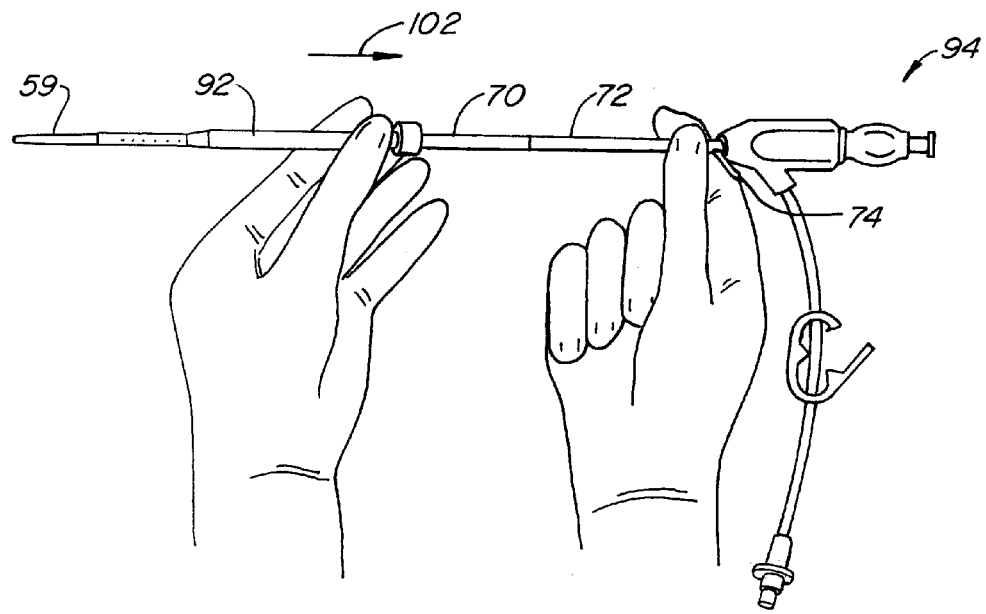
FIG. 15 illustrates sliding the tearaway sleeve of FIG. 14 onto the subassembly of FIG. 11 to create a catheter/dilator assembly.

FIG. 14 illustrates a tearaway sleeve 92 used with subassembly 88 to create the catheter/dilator assembly 94 of FIG. 15. Sleeve 92 has a smaller diameter distal portion 95 and a larger diameter proximal portion 96. The inside diameter 98 of distal portion 95 is sized to fit snugly over distal shaft end 58 of shaft 50 and funnel 66 within recess 56. Inside diameter 100 of proximal portion 96 is sized to fit snugly over catheter 60. Therefore, sliding sleeve and a proximal direction, that is in the direction of arrow 102 as shown in FIG. 15, causes proximal portion end 96 to contact compression sleeve 70 and initially drive compression sleeve 70, and then both compression sleeve 70 and split stopper sleeve 72, in a proximal direction until the junction 104, see FIG. 14A, between distal and proximal portions 95, 96 of sleeve 92 generally abuts distal catheter end 64 of catheter 60. The proximal movement of split stopper sleeve 72 is accommodated by proximal sleeve portion 74 deforming and/or deflecting as illustrated in FIG. 15. The outside diameter of distal portion 95 is about equal to the inside diameter 100 of proximal portion 96.

Figure 16:
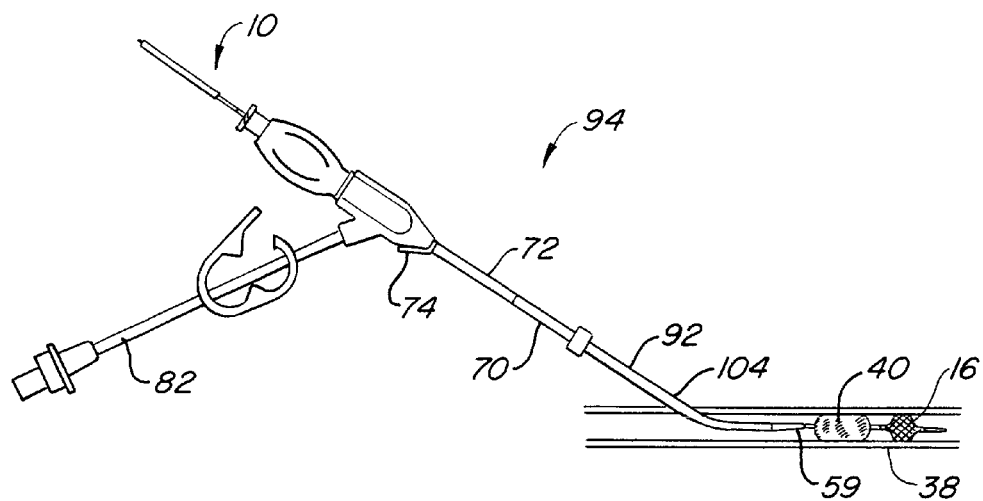
FIG. 16 illustrates the result of sliding the assembly of FIG. 15 over the expandable element guide wire of FIG. 7.
Figure 17:
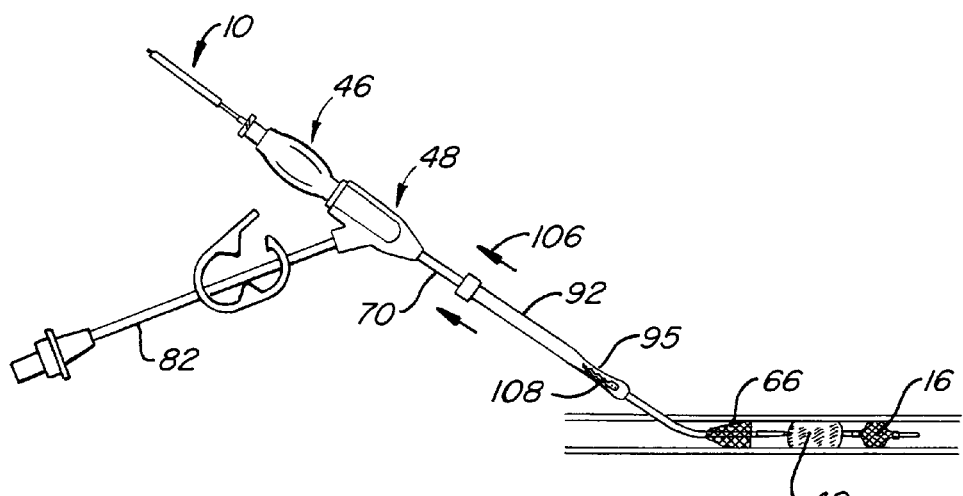
FIG. 17 illustrates the assembly of FIG. 16 after the tearaway sleeve has been pulled proximally to allow the funnel to expand.
Figure 18:
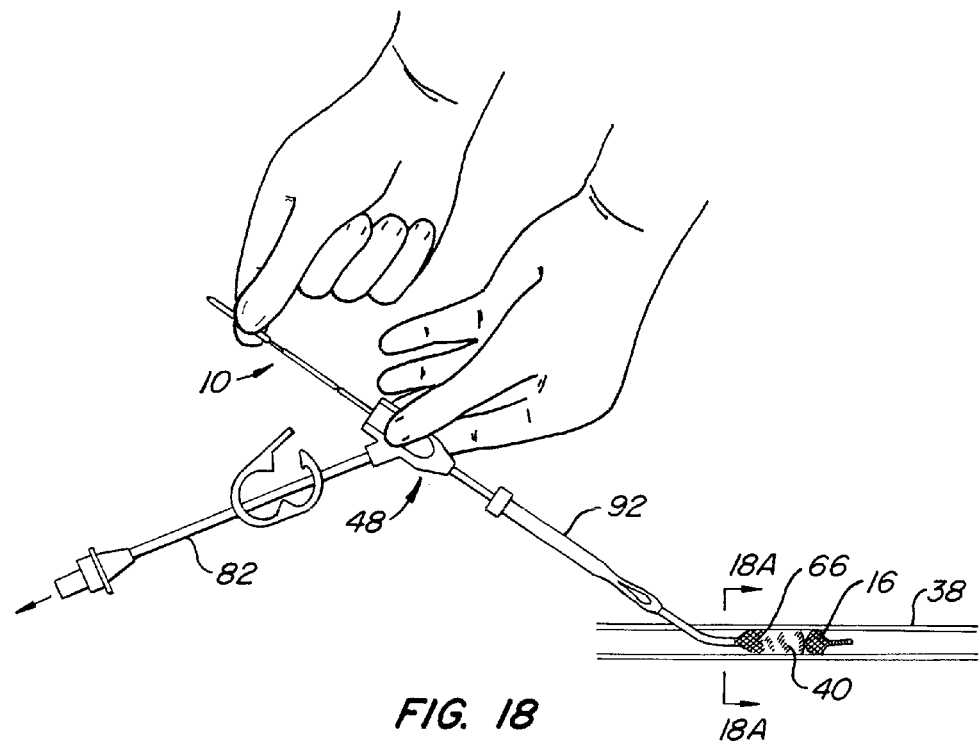
FIG. 18 shows manipulating the apparatus of FIG. 17 to drive the occlusion into the funnel.
Figure 18A:
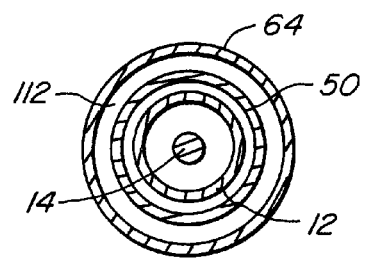
FIG. 18A is an enlarged cross sectional view taken long line 18A-18A of FIG. 18.

FIG. 16 illustrates catheter/dilator assembly 94 mounted over expandable element guide wire 10, see FIG. 7, with tip 59 positioned proximally of occlusion 40. It is preferred that the junction 104 remains outside of graft 38 to minimize the size of the access opening in the graft through which tip 59 passes. To permit funnel element 66 to expand, tearaway sleeve 92 is pulled proximally as indicated by arrows 106; because inside diameter 98 is smaller than the outside diameter of catheter 60, this movement is accommodated by a weakened region 108, see FIG. 14, of distal portion 95 of sleeve 92 splitting open. It is preferred that the tip 110 of distal portion 95 not split open so to accommodate any future manipulation of the assembly. This movement also causes split stopper sleeve 72 to tear along weakened region 76 thus permitting sleeve 72 to be completely removed from the apparatus. To remove occlusion 40, the user may pull on guide wire 10 causing expandable element 38 to drive occlusion 40 towards funnel 66; a suction force may be created in tube 82, typically using a vacuum syringe attached to fitting 84, and thus in a vacuum space 112 created between distal catheter end 64 and shaft 50 as shown in FIG. 18A. Depending upon the composition of occlusion 40, the occlusion may be drawn completely into tube 82. Tube 82 may be sufficiently transparent or translucent to allow the presence of the remains of occlusion 40 to the visually observed by the user within the tube.

Rapid Exchange

Another aspect of the invention relates to designs that provide for the manufacture and function of the matter removal system. One such aspect has been often referred to as a 'Rapid Exchange' or 'Mono Rail' feature. This common feature is usually used for elongated catheters when used in conjunction with guide wires (AKA wire guides). Usually an interventionalist inserts a guidewire into the body via an existing opening or through a percutaneous opening often created by a needle. The guidewire, because it is a small wire, is easier to manipulate into position than would be a catheter or other elongated device. Once in place the interventionalist usually inserts the elongated catheter or other device over the guidewire to the appropriate position hence the reason for the name guide wire. Before the development of Rapid Exchange or Mono Rail techniques, the interventionalist would need to use a guide wire that was more than twice the length of the elongated catheter or device so that the device could be inserted over the wire outside of the body while the guidewire stayed in place in the appropriate position within the body. This 'double length feature' provided the interventionalist the safety of inserting the device over the guidewire and at the same time holding the guidewire in place so that it does not move from the desired location within the body. This technique was cumbersome because of the double length of the guidewire. The Rapid Exchange or Mono Rail technique provide for a small hole at the distal end of the catheter or device with that hole/lumen exiting the catheter or device a short distance from the distal end, usually approximating 3-12 (7.6-30 cm) inches from the distal end of the device.

This aspect of the invention is a variation of the Rapid Exchange feature. A dilator is used within the tubular catheter or device of the instant invention whereby the dilator has the feature of having an hole from or near the distal end and then exiting some 3-12 inches from the distal end, but instead of sliding the catheter or device of the instant invention 'over' the guidewire, the guide wire is loaded in place inside the dilator which is inside the tubular elongate lumen of the instant invention. When the assembly gets near the trouble area in the body to be intervened, the interventionalist would then be able to steer the wire from within the dilator, but outside of the body. This allows the similar feature of the aforementioned Rapid Exchange or Mono Rail technique. When the interventionalist is near the area to be treated, he/she can remove the inner dilator leaving the inner guidewire in place and hence obviating the need for a double length guidewire.

FIGS. 19-22 illustrate a rapid exchange dilator assembly 116 comprising a catheter 118 having a distal catheter end 120 and a proximal catheter end 122. Catheter 118 includes an outer catheter 124 and an inner catheter 126 slidably housed within the outer catheter. Outer catheter 124 includes an outer catheter fitting 130, fitting 130 including a conventional sealing element 132 to create a fluid seal between outer catheter 124 and a proximal portion 134 of inner catheter 126. While outer and inner catheters 124, 126 are preferably flexible along most of their lengths, proximal portion 134 of inner catheter 126 and the proximal portion 136 of outer catheter 124 are both preferably made of metal tubing Inner catheter 126 also includes an inner catheter fitting 138 having a fluid port 140 opening into a catheter lumen 142 of catheter 118.

Assembly 116 also includes a dilator 144, having a distal portion 146 and a proximal portion 148, and a guide wire 150 extending generally parallel to dilator 144. In the assembled configuration of FIGS. 19-22, guide wire 150 has a tip 152 extending beyond dilator tip 154 and a guide wire proximal end 156 extending through and past inner catheter fitting 138. Proximal portion 148 of dilator 144 has a relatively small diameter to provide sufficient room for the passage of guide wire 150 through catheter lumen 142 as shown in FIG. 21. However, it is desired to minimize the diameter of catheter 118 and also have guide wire 150 pass through the dilator lumen 158 at dilator tip 154. Therefore, a guide wire pathway in the form of a groove 160 is formed along dilator 144 to accommodate guide wire 150. Towards dilator tip 154, such as about 15 cm from tip 154, an opening 162 is formed in dilator 144 coupling groove 160 and dilator lumen 158 to permit guide wire 150 to pass along groove 160, through opening 162, along lumen 158 and out through dilator tip 154. See FIG. 20. The guide wire pathway may also be created by a lumen formed in dilator 144 or by a separate tubular element mounted to the dilator.

Catheter 118 also includes an expandable braid 164 connected to the distal ends of outer and inner catheters 124, 126. Pulling inner catheter fitting 138 relative to outer catheter fitting 130 causes braid 164 to expand. While braid 164 may expand in a manner similar to that shown in FIGS. 1 and 2, it may also expand to create a funnel-type material-directing element as shown in FIGS. 9 and 12, discussed above, or in FIGS. 29-54, discussed below. Inner catheter fitting 138 also includes a dilator/guide wire seal element 166 permitting a seal to be created between proximal portion 134 of inner catheter 126 and proximal portion 148 of dilator 144.

Figure 23:
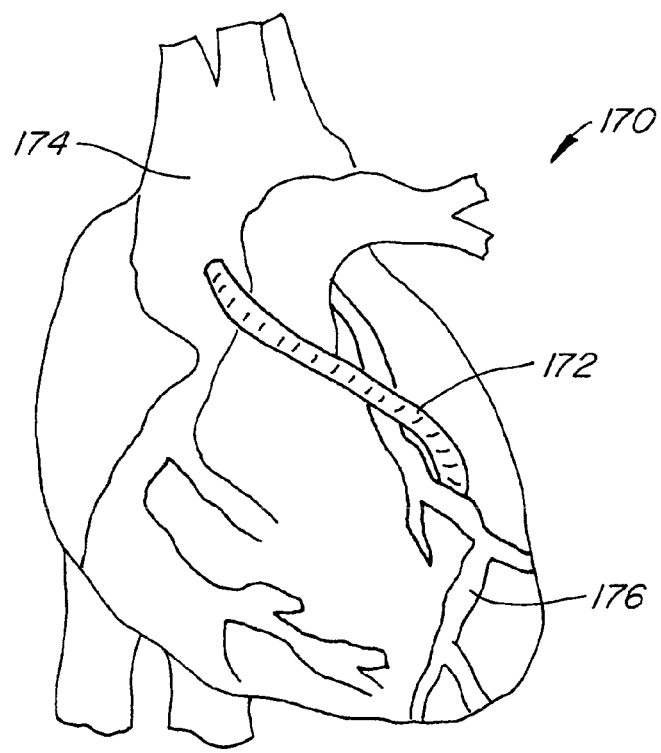
FIG. 23 shows a heart having a bypass graft connecting the ascending aorta and a coronary artery.
Figure 24:
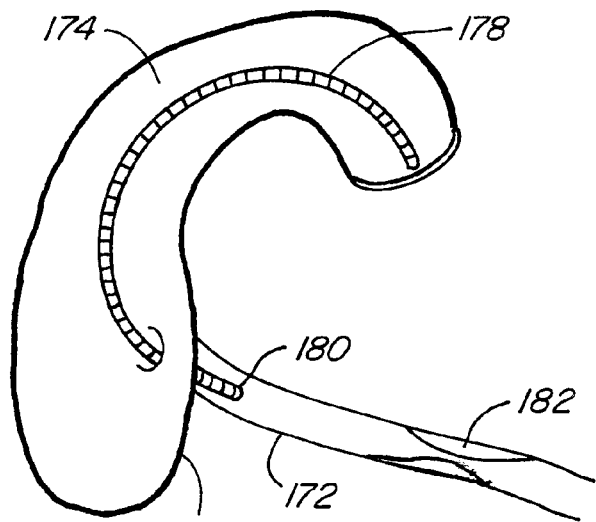
FIGS. 24-28 illustrates the use of the rapid exchange dilator assembly of FIG. 19 to access a position along the bypass graft of FIG. 23.
Figure 25:
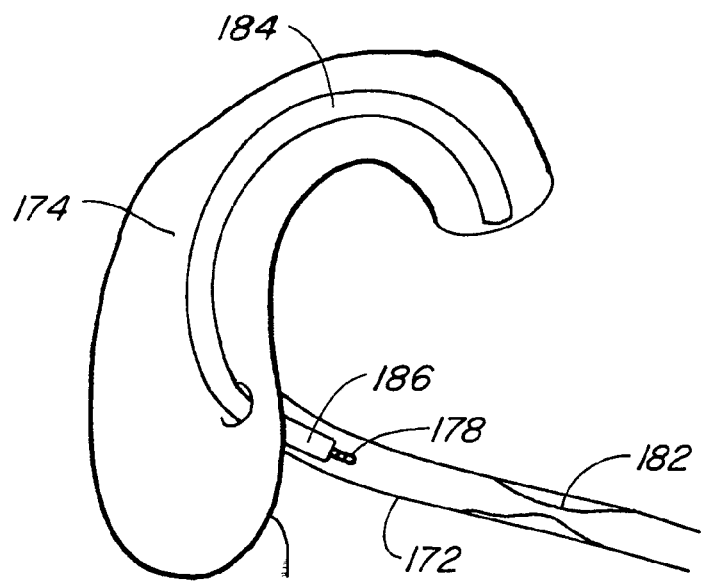
Figure 26:
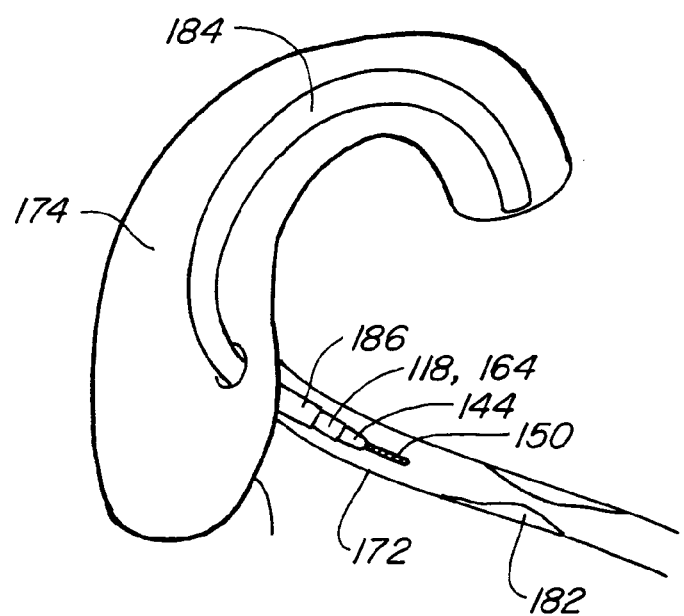
Figure 27:
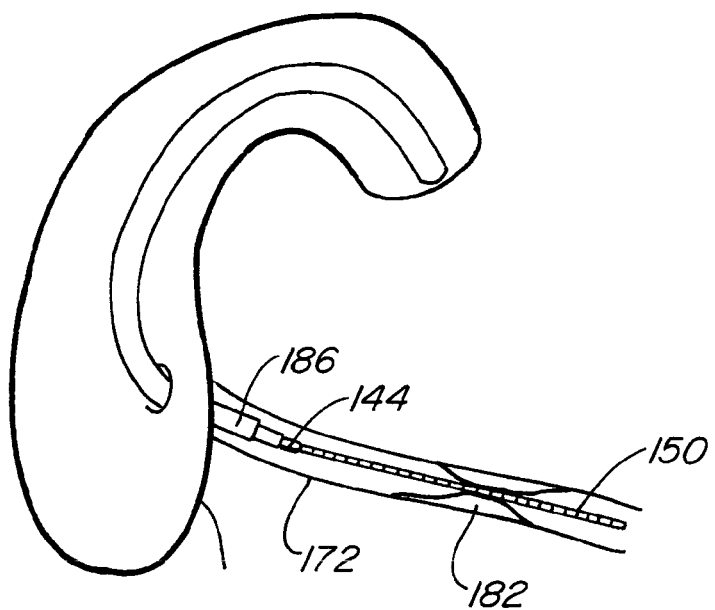
Figure 28:
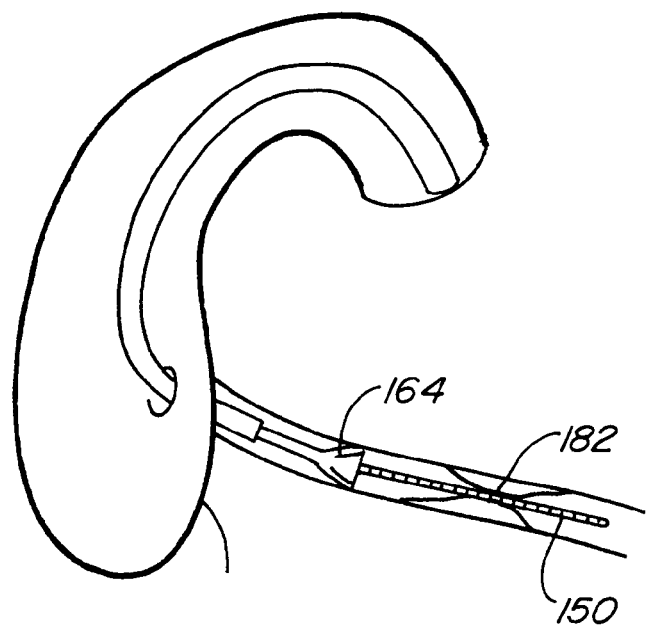

FIG. 23-28 will be used to describe an exemplary use of rapid exchange dilator assembly 116. FIG. 23 illustrates a heart 170 including a bypass graft 172 connecting the ascending aorta 174 with a coronary artery 176. FIG. 24 illustrates the passage of the first guide wire 178 through ascending aorta 174 and into bypass graft 172 with the tip 180 of first guide wire 178 positions near, in this example, a lesion 182. Guide wire 178 is typically a large, such as 0.038 in. diameter, guide wire commonly used to help the physician to get to the general vicinity of the treatment site. Thereafter, as shown in FIG. 25, a conventional guide catheter 184, typically 7 French or 8 French in size, is positioned using first guide wire 178. Next, first guide wire 178 is removed leaving guide catheter 184 in position. This permits the distal portion of rapid exchange dilator assembly 116 to be passed through guide catheter 184 until expandable braid 184 extends past the distal end 186 of guide catheter 184 as shown in FIG. 26. Guide wire 150 is then extended to a chosen position relative to lesion 182 as shown in FIG. 27.

Dilator 144 is then removed by pulling on dilator proximal portion 148 while holding inner catheter fitting 138 and proximal end 156 of guide wire 150. Doing so leaves catheter 118 and guide wire 156 in place. This is possible because of the rapid exchange nature of assembly 116 provided by the passage of guide wire 150 externally of most of the length of dilator 144. The expandable braid 164 may then be extended to a use, material-directing state, such as the funnel shape shown in FIG. 28, to occlude blood flow to stop emboli from flowing downstream. Appropriate medical procedures, such as installing a stent or conducting angioplasty may then the accomplished.

RF Bonding

A further aspect of the invention relates to devices and methods for manufacturing thermoplastic materials. As the name thermoplastic implies, temperature can be used to shape, make, bend, mold, join, tip, bond, shape polymers (or metal to polymers) for use in production of components or other products. There is a plethora of techniques well known to those ordinarily skilled in the art of 'plastics manipulation' using heat to change the physical shape or properties of the plastic material. Injection, plug, insert, blow molding as well as heating tubes, hot water or other liquids, flame, heat guns, heat shrink tubing and other technologies too numerous to mention.

This aspect of the invention utilizes a constant temperature alloy that can be near instantly brought to a particular curie temperature. The present invention employs a temperature self regulating heater, with regulation of temperature being accomplished by employing a high density material such as a ferromagnetic, ferromagnetic or the like material having a Curie temperature at the desired maximum temperature of operation. The Curie point also known, as Curie temperature is the point/temperature at which a ferromagnetic material exhibits paramagnetism. Once this point is achieved, no additional energy is required to be put into the system and the temperature (Curie temperature) is maintained. This pre-chosen temperature can be set at a variety of temperatures depending on the chemical makeup of the ferromagnetic material and this choice can match the melt or near melt temperature of a particular plastic.

To be able to control a heating element for manufacturing/production of thermoplastic materials that does not require a temperature feedback loop to control the temperature of the particular element/die or other mechanism is desirable for several reasons. This aspect of the invention uses a ferromagnetic metal with low electrical conductivity that can be excited by a high frequency alternating current. By selecting dimensions and material parameters for the heating element, temperature regulation in a narrow range around the Curie temperature of the ferromagnetic material can be produced, despite thermal load (i.e. the melting or near melting of plastic).

This therefore does not require a conventional feedback loop (and required controllers and no necessary calibration) to control the temperature of the heating element. Specific ferromagnetic materials can be chosen that reach particular Curie temperatures, so that choosing a particular ferromagnetic material for the heating element with a particular Curie temperature for a particular application can choose a temperature. This allows a narrow range of temperatures to be achieved. Because the mechanism of use for the excitation of the ferromagnetic element is instantaneous with the alternating current source, the ferromagnetic material/element comes to its pre-destined Curie temperature very quickly. This instantaneous heat source is vital in forming thermoplastics quickly for efficient manufacturing conditions and a low cost manufacturing environment.

In brief, one embodiment of the present invention is particularly adapted to the manipulating thermoplastic materials with a die/element, mold ("heater") for manufacturing of components or other products in the manufacturing environment. By purchasing an 'off the shelf' RF generator/alternating current power source, one can excite a ferromagnetic heater to its Curie temperature and then by choosing a particular ferromagnetic alloy, different temperatures can be used for the heater in the manufacture/processing of particular thermoplastic materials.

Examples of ferromagnetic materials that exhibit different Curie temperatures when excited by an alternating radio frequency source is a metal alloy composed of approximately 36% nickel and the balance iron. Often referred to as Invar or Alloy 36 due to the nickel content. When alloy 36 is excited to it's Curie temperature, that temperature is controlled to a near temperature of ~230 degrees Fahrenheit. (~230° F. or 110° C.). Choosing alloy 42 (meaning ~42% nickel and the remaining iron), the Curie temperature achieved is ~380° F. or 193° C. For alloy 49, a temperature of ~475° F. or 246° C. For alloy 32, approximately 130° F. or 54° C. For alloy 34, 165° F. or 74° C. and for alloy 42-6, 290° F. or 143° C. So one can see that by choosing a particular ferromagnetic alloy, one can choose a particular melt or near melt temperature of a particular thermoplastic. Such ferromagnetic materials can be readily purchased from a wide variety of vendors including SCIENTIFIC ALLOYS in Westerly, R.I. ((401) 596-4947).

By connecting the power supply to the alloy though a trial and error approach the alloy became excited to its particular Curie temperature and was measured. These temperatures were delineated above. By machining different configurations in the heater element, the inventor was able to join thermoplastic materials with a variety of other materials (metals, thermoplastics, Thermoset polymers, fabrics and the like). Further, the inventor was able to form or program the thermoplastic material into what appears to be an endless variety of shapes and conditions for use.

Another aspect of the invention pertains to the engaging or blocking element. In the case where either element is somehow bonded to a tubular elongate member, this bond should be strong, but minimal in its overall size. In the case of using tubular mesh braid to attach the mechanism to the tube, often times an additional collar can be used to overlap both the tubular elongate member and the tubular mesh braid. However this aspect of the invention allows this 'joint' to be accomplished by joining the two components together without the addition of this collar, which is preferred because in such interventions any additional space required for 'joints' is a detriment to the overall functionality of the device. If collars or other assembly mechanisms are used either on the outside of the two materials or on the inside of the materials, either a larger hole/puncture into the body is required, which has an increased mortality/morbidity associated with it, or the internal diameter of the tubular elongate member is decreased, and hence the annular space is decreased and compromised because the interventionalist has less space to deliver other instruments or less space to remove matter from the body. Hence this aspect of the invention relates to the ability to 'connect' the tubular mesh braid to the tubular section of the catheter or device and at the same time minimizing any increased wall thickness due to collars or other assembly components. This can be accomplished in several ways.

In most cases the wall of the tubular elongate member is in the range of 0.002-0.015 inches (0.051-0.38 mm) thick, but more usually in the 0.004-0.006 (0.10-0.15 mm) inches thick range. Because of the way it is manufactured (with a Maypole type braider described below), the yarns used to manufacture the tubular mesh braid are usually fabricated from filaments in the range of 0.0001 to 0.005 inches (0.0025-0.13 mm) in diameter, but more usually in the 0.0015-0.003 inch (0.038-0.076 mm) diameter range. Because these individual yarns overlap, the wall thickness of the tubular mesh braid is usually double the thickness of the yarns used in its manufacture. The instant invention relates to the fact that the tubular mesh braid can be melted into the wall of the tubular elongate member with the use of heat. This is especially applicable when thermoplastic polymers are used with either one or both of the tubular mesh braid or the tubular elongate member. Using a die that conforms to the outside diameter of the tubular elongate member, both materials can be forced into the die when heat is applied and at the same time an inner mandril is placed inside the assembly that equals the internal diameter of the tubular elongate member. Using then the heat and force, the two components (the tubular mesh braid and the tubular elongate member) can meld into one unit thus minimizing the wall thickness of the two components thusly joined together. This heated die is usually accomplished using a glass or metal die. Heat is applied to the die in any of a number of ways know those normally skilled in the art including, but not limited to convection heating, electrical resistance heating, RF excitement of the metal to create heat, by merely blowing hot air over the die, etc.

A preferred embodiment of the instant invention utilizes an RF heater made from an RF power supply and a nickel iron alloy. By coordinating the radio-frequency (RF) energy with an appropriate nickel-iron alloy die, the metal alloy die can be excited by the radio-frequency energy, said excitement generating heat to the curie temperature of the alloy. The blend of nickel-iron alloy can be adjusted to reach different curie temperatures. This RF excitement is extremely fast which is critical to the efficacious manufacture of the devices. The dies can be made very small, that is with a very small amount of alloy, so that they not only heat up immediately, but they can be cooled quickly as well. Hence the less alloy in the die the faster the throughput in the manufacturing process. This technique is extremely repeatable as well due to the repeatability of the RF and the alloy interaction. These different temperatures are important as different temperatures are required for different heat bonding procedures (that are dependent both on the geometrical configuration of the heat bond as well as the materials used in the heat bond). Using this configuration, expanding mechanisms described above have been manufactured where in a preferred embodiment of the instant invention, NiTi (Nickel Titanium) tubular mesh braid with 0.003" (0.076 mm) individual yarns have been melded into the wall of PEBAX and polyurethane sheath tubes that have a wall thickness of 0.005-0.006" (0.13-0.15 mm) without compromising the internal or external diameters. (Have also melded 0.002" (0.051 mm) diameter yarns into both polyethylene and FEP). Because no extra material is used for this bond and no additional area is required to make this bond this is extremely important so as to allow more matter to be removed through the internal diameter (being optimized and not decreased or compromised) and the initial puncture into the body is minimal due to the minimized/optimized external diameter of the assembly as is further described below and herewith.

Braid Shapes with Heat Treating and Elastomer (Variable Vessel Diameter)

Another aspect of the invention pertains to a funnel manufactured using tubular mesh braid. In a preferred embodiment the funnel is made of the aforementioned tubular mesh braid. In particular, the yarns in the braid are made of metal and even more particularly, of Nickel Titanium alloy (NiTi). The preferred embodiment of this aspect of the invention is such that the tubular mesh braid is attached to an inner elongate member on the distal end and an outer elongate tubular member where the braid is attached at the proximal end. As the inner member is pulled in a retrograde/proximal direction, the braid is pulled inward so that it buckles, and folds inside itself like 'rolling a sock'. In this preferred embodiment, the braid takes on a funnel shape. In some cases the braid is covered with an inelastic or elastic membrane. This membrane can be applied by dipping, casting or spraying the braid with a dispersion including, but not limited to silicone or polyurethane. Alternatively, the membrane could be in the form of a tubular extrusion, which is then bonded with heat, or adhesive on the two (proximal and distal) ends of the braid where it is attached to the inner and outer elongate member. In the case of using the extrusion, this material includes, but is not limited to silicone, polyurethane, Chronoprene, polyethylene, C-Flex, etc Of particular importance to the design of the tubular mesh braid is the way in which the tubular mesh braid is formed. The preferred embodiment of the instant invention forms the tubular mesh braid on a maypole braider described below using 48 carriers of yarns made from NiTi on a 48 carrier or 96 carrier maypole braider, although in some instances it may be beneficial to use machines with more or fewer yarn carriers to adjust braid performance The NiTi yarns used are small in diameter, in the range of 0.001-0.005 inches (0.025-0.13 mm) in diameter, but more specifically 0.0015-0.0025 inches (0.038-0.064 mm) in diameter. They can be formed on a cylindrical mandril on the braider usually 5-6 mm in diameter or more preferred would be a conically shaped mandril to create a mesh braid with varying wire density and varying maximum expanded diameter to facilitate funnel deployment in lumens of various sizes. In fact, the mandril shape can be set to any axisymetric shape (for instance, a rotated parabolic arc) to further optimize the performance of the expanding member. In some cases, a non axisymmetric shaped mandril may be used as well, such as an elliptical cone or a pyramid. Further, the tubular mesh braid could be self-expanding where the yarns are programmed to be in the expanded funnel configuration. In this embodiment, the system could be constrained with an over sheath to keep in the smaller, contracted condition. Conversely, the inner and outer elongate members could be held in a tensile configuration with respect to one another so that the braid is in the un-expanded shape. When the tension is removed on the inner and out elongate member, the braid expands to the funnel configuration usually 1.5-7 mm in diameter, but more specifically from 2.5-5.5 mm. In addition, any combination of active or forced expansion and self-expansion may be used to optimize the design.

An additional aspect of the invention as it pertains to how the braid opens up into a funnel shape is the way that one 'programs' the tubular mesh braid. When the braid is pulled together so that it folds into itself to make the funnel shape, it may be important that there is a shape memory to the braid so that it folds in a particular way both to create the funnel, but also so that when it impinges on the wall of the vessel, it does so in a least traumatic fashion so as not too damage the intima of the vessel. The NiTi wires are preferably conditioned as to behave as super-elastic or pseudo-elastic material. In the case of expanding the funnel and trying to occlude blood, it is important is that the funnel has an outward radial force onto the vessel so that it in fact occludes the vessel and stops blood flow. This is important in the case of using the invention for 'proximal occlusion'.

Proximal occlusion, as the name indicates, is where the blood vessel is occluded proximally (up-stream) to where an intervention takes place (i.e. balloon angioplasty, stenting etc.). When the flow is stopped or reduced upstream to where the intervention is taking place, this prevents loose embolic material that may be dislodged from traveling downstream during the intervention. This dislodged emboli can be very dangerous and even cause stroke or in the worse case death.

By shaping the braid by braiding/winding it on a shaped mandril such as a tapered mandril or a mandril with various shapes on it, one can affect different characteristics of the tubular mesh braid. Braiding over a mandril tool of varying diameter with constant braiding machine speed varies the pitch of the braid and number of crossings over a given length of braid. Varying these parameters along a single braided component helps dictate where the braid will first collapse to then work as a "rolling sock". Further, heat-treating to modify the material or braid shape has positive effects as well. One may alter the material properties of the braid only in certain parts of it so that gradients of stiffness are present along the length of the braid. These changes in stiffness may be extremely rapid to incite buckling (funnel formation) at a particular location or actuation force, or may be gradual to prevent buckling and perhaps maintain radial force. This allows the braid to fold, and to form a funnel in a particular fashion as it is being deployed. Additionally, by heat-treating the braid in such a way so as to effect a geometrical change, the braid will tend to fold/roll in a desired way so that the deployed braid/funnel occludes properly with the desired amount of radial force and at the same time expands to a desired diameter and shape, as well as expanding in an a traumatic fashion. For instance, a shape step may be formed into the braid wire so that upon actuation, the distal portion of the braid extends radially out to make contact with the vessel wall creating a deployment shape that is conducive to braid buckling. The size and geometry of this step can be adjusted to a particular application. Any sort of geometrical change can be formed during the actual braiding process, or through secondary mechanical or thermal means at any time in the manufacturing process.

Another secondary operation that may be used to improve the performance of the expanding braid section is the inversion of the braid. By turning the mesh braid "inside out", it exhibits properties different from those of a "right side out" braid section. These differences may be greatest when the braid wire material is nitinol, and it is inverted after heat treatment, but some desirable performance characteristics may be present when using other braid wire materials, such as stainless steel, or when inverting the braid without heat treatment.

As previously mentioned, the overall profile of the device is of critical importance so that the physician can use the smallest incision necessary while still having the largest size lumen available for other therapeutic devices. With this in mind, another preferred design embodiment employs a braided shaft with an integral expanding braid section at the distal end. The braided shaft can be constructed with the desired wall thickness (specifically between 0.002" and 0.015" (0.051-0.38 mm)) and stiffness characteristics, and the expanding braid portions can be formed by simply continuing the braid beyond the shaft's polymer components. This process eliminates any secondary bond between the expanding braid and the shaft, and simultaneously creates a device that is stronger and more durable. One of many possible manufacturing methods entails placing the polymeric inner liner of the braided shaft on a mandril, and loading the mandril and liner assembly through the maypole braider. The mandril may have a distal shaped section that can be used to form the desired expanding braid shape. Braiding is continued over the expanding braid section of the mandrel, and heat-treated if necessary. The outer polymeric component, or components are then laminated over the braided shaft section.

Using different coverings over the tubular mesh braid as well can modify all of these characteristics. For example, one embodiment of the invention would be a thermoplastic extrusion that has variable wall thickness. The wall thickness of the membrane may be varied along the length of the braid to have one or more zones of increased or decreased resistance to actuation (expansion), or zones of increased durability. These variable wall thicknesses will also allow the thinnest sections of the tubular mesh braid to expand first or to a larger overall diameter in contrast with zones having thicker membrane thicknesses. The adjustment of the order or degree of actuation of various sections along the length of the expanding braid will allow the device to achieve an optimum balance of actuation reliability, actuation force, and radial force exerted on the vessel wall. Generally, an extruder can extrude to approximately 0.003" (0.076_mm) wall thickness of the tubing. In the manufacturing process, the technician can 'pre-dilate' the extrusion (all or part) and in doing so can controllably change and vary the expansion properties and wall thickness to achieve better device performance as compared to pre-dilated membranes. The easiest way to accomplish this 'pre-dilation' is to apply air pressure to the extrusion when it is sealed off at one end. Most thermoplastic elastomers used for this application have elastic modulus characteristics from 300-1500%, but more particularly from 600-1000%. Examples such as Chronoprene, polyurethane, C-Flex, latex, polyisoprene and silicone exhibit these properties.

Figure 29:
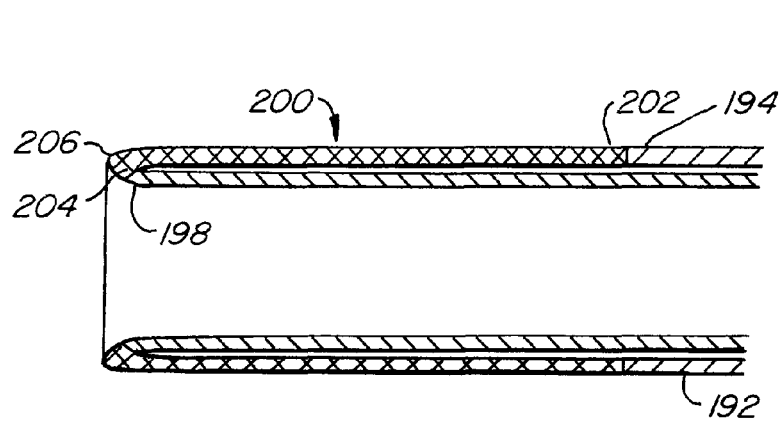
FIGS. 29 and 30 are cross sectional views of the distal ends of two embodiments of a funnel catheter.
Figure 30:
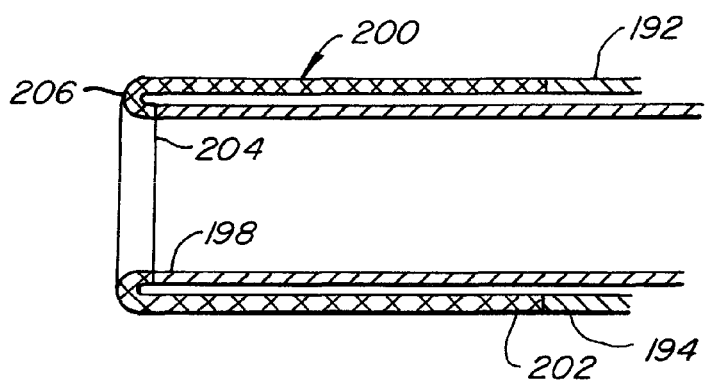
Figure 31:
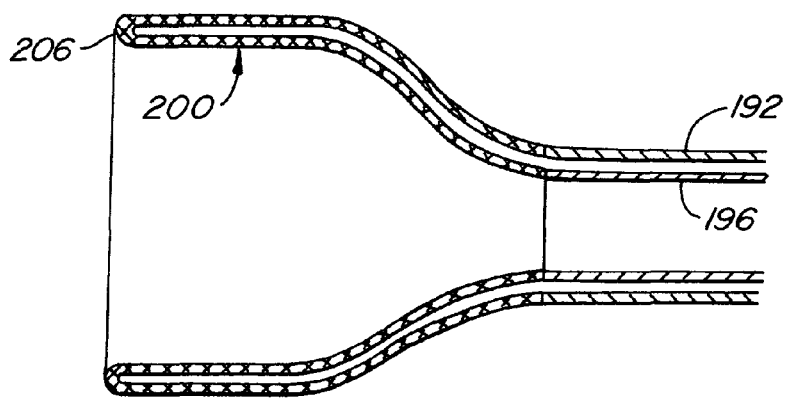
FIG. 31 shows the funnel catheter of FIG. 30 in a radially expanded state.
Figure 32:
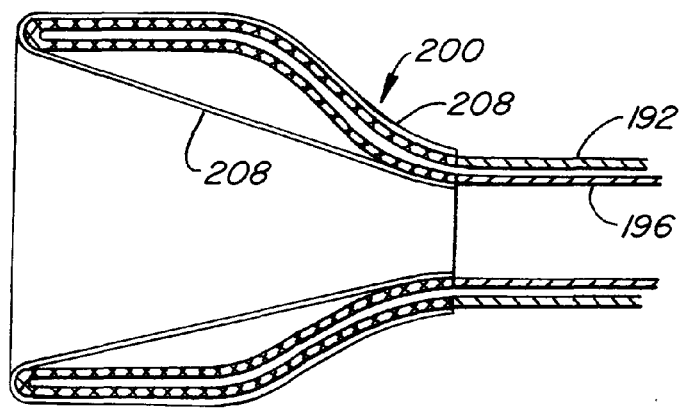
FIG. 32 shows an alternative embodiment of the funnel catheter of FIG. 31 with an elastic film on the outer surface.
Figure 33:
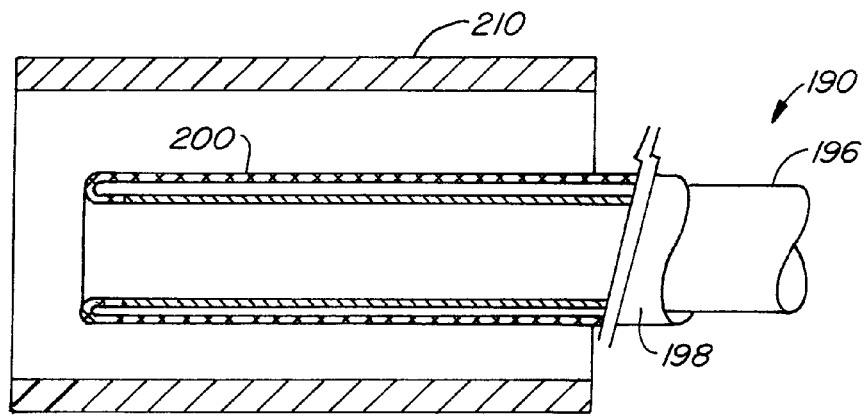
FIGS. 33 and 34 show the placement and use of the funnel catheter of FIG. 30 within a vessel.
Figure 34:
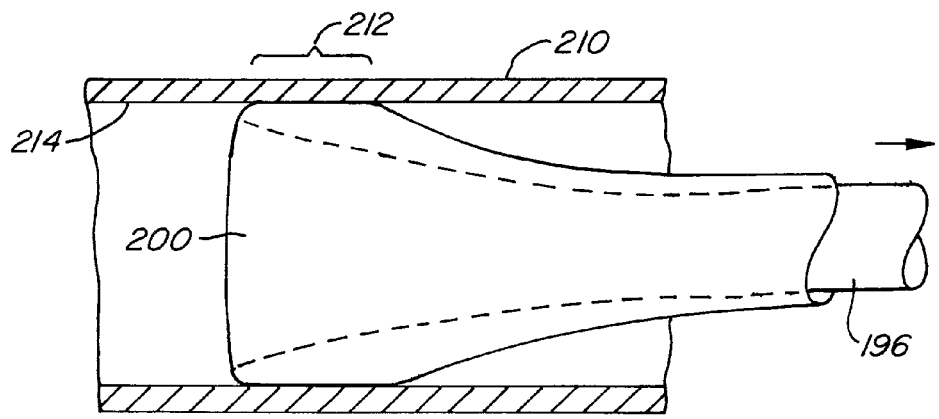

FIG. 29 illustrates the distal end of a funnel catheter 190 including an outer tube 192 having a distal tip 194, an inner tube 196 having a distal tip 198 and a tubular sleeve 200 having first and second ends 202, 204 secured to distal tips 194, 196. Tubular sleeve 200 is shown in its radially contracted, deployment state. It is important that tubular sleeve 200 have a generally U-shaped, direction-reversing region 206 so that when first and second ends 202, 204 move toward one another from their positions of FIG. 29, sleeve 200 moves to a distally opening, radially expanded, use state, such as shown in FIG. 31. FIG. 30 illustrates an alternative embodiment of funnel catheter 190 in which region 206 in the deployment state has a more pronounced U-shape than the embodiment of FIG. 29. FIG. 31 illustrates funnel catheter 190 in a radially expanded use state. Funnel catheter 190 is typically used to seal the interior of a graft, blood vessel or other hollow body structure so that the material from which funnel catheter 200 is made is typically substantially impervious to fluid flow. While tubular sleeve 200 is preferably a braided tubular sleeve impregnated with a flexible polymer material, sleeve 200 maybe constructed in other ways. FIG. 32 illustrates a tubular sleeve 200 and which the fluid flow barrier is provided as a flexible, elastic film 208 on the outside of tubular sleeve 200. FIGS. 33 and 34 illustrate placement and use of funnel catheter 190 within a vessel 210. Pulling inner tube 196 relative to outer tube 198 causes tubular sleeve 200 to create a funnel-type material-directing element with a substantial portion 212 contacting the inner wall 214 of vessel 210. Funnel catheter 190 can be made to provide a sufficiently high level of force to inner wall 214 over a relatively large contact area to provide a good seal while minimizing risk of tissue damage.

Other methods to achieve a funnel catheter that reliably creates a distally directed open funnel end will be described below with reference to FIGS. 35-51. In general, the different techniques include adjusting the taper angles at the distal and proximal portions of the mandril, selectively applying material to one or both of the distal and proximal portions of the braided material, and changing the pic count between the distal and proximal portions. While in practice more than one of these techniques may be used to construct a working device, the different techniques will be discussed below with regard to specific embodiments incorporating a single technique.

Figure 35:
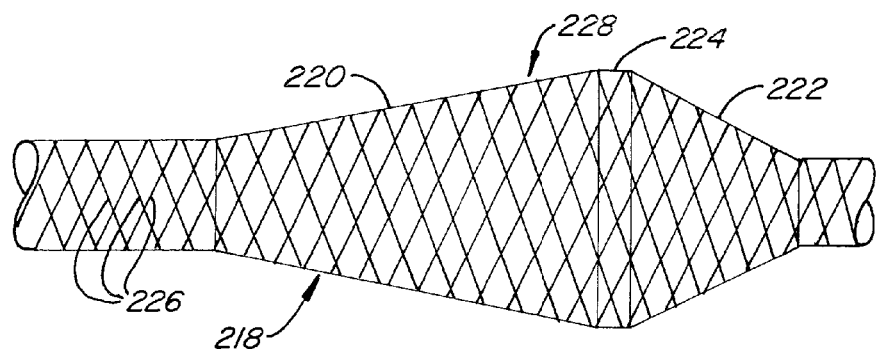
FIG. 35 illustrates a mandril having tapered proximal and distal portions wound in a braided fashion to create a braided structure.

FIG. 35 illustrates a mandril 218 having a proximal taper portion 220 and a distal taper portion 222 connected by a central, typically constant diameter, portion 224. Mandril 218 is wound in a braided fashion with braid winding 226 to create a braided structure 228. Proximal taper portion 220 has a more gradual paper than distal taper portion 222, that is $\theta_1 > \theta_2$. In the embodiment of FIG. 35, the pic count, that is the number of crossings of braid windings 226 per unit length, is constant along the entire length of mandril 218. A membrane, not shown, may be used with braided structure 228. The membrane maybe incorporated into, lie on top of or be located within braided structure 228. The membrane may be chosen to halt all fluid flow therethrough or only prevent the passage of particles having a minimum size. Braided structure 228 is then removed from mandril 218 and mounted to outer and inner tubes 230, 232 to create a funnel catheter 234 with a tubular braided sleeve 236. See FIGS. 36-39.

The proximal end 238 of sleeve 236 is secured to a first position 240 on outer tube 230 and the distal end 242 of sleeve 236 is secured to a second position 244 on inner tube 232. The greater taper at distal taper portion 222, $\theta_1 > \theta_2$, helps to ensure that the distal portion 246 of sleeve 236 buckles before the proximal portion 248 of the sleeve. See FIGS. 38 and 39. While inner tube 232 is shown extending distally an indeterminate distance, it may be, for example, terminated at or near second position 244 on inner tube 232.

Figure 36:
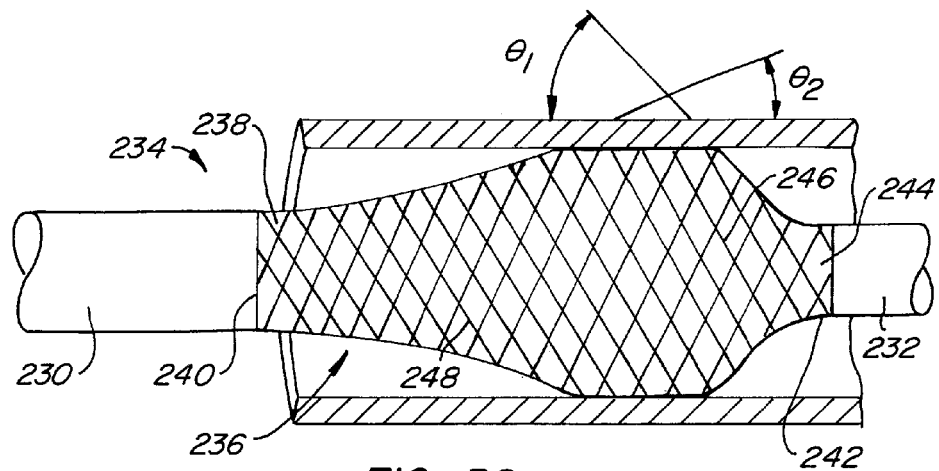
FIGS. 36-39 show the braided structure of FIG. 35 used to make a funnel catheter, the braided structure being in an expanded diameter state in larger diameter and smaller diameter vessels.

FIG. 36 illustrates tubular braided sleeve 236 in a larger diameter vessel 250. As the vessel diameter is increased, the contact length of the braid is reduced. This makes the distal/proximal competition more important (the distal portion 246 of sleeve 236 must buckle first) because friction between the device and the vessel wall does not significantly help to create the distal funnel. With smaller diameter vessels 254, see FIGS. 37 and 39, outer tube 230 is typically held fixed while inner tube 232 is pulled proximally. Friction between braided sleeve 236 and vessel 254 helps to hold the proximal, outer tube 230 fixed while motion at the distal end 242 of sleeve 236 makes the distal portion 246 of sleeve 236 collapse. With large vessels, see FIGS. 36 and 38, the friction is less than with smaller diameter vessels to increase the possibility that the whole tubular braided sleeve 236 can shift (slide) potentially causing proximal portion 248 of braided sleeve 236 to buckle. When the pic count is constant or generally constant as in the embodiment of FIGS. 35-39, is very important that the difference in the taper angles provide the necessary bias to ensure that distal portion 246 always wants to yield first (that is, before proximal portion 248) and collapse into a funnel shape as illustrated in FIG. 38.

Figure 37:
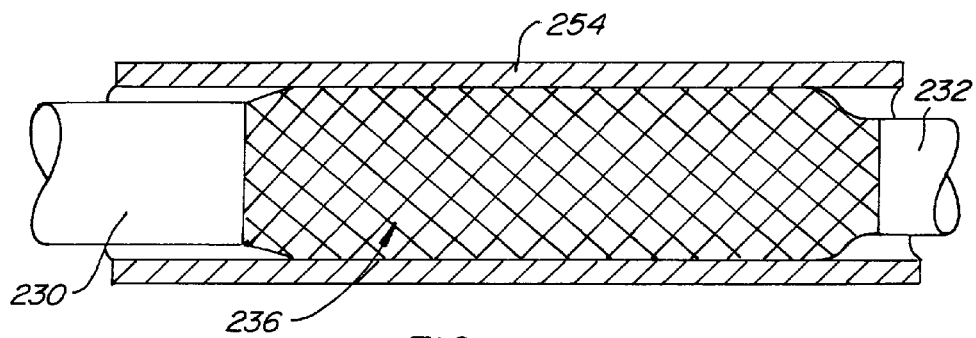
Figure 38:
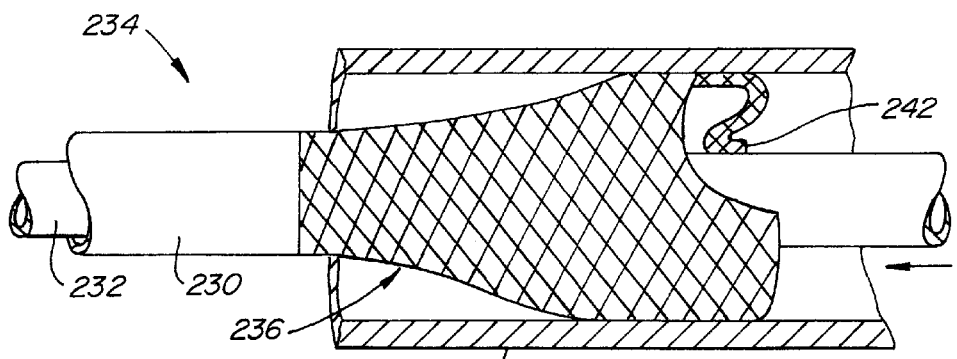
Figure 39:
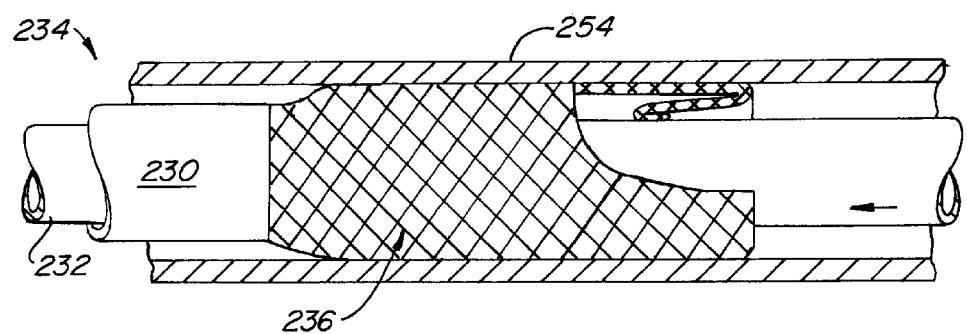

FIGS. 37 and 39 illustrate tubular braided sleeve 236, having a constant pic count, in smaller diameter vessel 254. In this situation, much of the braided sleeve 236 comes in contact with the vessel wall. Providing an appropriate difference in taper angles with $\theta_1 > \theta_2$, ensures that distal portion 246 buckles before proximal portion 248.

Figure 40:
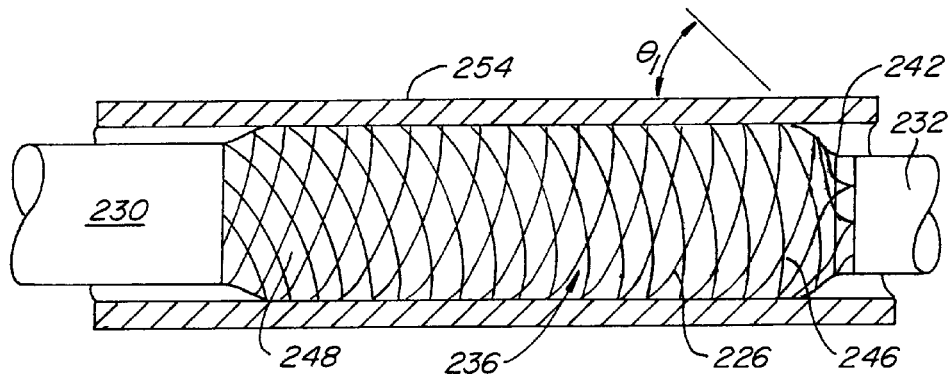
FIG. 40 shows an alternative to the embodiment of FIG. 37.

FIG. 40 illustrates an alternative embodiment of a constant pic count tubular braided sleeve 236 designed to ensure that distal portion 246 buckles before proximal portion 248. Braid windings 226, typically made of NiTi, at distal end 242 of sleeve 236 are heat-treated to make an abrupt diameter change after braiding. This creates a weak geometry in the shape at this position so that with the application of a small compressive load, sleeve 236 will buckle in the region of distal end 242. This effect is made more effective with increased distal end taper angle $\theta_1$ and a reduced radius at this position. Other methods for creating a sharp step shape set in the braid after weaving may also be used.

Figure 41:
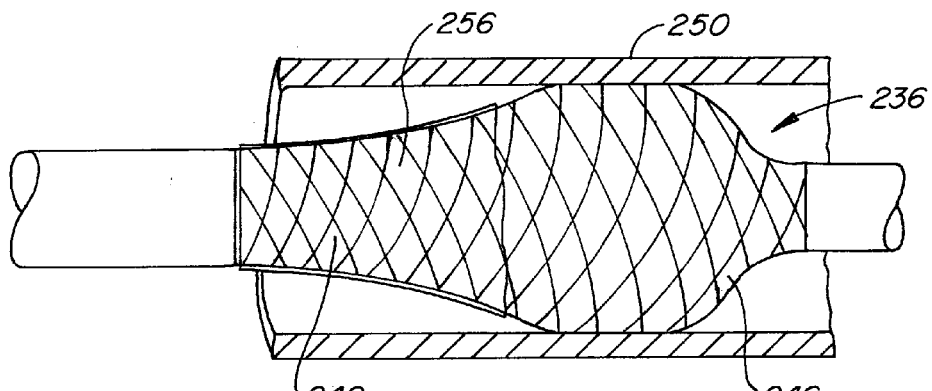
FIGS. 41 and 42 show two different embodiments to the embodiment of FIG. 36.

FIG. 41 illustrates a further alternative embodiment of a constant pic count tubular braided sleeve 236 designed to ensure that distal portion 246 buckles before proximal portion 248. A part of proximal portion 248 is coated with a polymer 256, which is typically somewhat elastic, to limit expansion of proximal portion 248 so it cannot fully expand and buckle. The remainder of sleeve 236 is uncoated to promote buckling at distal portion 246.

Figure 42:
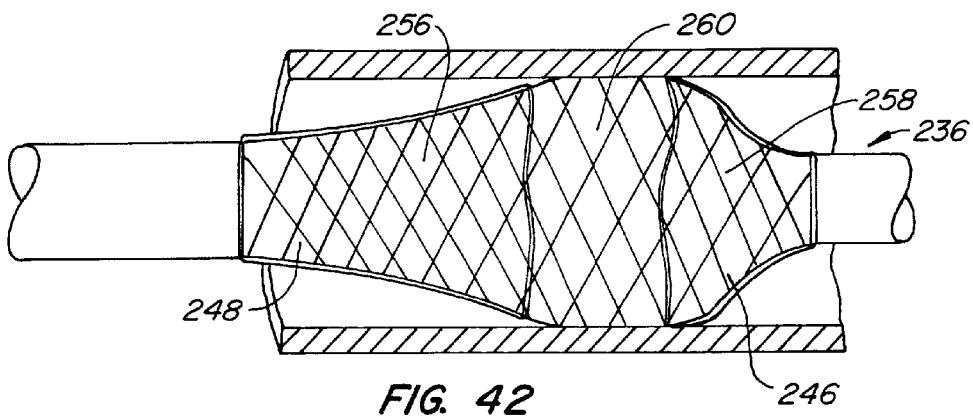

FIG. 42 similar to FIG. 41 accuses a relatively stiff, relatively stretch resistant polymer coating 256 at proximal portion 248 and a relatively soft, relatively easily stretched polymer coating 258 at distal portion 246. Polymer coating 256 keeps the proximal braid from fully expanding and buckling. The soft distal covering provided by polymer coating 258 allows full expansion, buckling and a good hydraulic seal to enable aspiration through the center of this device. If desired, the central portion 260 of sleeve 236 may also be covered with the same, soft, easily stretchable polymer 258 for a different polymer that may be even more easily stretched than polymer 258.

Figure 43:
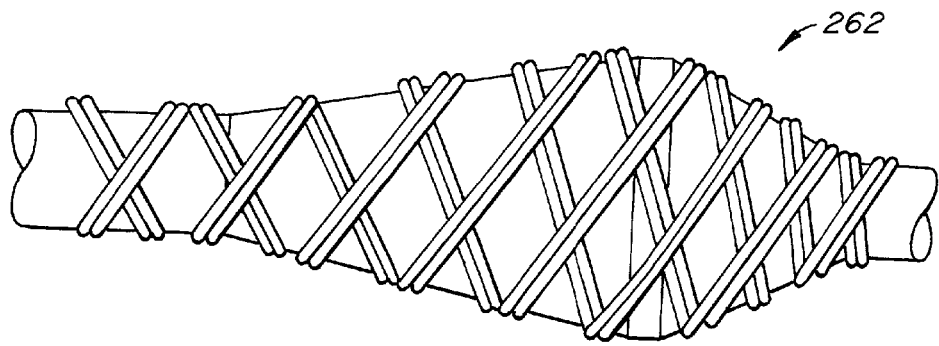
FIGS. 43 and 44 show two additional embodiments of the braided structure of FIG. 35.
Figure 44:
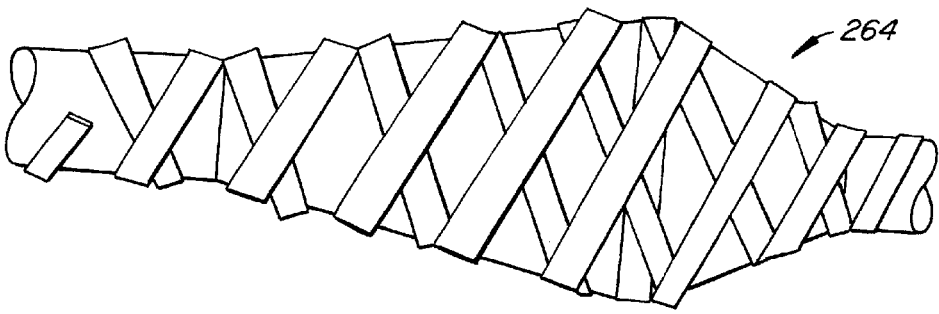

FIGS. 43 and 44 illustrate alternatives to the braided structure 228 of FIG. 35. FIG. 43 shows a double wire braided structure 262 having a constant pic count. The double wire can be round or ribbon coming off 1 or 2 spools. More wires such as 2, 3, 4 or 5 can be stranded together to allow low bending forces with high hoop strength. This will allow the braid to have great composite strength with the ability to shift to a low profile and be flexible in a catheter. FIG. 44 illustrates a constant pic count ribbon band braided structure 264. Structure 264 is typically made of NiTi, stainless steel, titanium, a polymer or tungsten in sizes ranging from 0.0003 to 0.005 inch thick by 0.001 to 0.030 inch wide (0.0076 to 0.13 mm thick by 0.025 to 0.76 mm wide). One example could be 0.0005 inch thick by 0.003 inch wide (0.013 mm thick by 0.076 mm wide).

Figure 45:
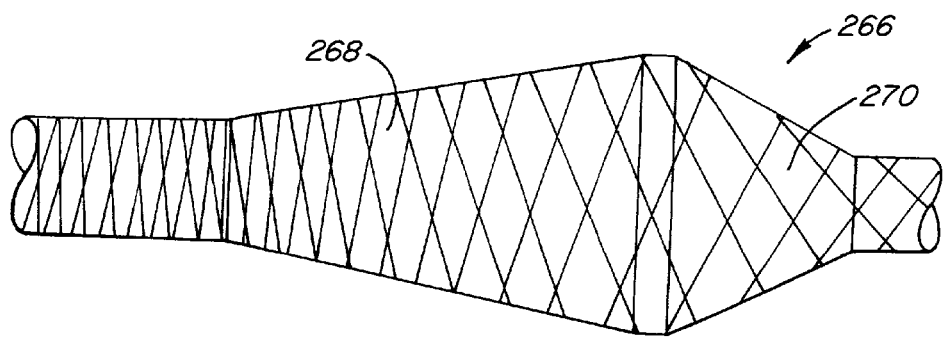
FIGS. 45 and 46 show an alternative winding pattern to create windings more closely spaced at the proximal portion than at the distal portion.
Figure 46:
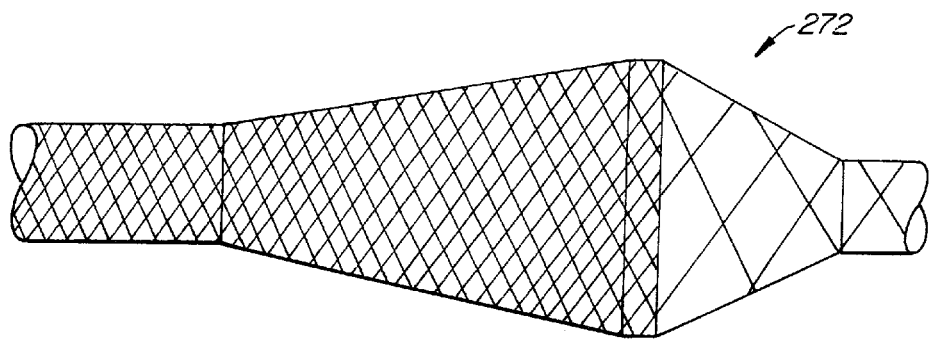

FIG. 45 shows an alternative to the constant pic count embodiment of FIG. 35. Braided structure 266 has a variable pic count with a higher pic count along the proximal taper portion 268 and a lesser pic count along the distal taper portion 270. Braided structure 266 can be produced by gradually speeding up the "take up" reel on the braids while running the wire spools at a constant speed. This design can be tuned to make distal taper portion 270 weaker with large openings (distance between wire crossings) so it buckles into a tunnel before the proximal taper portion 268. This design can accommodate relatively large radial expansion to cover a large range of vessel sizes. Removing some of the wire strands to create braided structure 272 as shown in FIG. 46 can create a similar effect, that is forcing distal buckling before proximal buckling. The wires are braided a distance over mandril 218, every other wire is cut (as an example) and then the braiding is continued with a lower pic count and fewer number of wires.

Figure 47:
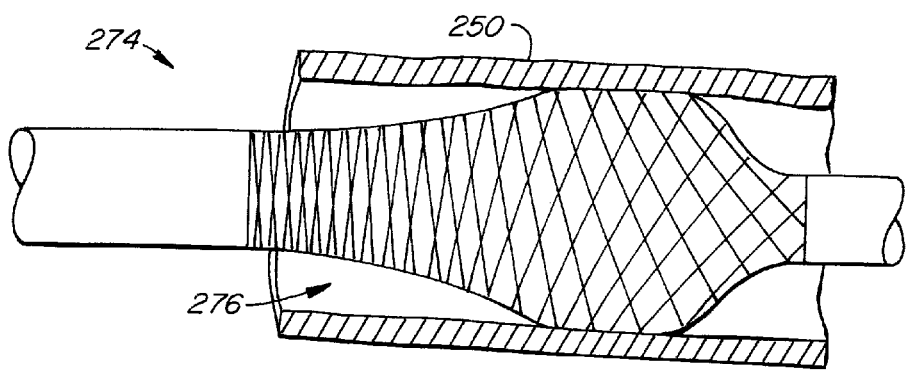
FIGS. 47 and 48 are similar to FIGS. 36 and 37 but use the winding pattern of FIG. 45.
Figure 48:
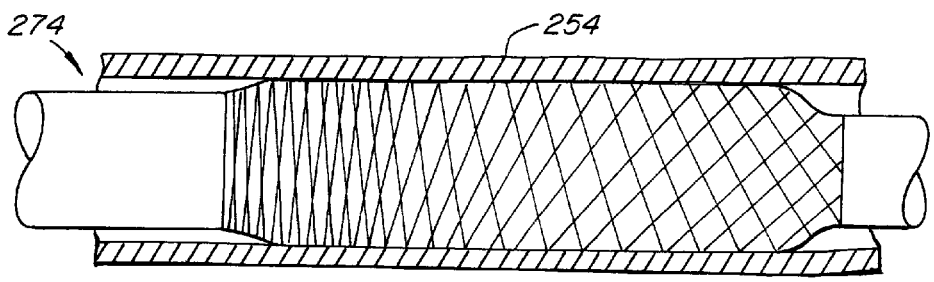

A variable pic count funnel catheter 274 is shown in FIG. 47 and includes a tubular braided sleeve 276 made from braided structure 266 of FIG. 45. Variable pic funnel catheter 274 is shown partially expanded in a larger diameter vessel 250. Proximal taper portion 268 of braided structure 266 can fully expand but the taper is so gradual that it behaves more coil bound. Distal braid portion 270 must have a sufficiently low pic count to be sufficiently weak to yield first. Funnel catheter 274 is shown in FIG. 48 within a smaller diameter vessel 254. In this case it is beneficial to have a low pic count distally so distal taper portion 270 is weaker than proximal taper portion 268 and tends to buckle under compressive load. This works well as long as the proximal end cannot fully expand in the vessel diameter. High pic counts that cannot fully expand tend to lock up with lots of support (closely spaced supporting crossings).

Figure 49:
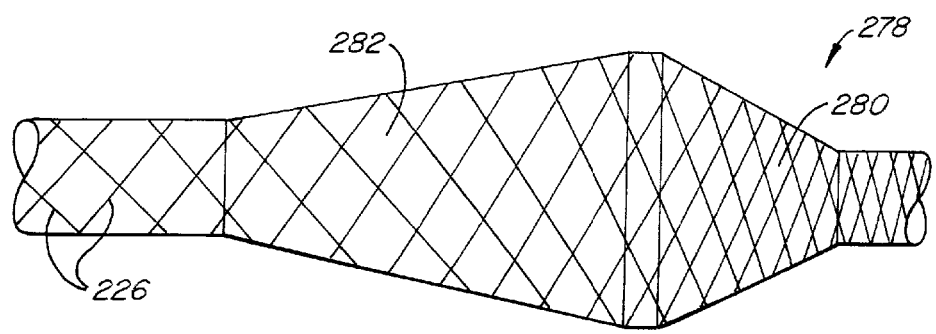
FIG. 49 shows an alternative winding pattern to create windings more closely spaced at the distal portion than at the proximal portion.
Figure 50:
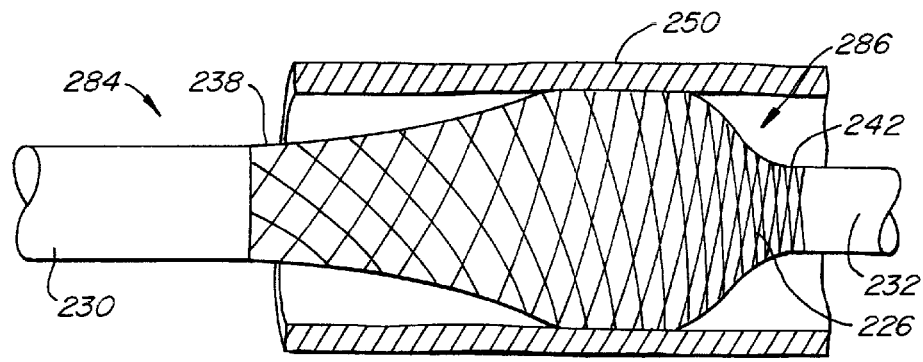
FIGS. 50 and 51 are similar to FIGS. 47 and 48 but use the winding pattern of FIG. 49.
Figure 51:
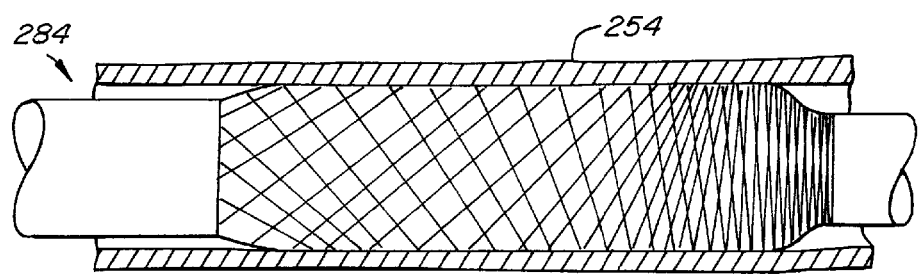

The variable pic count braided structure 278 of FIG. 49 reverses the winding pattern of braided structure 266 of FIG. 45 to provide a higher pic count at distal taper portion 280 than at proximal taper portion 282. This can be tuned to allow the smallest section of distal taper portion 280 to fully expand before hitting the vessel wall, or even the smallest anticipated vessel size. At full expansion, the windings 226 of variable pic count funnel catheter 284, see FIGS. 50 and 51, at distal end 242 are pushed into nearly a coil bound hoop path that can easily buckle to create the distal funnel before the proximal end buckles. After the initial buckling, the distal funnel end can grow like a rolling sock as distal and proximal ends 242, 230 move towards one another to enlarge the funnel opening. FIG. 48 illustrates funnel catheter 284 within smaller diameter vessel 252. The high pic count at the distal portion of braided structure 286 causes the distal portion to buckle first as long as it can fully expand in the vessel. The higher the pic count of a section of tubular braided structure 278 on the mandril, the less that section will expand under axial compression. The section of structure 278 having a very high pic count will remain almost fully expanded in the low profile catheter. After actuating, the very high pic count section will become hoop-like and buckle.

A Balloon that is a Funnel

Another aspect of the invention relates to a funnel shaped balloon. This is easily accomplished by shaping the balloon in such a way so that when it is expanded by gas or liquid, it expands in the shape of a funnel. This can be accomplished in several ways. In the case of making a balloon from a thermoplastic material including, but not limited to Chronoprene, polyurethane, C-Flex, Latex rubber, etc., these can be dipped, cast, sprayed or otherwise coated on a mandril that is in the shape of a funnel, or alternatively, they can be an extrusion that is then placed on a mandril that is the shape of a funnel and then by applying heat, the polymer will take the shape of the mandril. Even further, the extrusion can be placed inside a mold that is the shape of the funnel and with the addition of heat and then applying air pressure to the inside of the extrusion, the polymer will expand to the shape of the internal configuration of the mold cavity. After heat is removed from either of the above-mentioned processes and the system is allowed to cool, the result is a balloon that is in the shape of a funnel.

Alternatively the polymer could be made of an inelastic material including, but not limited to polyethylene, PET, HDPE, etc. These shapes can be accomplished in a similar manner stated above. Further because they are inelastic in nature they can be plastically deformed to create the shape of the funnel.

Figure 52:
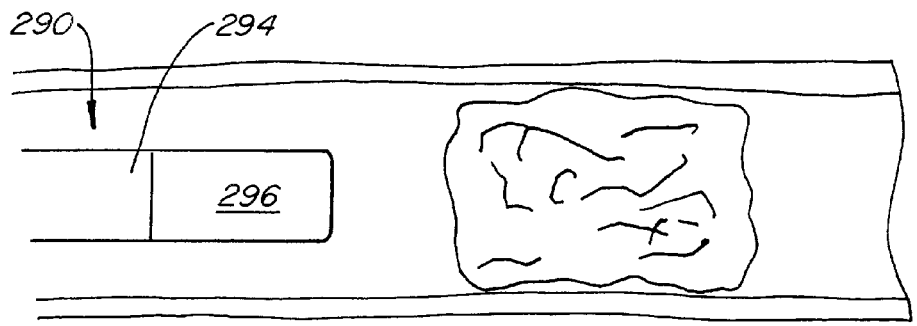
FIGS. 52 and 53 show a balloon funnel catheter within a vessel near an obstruction in radially expanded and radially contracted states.
Figure 53:
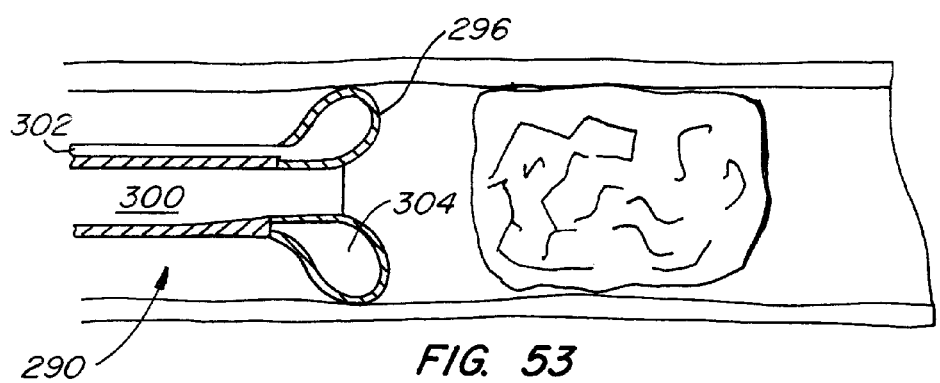
Figure 54:
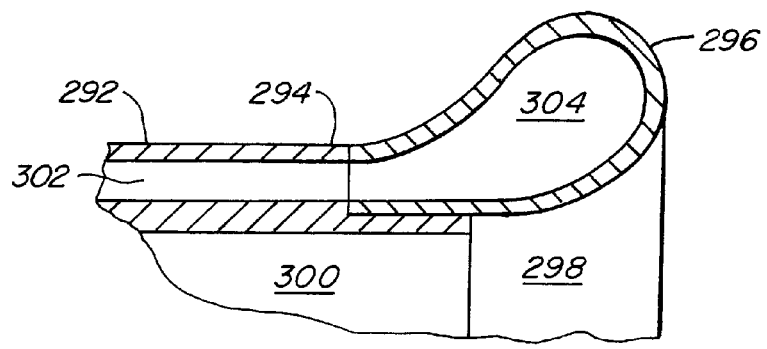
FIG. 54 is an enlarged partial cross sectional view of the balloon of FIG. 53.
Figure 55:
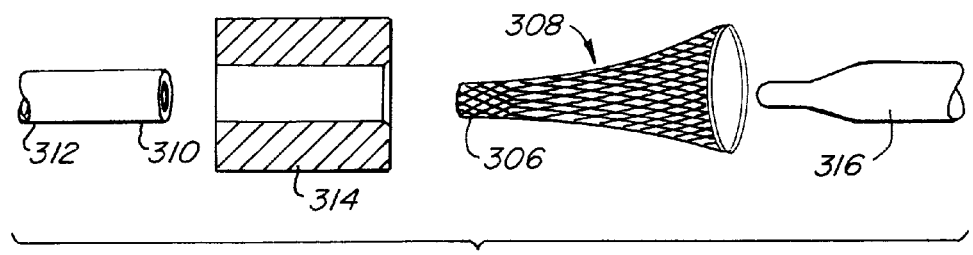
FIGS. 55-58 illustrate securing an end of a tubular braid within the end portion of a tube using a heated tool and a mandril.

A balloon funnel catheter 290 is shown in FIGS. 52-54. Catheter 290 includes a shaft 292 having a distal end 294 to which an annular balloon 296 is secured. Balloon 296 extends past distal end 294. Balloon 296 defines a central open region 298 aligned with a main lumen 300 of shaft 292. Shaft 292 also includes inflation lumen 302 opening into the interior 304 of balloon 296. Balloon 296 moves between the uninflated, radially contracted state of FIG. 52 and the inflated, radially expanded state of FIGS. 53 and 54. Open region 298 is funnel shaped when balloon 296 is in the inflated, radially expanded state.

Expanding the Elastomer with the Braid and Applying Heat

The interaction of a braid and a membrane is obviously critical and can be optimized to provide various funnel shapes and properties. Additionally, the elastomer may be free from attachment to the expanding braid over one or more sections but still bonded proximally and distally to the outer member, and inner member, respectively. This construction has the benefit of eliminating any protrusions created by bonds or braid geometries. More specifically, it is preferred to use this technique on the distal end of the expanding braid section, creating a smooth, uninterrupted funnel shape. This smooth shape may improve fluid dynamics, perhaps by eliminating eddy currents, and allow for more complete aspiration of emboli.

It is desirable to create a membrane that is firmly attached to the braid over a section, yet is free from attachment in another section. In this manner the braid can be held in the desired shape (may be final deployed shape or any other intermediate position), and the membrane is placed over the braid. This assembly can then be placed into a heated mold, or other apparatus to heat the membrane, allowing it to flow and meld with the braid wires. Insulation may be placed in the mold to prevent the heating of certain sections of the membrane, thus keeping the membrane free from the braid.

Another aspect of the invention relates to a configuration where the polymer is shaped with the use of heat in conjunction with the expanding braid. For example, a thermoplastic elastomer (including, but not limited to polyurethane, C-Flex, Chronoprene, etc.) could be applied to the tubular mesh braid (this application could be sprayed, cast dipped, or an extrusion that lies over the braid) and then the tubular mesh braid is actuated so that it expands in any desired shape (including but not limited to funnel, disc-shape, ovaloid, spherical, conical or any other desired shape). In this case, the addition of heat would be advantageous because it would allow the polymer to form into the desired shape. This could be accomplished during and/or after the tubular mesh braid is expanded. Further, since the interaction of the braid and the membrane is obviously critical it may be necessary to control this interaction by bonding the braid to the membrane along its entire length or in discrete sections. The elastomer may be free from attachment to the expanding braid over one or more sections but still bonded proximally and distally to the outer member, and inner member, respectively. This construction has the benefit of eliminating any protrusions created by bonds or braid geometries. More specifically, a preferred embodiment is to use this technique on the distal end of the expanding braid section, creating a smooth, uninterrupted funnel shape. This smooth shape may improve fluid dynamics, perhaps by eliminating eddy currents, and allow for more complete aspiration of emboli.

In some situations it may be desirable to create a membrane that is firmly attached to the braid over a section, yet is free from attachment in another section. The braid can be held in the desired shape (may be final deployed shape or any other undeployed or intermediate position), and the membrane is placed over the braid. This assembly can then be placed into a heated mold, or other apparatus to heat the membrane, allowing it to flow and meld with the braid wires. Insulation (PTFE tubing, for example) may be placed in the mold to prevent the heating of certain sections of the membrane, thus keeping the membrane free from the braid. This forming method is viable for use with any thermoplastic braid (elastic or inelastic).

Additionally in the case of inelastic polymers, the tubular mesh braid could be used to actually plastically deform the inelastic polymer. In this case it may be advantageous to use tubular mesh braid that has a greater outward radial force so that the plastic deformation may be accomplished. This increased radial force of the tubular mesh braid could be accomplished by using yarns in the braid that are larger and stronger or both. In both instances of using the tubular mesh braid as a 'tool' for creating the shape of the elastomers, air pressure and heat may be used to aid with the process. In the case of the aforementioned embodiment, where one is creating a balloon in the shape of a funnel, disc, ovaloid, cone, etc, this braid could be used as a tool as well.

Figure 56:
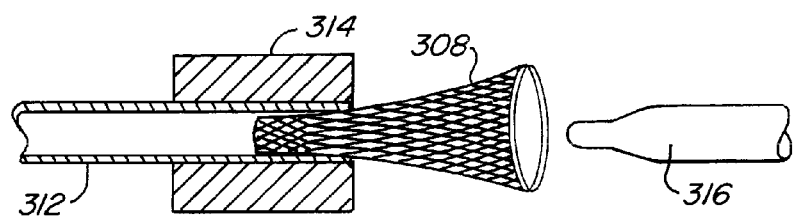
Figure 57:
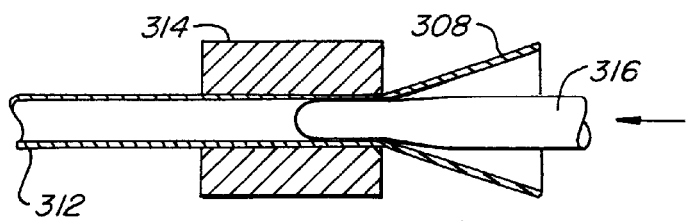
Figure 58:
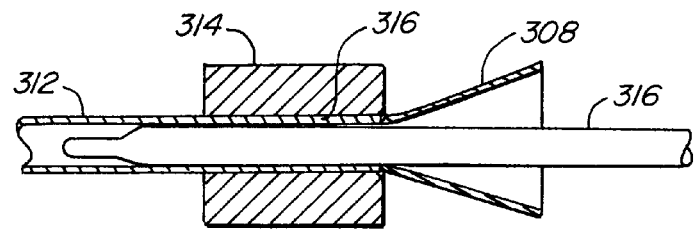

A method for securing an end 306 of a tubular braid 308 to a softenable end portion 310 of a tube 312 is illustrated in FIGS. 55-58. End portion 310 is inserted into a heated tool 314 and end 306 of tubular braid 308 is placed within the open end portion 310 as shown in FIG. 56. Heated tool 314 causes end portion 310 to soften sufficiently so that when a mandril 316 is inserted through tubular braid 308 and into the interior of heated tool 314 as shown in FIGS. 57 and 58, first end 306 of tubular braid 308 is driven into softenable end portion 310 to create a tube/braid material matrix 316. The resulting bond creates a strong, intimate bond with at most an insubstantial change in either the outside or inside diameter of tube 312.

Heated tool 314 can be heated in a variety of conventional or unconventional manners, including electrical resistance heating and RF heating. While sensors and feedback loops may be used to keep heated tool 314 at a desired temperature, heated tool 314 may be made of a material having a Curie temperature at the desired operational temperature to maintain the tool at the desired operational temperature.

Figure 59:
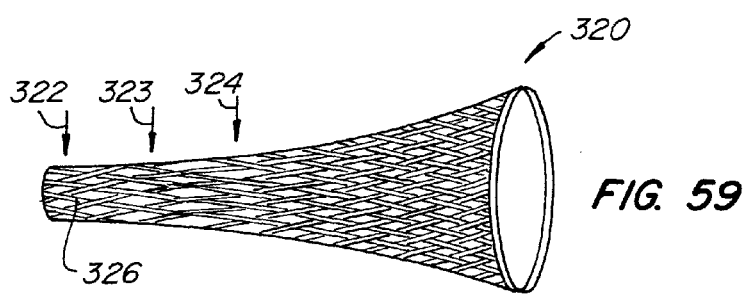
FIGS. 59 and 60 illustrate two embodiments of a radially expandable and contractible braided device in which the expansion is controlled by the application of a material over portions of their lengths.
Figure 60:
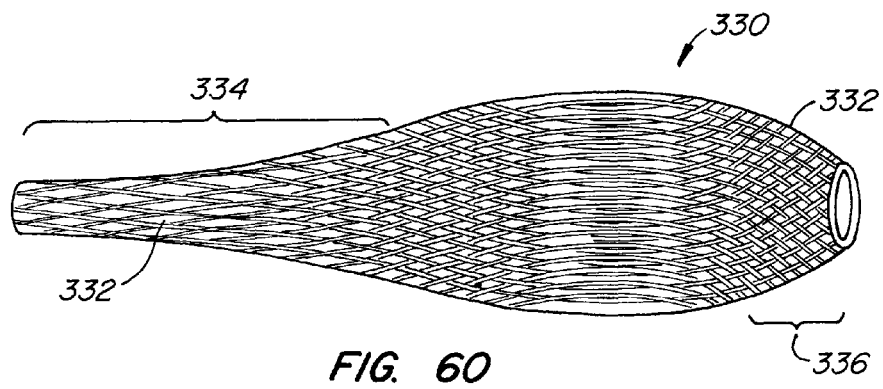

The shape of a radially expandable and contractible tubular device can be controlled in a manner indicated in FIGS. 59 and 60. FIG. 59 illustrates a funnel shaped radially expandable and contractible tubular braid device 320. Device 320 has different cross-sectional dimensions at different positions, such as positions 322, 323, 324 along its length, when in a radially expanded condition. Device 320 may be radially expandable or contractible naturally or with the aid of an external force or stimulus, such as heating or mechanical manipulation. By varying the thickness of impregnating material 326, the resistance to radially expansion can be adjusted to achieve the desired shape. For example, device 320 has been made with material 326 thickest at position 322 with a gradual decrease in thickness at positions 323 and 324, and with no material past position 324. FIG. 60 illustrates a tubular braid device 330 having elastomeric material 332 along a proximal portion 334 and along a distal portion 335 of the device to create the expanded diameter bowling pin shape for device 330. While the application of material 326, 332 may result in a material having a varying thickness over at least part of its length, the application may result in a material having a constant thickness or a finite number of thicknesses. For example, a number of bands of material, having the same or different thicknesses and having the same or different axial spacings, may be applied to the braided material. Also, different materials having the same or different stretch resistant characteristics may be used. The material may be a generally elastic material or a generally inelastic material or a combination thereof. While it is generally preferred to use an impregnating material 326, an appropriate radial expansion-inhibiting material may be applied on the outer surface of the braid or, if properly attached, over the inner surface of the braid.

Figure 61:
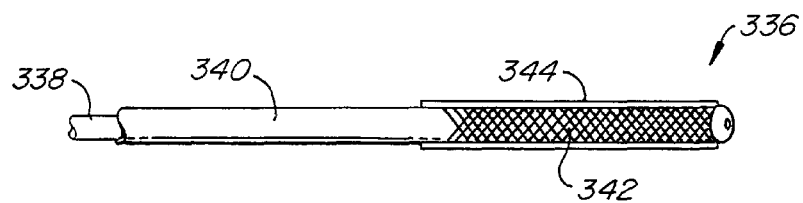
FIGS. 61 and 62 illustrate the use of a radially expandable device to impart a shape to a membrane.
Figure 62:
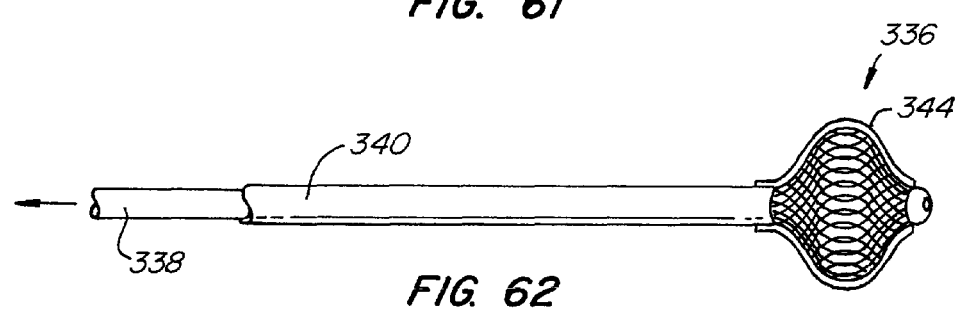

In some cases it may be desired to impart a shape to a thermoplastic membrane which can then be used in conjunction with a radially expandable element, such as a tubular braid element or a malecot element, to help the radially expandable element achieve a desired radially expanded shape. FIGS. 61 and 62 show the use of a radially expandable device 336 having inner and outer tubes 338, 340 and a tubular braid element 342 at the distal ends of tubes 338, 340. Device 336 is a tool and could be replaced by other tools, such as a malecot device, which would serve the same function. A thermoplastic membrane 344 is positioned over tubular braid element 342 and element 342 is radially expanded as shown in FIG. 62. A set is imparted to thermoplastic membrane 344, typically by a heating and cooling cycle; the method of imparting the set will be determined in large part by the material from which thermoplastic membrane 344 is made. Membrane 344 may be an elastic material or an inelastic material. Thermoplastic membrane 344 may be applied to tubular braid element 342 by, for example, sliding a tubular membrane over element 342 or by coating tubular braid element 342 (or such other tool as may be used) with a thermoplastic liquid material. In the latter case may be desired or necessary to use one or more separation layers between tubular braid element 342 and thermoplastic membrane 344.

Anastomotic Medical Devices

This aspect of the invention relates to a device/implant, which is particularly useful for bypassing, joining or re-joining pieces of tissue in the body. Further, this aspect of the invention relates to a means for bypassing or re-joining tubular structures within the body. The system is applicable for performing an anastomosis between a vascular graft and the ascending aorta in coronary artery bypass surgery, particularly in port-access CABG surgery. Alternatively it may be used to bypass any diseased vessel (vascular or other vessel/lumen in the body. A first configuration has two parts: an anchor member, forming the attachment with the target vessel wall and a coupling member forming the attachment with the bypass graft vessel. Inserting the coupling member, with the graft vessel attached, into vessel, completes the anastomosis. A second feature of the invention includes an anastomotic fitting, having an expandable flange, which the vessel is attached which contacts the exterior surface of the target vessel. A tailored amount of pressure is applied by an expandable mechanism that then grips the target vessel wall and creates a leak-proof seal between the anastomotic mechanism and the target vessel. A third feature of the invention has a flange to which the vessel attaches, by attaching hooks that are incorporated in the expandable anastomotic device to attach to the wall of the target vessel to form the anastomosis. A method for sealing or joining a graft vessel to a target vessel at an anastomosis site, the target vessel having an opening formed therein. The method includes positioning a fastener made from a deformable material radially adjacent to a free end portion of the graft vessel. The material is transformable between a smaller and then larger size, upon application of energy to the material. The method further includes inserting at least the free end portion of the device in the target vessel through the opening in the target vessel. The free end portion of the device is radially expanded to expand the device into intimate contact with an inner wall of the target vessel. The methods and devices represented above have been at least generally represented in the attached drawings for the instant inventions.

Another aspect of the invention is particularly adapted to the anastomotic repair of hollow conduits within the body. For example if a tubular conduit in the body is partially, generally, relatively or completely blocked, diseased, restricted, etc. and the preferred solution is removal of the diseased conduit and subsequent anastomotic repair or perhaps anastomotic repair via a bypass where the instant inventions could be used for joining, re-joining or bypass of the suspect part of the conduit.

In the case where diseased conduits are removed and it is preferred that the conduit be re-joined or even replaced with other autogenous or synthetic conduit (or a combination thereof), the instant embodiments would allow the physician to insert a radially expanding tubular structure within (or over) the remaining ends of the conduit in the body. It is likely that the radially expanding tubular structure would be placed into the vessel in a condition where it is not fully expanded or in a partially radially contracted condition (or at least a somewhat radially contracted condition; although this is not a condition for the instant inventions). However, in this case, the device would be placed into both ends of the vessel (with perhaps pulling the vessels toward one another) in a condition at least equal to or less than the inside diameter of the vessel, but more likely in a somewhat slightly contracted condition. Both ends of the device may have hooks or other fasteners or even other connection areas where the device may (or may not) be attached to the visceral conduits. Additionally tissue glues commonly available today are likely to be used and may in fact be incorporated into the procedures taught herein. This may be aided with mechanical, chemical or other means or no connection at all may be required. In the case where some connection mechanism is used/required, those mechanisms may include, but are not limited to hooks, sutures, staples, adhesives, mechanical interlocking, friction, compression, etc.

This instant invention may be enhanced by the use of a tubular mesh weave or braid that has been weaved of individual yarns. The use of such a braid is common both in industry as well as medical device/implants. See, for example, U.S. Pat. Nos. 6,179,860; 6,221,006; 6,635,068; 6,258,115 and 6,450,989.

One particular advantage of this tubular mesh braid discussed in the preceding paragraph is its ability to contract and expand in a tubular fashion. The description of the tubular braid element and coatings of it are included below in this disclosure. (The coating discussed in the preceding sentence as well as below may or may not be required.) Further, instead of or in addition to the 'coating', the braid could be accomplished with multiple (18-144 or even more or less) 'yarns' so that some of the yarns could be designed such that they could act as the coating, so that it is not a coating at all, but is part of the actual braided mesh itself.

This contraction/expansion phenomenon of the tubular braid element may be useful in the instant embodiment. For example, a particular length of the braid could be formed of a particular diameter. The braid could be stretched or elongated by putting it into a somewhat tensile condition. This would allow the braid diameter to contract and hence fit easily within the tubular conduit(s) of the body. Then the braid could be allowed to relax and the diameter would expand radially to a pre-determined diameter or to the inside diameter of the visceral conduit. Conversely, the braid could be fabricated a particular diameter smaller than the visceral conduit and then put into compression to expand it radially to the appropriate diameter to join or re-join the visceral conduit. This compression or tension could then be permanently controlled if so desired by keeping the braid in an expanded condition for an appropriate period of time. Certainly this could be controlled with the use of 'memory' of the braid as is described below in the discussion of the tubular braid element and elsewhere. Alternatively the braid could be kept in an elongated/smaller diameter or a shortened/larger diameter by mechanical attachment that keeps the braid in the preferred condition.

This tubular mesh braid could be composed of many different materials used now in the medical device industry as well as newer yet to be released or discovered materials including, but certainly not limited to polymers such as PET's, Silicones, Nylons, Polyesters, Mylar, etc. metals and metal alloys such as Stainless Steels, Elgiloys, NiTli's (Nickel Titanium alloys, both TWSM (Two Way Shaped Memory) and Super Elastic NiTi's), etc.

Additionally, these radially expanded devices and methods could be accomplished with a 'slit tubular' structure commonly referred to as a Malecot structure that can be easily expanded and contracted by putting the tube in compression or extension respectively.

Even further, these radially dilating mechanisms can be accomplished by curling material like a 'cinnamon roll' such that in its smaller/contracted condition, the walls of the material would be contracted and touch one another (as with a cinnamon roll) and in its larger diameter state the walls may not be in contact with one another. This cinnamon roll can be accomplished by 'rolling' the sheet (with porosity, holes, coverings, films, membranes, drugs, compounds, etc.) of material into a tube/cylindrical like condition in a small diameter and then when in the desired location, the rolled sheet is allowed to or effected to at least partially 'unroll' into at least a partially tubular structure desired.

Even further yet, the instant inventions and methods can be accomplished by a system of a sheet of material that is longer than it is wide (e.g. like a ribbon). The longer dimension is then programmed to a tubular configuration by 'wrapping' it around a small cylindrical mandril (or other means) and treating it to keep in that small tubular configuration. Then when in the desired location, the smaller tube can be activated to become a larger tubular configuration. One such way to accomplish this is with TWSM NiTi mentioned above and disclosed as a Multi-Porous Stent in U.S. Pat. No. 6,258,115.

In all instances these mechanisms may be covered with a film of elastic or inelastic material. Further this film may be incorporated into the mechanisms as opposed to covering them. Such films, coverings or other incorporated materials may be, but are not limited to the following: silicone, nylons, polyethylenes, wovens, hybrids, PET's, woven metals, PTFE'S, Expandable PTFE's, FEP's, Teflon's, and a variety of bioabsorbable materials such as hydromers, collagens, polymers, vicryls, autogenous substances (animal, human or plant).

There may be a support wire(s) that may extend through or alongside the expandable channel devices at its distal and proximal ends (or near them). These wires may be used to help deploy or undeploy the radially expanding elements. Further, these wire(s) may be used to help keep the preferred condition when in the preferred position in the host. The support wire(s) may be one, two, three, four or more in number and may be located inside or outside the tubular structure. They may be used to put the mechanism into a tensile or compressive condition that will allow it to become a small diameter or larger diameter condition. These wires can be made permanently attachable to keep the desired configuration by attaching them permanently to keep the mechanism in the desired shape. The distal end of the core is attached to the distal end of the annular braided element (or other mechanism described herein) and the distal end of the shell is attached to the proximal end of the annular braided element. Thus movement of the core and shell relative to one another moves the braided element from a radially retracted position, which is useful for insertion into the body in a small condition to a radially expanded position, which expands it to the sidewall of the channel in the body.

A device made according to this aspect of the invention is used for intervention into the tubular channels (arteries, veins, biliary tract, urological tract, gastro-intestinal tract, stents, grafts, sinuses, nasopharynx, heart, ears, etc.) or hollow cavities (stomach, gall bladder, urinary bladder, peritoneum, etc.) of the body. Additionally the instant invention may be used in solid or semi-solid tissue including, but not limited to breast, liver, brain, pancreas, lungs etc. It is particularly convenient to use in an operating room, surgical suite, interventional suite, Emergency Room, patient's bedside, etc. environment. One preferred embodiment of this device is that the flexible shaft is inserted into the tissue, tubular channel or hollow cavity of the body usually through percutaneous access or via a surgical incision. In the case of lumens that enter and exit the body naturally, the device may enter through one of those entry or exit paths (i.e. rectal opening, mouth, ear, etc.).

Additionally, other techniques may be used for removal assistance such as the use of lytic agents, laser energy, dissolving agents, hydraulic assistance, mechanical agitation, vibration, ultrasonic energy or any other variety of assistance that will aid in the removal. Image intensification (Ultrasound, fluoroscopy, MRI, etc.) may be used as well to help with assuring the technique/removal is successful. Additionally, direct visualization using cameras or endoscopes may be used as well.

Further, materials disclosed could be of some hybrid elastic/inelastic material or compliant material. Even further, the balloon may be aided with some other mechanical substructure that aids in the outward radial force that is created by the balloon. Further when balloons are used, filaments such as thin strips of polymers such as Mylar, pet, polyethylene, etc., could be used to create a desired effect when inflating the balloon (such as shape). All of these configurations may or may not have a roughened texture on the exterior surface that will aid in the removal of the obstruction or adherence to tissue. Alternatively, all of the above mentioned configurations could have a separate or additional material applied over the expandable mechanism that is a membrane, which may or may not be roughened. The roughened surface on the expandable mechanism is easily accomplished in the manufacturing environment. One such way is to create bubbles in a liquid slurry of the polymer prior to its solid curing. Another might be the addition of dissolvable crystals to the surface of the liquid polymer prior to its cure. These dissolvable crystals could then be removed (washed off) after curing of the polymer.

Another configuration that could be used for the expandable mechanism is a mechanism(s) known as a malecot. This malecot is a common configuration used in catheters for holding them in place (in the case of feeding tubes in the intestines or stomach). It is usually a polymeric tube that has more than one, but usually two or more slits symmetrically opposed. When the distal tip of the malecot is put into compression (usually by pulling an inner wire or mandril or tube), the sides of the polymer are pushed outward to create a larger diameter on the distal tip. This larger diameter is larger than the body/shaft of the device. In the case of a malecot type configuration (as with the inflatable mechanism(s) mentioned above), the surface of the malecot could be roughened or a separate membrane (attached or not) could be put over or under the malecot so that it is roughened or strengthened. Further, a membrane that connects the ribs or wings of a malecot is easily fabricated to increase the surface area of the malecot ribs or wings alone.

Yet, another alternative design of the expandable mechanism is one that has similarities to the malecot, but uses a multi-stranded braid on the distal end. When the braid is put into compression, the braid is pulled together and it flares out to create a larger diameter on the distal end. Changing the pore size along the braid so that the holes in the braid go from none to large holes/pores easily modifies the braid. This can be accomplished by braiding the braid with metals and polymers and melting the polymers away or by simply braiding at different rates while braiding that causes different pore sizes also known in the braiding industry as pics per inch. This is easily accomplished 'on the fly' while braiding by using a programmable braider. The braid pics per inch change with time as the tubular mesh braid is being braided. This varying pore size may have a number of advantages to the current invention. It could aid with stopping porosity when needed and allowing porosity when you need it. For example, it is possible that ingrowth would be desired in contact with tubular body structures at certain times and that there be no porosity when trying to achieve a leak free environment (perhaps in between the two tubular structures being attached or when bypassing.

Alternatively, either the braid or the malecot can have a permanent set put into in so that it is normally open with the larger diameter. In this case, when it is put into tension (usually from some inner (or outer) core wire or mandril), it collapses down to the diameter of the shaft of the device.

Alternatively, too much abrasive action on the surface of the mechanism(s) may be deleterious to the patient as well. In the case of the braided configuration, some smoothener may be required so that just the appropriate amount of friction is realized for effective obstruction removal. Further, the realized rigidity of any of the type of mechanism(s)s must be optimized for this removal in the particular application.

A radially collapsible tubular channel can also be fabricated from several materials and configurations. One preferred configuration is a multi-stranded braided device. The strands can be made of any material that would be useful for a particular application (polymers like polyester, nylon, Mylar, etc.) or, metal (stainless steel, Nickel Titanium Allow (Nitinol), platinum, etc.). Certainly, the potentially useful materials are not constrained to those materials listed. Additionally, the mechanism channel may be coated or encased in an elastomeric or other covering. Further, the mechanism channel may be fabricated of a material that will enlarge due to different forces than that of the braid mentioned previously. One other such force derived mechanism could be a material that swells/enlarges when put into a moist environment. Another such force derived mechanism is one that swells/enlarges when thermal energy is applied such as Two Way Shaped Memory Alloy (TWSMA) such as a Nickel-Titanium alloy. Yet, another may be one that occurs from an electrical, magnetic or other mechanical configuration/design/force.

The Tubular Braid Elements

The mechanisms described above include an elongate tube; an elongate mandril inside the tube and an expandable tubular braid. The elongate mandril extends from the proximal end of the device to the distal end. The elongate tube usually extends from close to the proximal end of the device to close to the distal end. The distal end of the tubular braid is bonded to the distal end of the inner elongate mandril. The mandril may extend beyond the tubular braid. The proximal end of the tubular braid is bonded to the distal end of the elongate tube.

The braid may be open, but may be laminated or covered with a coating of elastic, generally inelastic, plastic or plastically deformable material, such as silicone rubber, latex, polyethylene, thermoplastic elastomers (such as C-Flex, commercially available from Consolidated Polymer Technology), polyurethane and the like. The assembly of tube, mandril and braid is introduced percutaneously in its radially compressed state. In this state, the outside diameter of the braid is close to the outside diameter of the elongate tube. This diameter is in the range of 10 to 500 mils, and usually 25 to 250 mils (i.e. thousandth of an inch) (0.25 to 12.7 mm, usually 0.64 to 6.4 mm). After insertion, moving the mandril proximally with respect to the tube expands the tubular braid.

The tubular braid is preferably formed as a mesh of individual non-elastic filaments (called "yarns" in the braiding industry). However, it can have some elastic filaments interwoven to create certain characteristics. The non-elastic yarns can be materials such as polyester, PET, polypropylene, polyamide fiber (Kevlar, Dupont), composite filament wound polymer, extruded polymer tubing (such as Nylon II or Ultem, commercially available from General Electric), stainless steel, Nickel Titanium (Nitinol), or the like so that axial shortening causes radial expansion of the braid. These materials have sufficient strength so that the tubular braided element will retain its expanded condition in the lumen of the body while removing the matter therefrom. Further, all expandable mechanisms described heretofore, can be manufactured using shape memory materials so that they are self expanding or even expandable when certain temperatures or thermal energies are delivered to the mechanisms. Such material characteristics can be accomplished with different programming methods such as, but not limited to Two Way Shape Memory (TWSM) alloys.

The braid may be of conventional construction, comprising round filaments, flat or ribbon filaments, square filaments, or the like. Non-round filaments may be advantageous to decrease the axial force required for expansion to create a preferred surface area configuration or to decrease the wall thickness of the tubular braid. The filament width or diameter will typically be from about 0.5 to 50 mils (0.013 to 1.3 mm), usually being from about 5 to 20 mils (0.13 to 0.51 mm). Suitable braids are commercially available from a variety of commercial suppliers.

The tubular braids are typically formed by a "Maypole" dance of yarn carriers. The braid consists of two systems of yarns alternately passing over and under each other causing a zigzag pattern on the surface. One system of yarns moves helically clockwise with respect to the fabric axis while the other moves helically counter-clockwise. The resulting fabric is a tubular braid. Common applications of tubular braids are lacings, electrical cable covers (i.e. insulation and shielding), "Chinese hand-cuffs" and reinforcements for composites. To form a balanced, torque-free fabric (tubular braid), the structure must contain the same number of yarns in each helical direction. The tubular braid may also be pressed flat to form a double thickness fabric strip. The braid weave used in the tubular braid of the present invention will preferably be of the construction known as "two dimensional, tubular, diamond braid" that has a 1/1 intersection pattern of the yarns which is referred to as the "intersection repeat". Alternatively, a Regular braid with a 2/2-intersection repeat and a Hercules braid with an intersection repeat of 3/3 may be used. In all instances, the helix angle (that being the angle between the axis of the tubular braid and the yarn) will increase as the braid is expanded. Even further, Longitudinal Lay-Ins can be added within the braid yarns and parallel to the axis to aid with stability, improve tensile and compressive properties and modulus of the fabric. When these longitudinal "Lay-In" yarns are elastic in nature, the tubular braid is known as an elastic braid. When the longitudinal yarns are stiff, the fabric is called a rigid braid. Biaxially braided fabrics such as those of the present invention are not dimensionally stable. This is why the braid can be placed into an expanded state from a relaxed state (in the case of putting it into the compressive mode). Alternatively this could be a decreased/reduced (braid diameter decreases) state when put into tension from the relaxed state. When put into tension (or compression for that matter) the braid eventually reaches a state wherein the diameter will decrease no more. This is called the "Jammed State". On a stress strain curve, this corresponds to increase modulus. Much of the engineering analyses concerning braids are calculated using the "Jammed State" of the structure/braid. These calculations help one skilled in the art to design a braid with particular desired characteristics. Further, material characteristics are tensile strength, stiffness and Young's modulus. In most instances, varying the material characteristics will vary the force with which the expanded condition of the tubular can exert radially. Even further, the friction between the individual yarns has an effect on the force required to compress and un-compress the tubular braid. For the present invention, friction should be relatively low for a chosen yarn so that the user will have little trouble deploying the engaging element. This is particularly important when the engaging element is located a significant distance from the user. Such is the case when the percutaneous entry is the groin (Femoral Artery for vascular interventions) and the point of engaging the engaging element is some distance away (i.e. the Carotid Artery in the neck). Similarly, this is true for long distances that are not vascular or percutaneous applications.

Coating of the Tubular Braid

Throughout this disclosure, it is mentioned that the tubular braid may be coated with a material so that it may have no porosity or variable porosity within the individual filaments of the braid. This is an important configuration of the present invention and in certain instances may be critical (i.e. when a cancer is being removed from a small puncture hole, cancerous tissue must not be able to leak out through the walls of the tubular braid because the cancer may be seeded along the tract. This is important in the case of laparoscopic surgery as well. In fact, it may be important in many instances, not only where cancer is apparent.) One simple way to cover the tubular braid is to attach tubing over it. This has been done to prototypes of the present invention and works quite well. Elastomeric and inelastic coverings have been used. In some instances thermoplastic coverings were used and then heat and compression was applied along the tubular braid to melt it into the braid filaments. This works well. The braid was expanded from its original small diameter by sliding a mandril into the tubular braid. Once the braid is expanded, a liquid thermoset elastomer including, but not limited to silicone rubber, latex rubber, etc. or thermoplastic material including, but not limited to polyurethane was coated via a spray, dip, brush or other method. When the material cured, the mandril was removed and the tubular braid could be pulled on both ends (put into compression) and the tubular braid would go back to its original diameter. This is important for several reasons; the method described here allows the material to be applied within the filaments instead of over the filaments. This decreases the overall diameter of the tubular braid significantly as opposed to putting a covering over it. Further, the integrity of the material in between the filaments as opposed to over the filaments is increased because as the expandable channel is pushed forward, the material is hidden within the braid and hence doesn't see the forces of the tissue against it. Using a covering over the braid, the forces during the pushing are directly transmitted to the covering over the braid. Even further, the reliability and cost to manufacture are greatly improved. Even further and of extreme import is the fact that using a liquid that cures or a thermoplastic covering that is melted into the braid as opposed to covering it allows for varying the porosity along the tubular braid. This is extremely important in those cases where variable porosity is desired.

Device Testing

Prototypes of the mechanisms were fabricated from the materials disclosed heretofore and of the dimensions commensurate with this disclosure.

Further, several different types of tubular braid were coated and/or covered with polymer elastomers and inelastomers as described heretofore. In one case, the braid was expanded to some diameter greater than the relaxed and smaller diameter. This was accomplished using a Teflon mandril. With the tubular braid in this somewhat expanded condition, the assembly was coated with liquid silicone rubber. When it dried, putting the system into tension so that the smaller original diameter was achieved again could elongate the assembly. It could then be put into compression and thusly shortened so that it would expand and the braid was covered so that there could be no holes in between the filaments of the braid. Further, the overall diameter of the tubular braid as not increased except for maybe 0.0001" (0.0025 mm). Even further, trap devices were made whereby the silicone rubber was sprayed or painted onto the tubular braid when it was in the deployed/expanded condition. Once dried, the assembly could be un-deployed and then re-deployed with ease and without any holes between the filaments. Lastly, tubular braids were coated as described above with only partial coating to create variable porosity along the braid. Even further, the totally coated tubular braid was easy to puncture so that variable porosity was achieved as well. Further, multi-stranded braided tubing was braided using over 100 individual yarns made of thermoplastic materials and metallic materials. After braiding was completed, individual yarns were removed to change porosity. Alternatively when a combination of metal and thermoplastic yarns were used, the thermoplastic yarns were heated and melted away from the tubular mesh to change the pore size by leaving the metal or polymers with higher melt temperatures (or in the case of thermoset polymers, higher temperature resistant materials) leaving the metal or higher temperature resistant materials in place.

An exemplary device has the following characteristics:
Working Length
10-500 cm
Working Diameter The expandable mechanism has an outer diameter that ranges from 0.006" to 0.450" (0.15 mm to 1.14 cm), but can extend to smaller and larger sizes as technology and procedures require. The expandable mechanisms of the instant invention would be small in its un-deployed state in the range of 0.020-0.090 inches (0.51 mm to 2.3 mm) but would be expandable to diameters of with a tenfold increase or even larger.

Physical Configuration

The device of the instant invention may have conventional lubricious coatings to enhance introduction into the target body lumen, e.g. hyaluronic or other equivalent coatings. Further, the technician may apply a lubricious coating just before surgery. Also, a variety of drugs may be used with the device, as well as the above-described devices, for a variety of reasons such as reducing infection and/or rejection, and in the case of vascular situations, drug eluting mechanism can be added to help prevent stenosis or restenosis. Such drugs or compounds may be but are not limited to Sirolimus—a immunosuppressant drug usually used to prevent rejection in organ transplants—elutes from the stent into the vessel wall over the period when the scar tissue may be growing. Paclitaxel, a chemotherapy drug, may also be used. The Paclitaxel may gradually release directly into the coronary artery wall to prevent the restenosis process; this may be accomplished by embedding the material in the polymer as opposed to coating the device. The same may be true for Sirolimus.

As an advantage of the instant invention, the device will be less difficult to feed it to the desired location in the body due to its decreased size. Another advantage of the instant invention would be the ease with which bypassing or anastomosis can be accomplished. It can be done in a percutaneous fashion as opposed to an open, surgical procedure as well. Over the past decades, it has been proven that percutaneous intervention as compared to open surgical intervention has shown a great decrease in morbidity and mortality as well. This decreased difficulty will decrease cost due to time in the Operating Room (Operating Rooms costs are estimated in excess of $90 dollars per minute in the U.S.)

Figure 63:
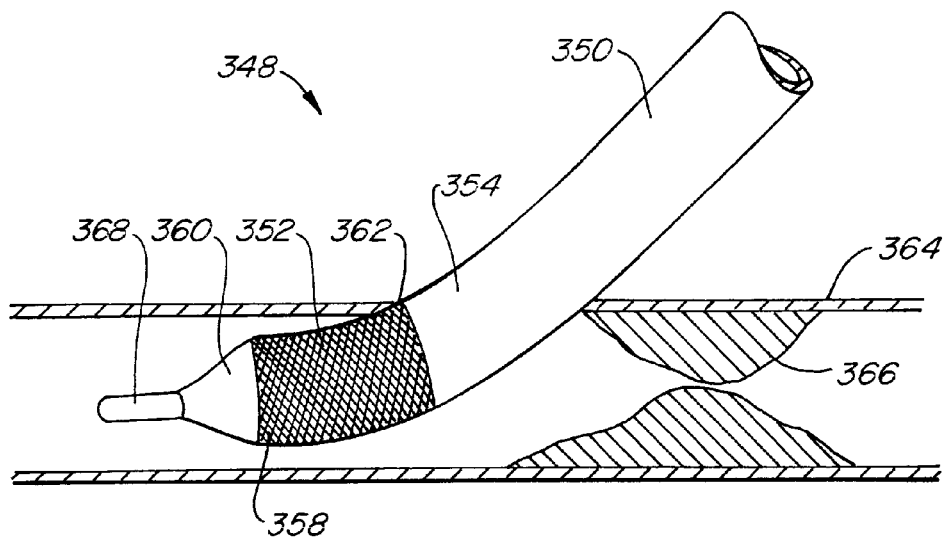
FIG. 63 shows a first end of anastomotic medical device placed within a tubular structure.
Figure 64:
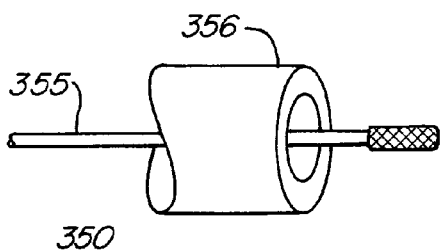
FIGS. 64 and 65 show the second end of the tube of the device of FIG. 63 with an actuator pulled proximally in FIG. 65 so to expand the tubular braided anchor member of FIG. 63.
Figure 65:
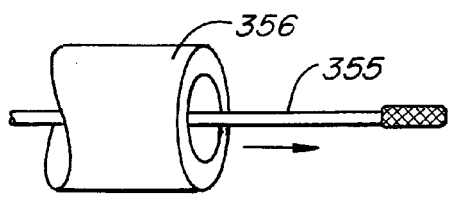
Figure 66:
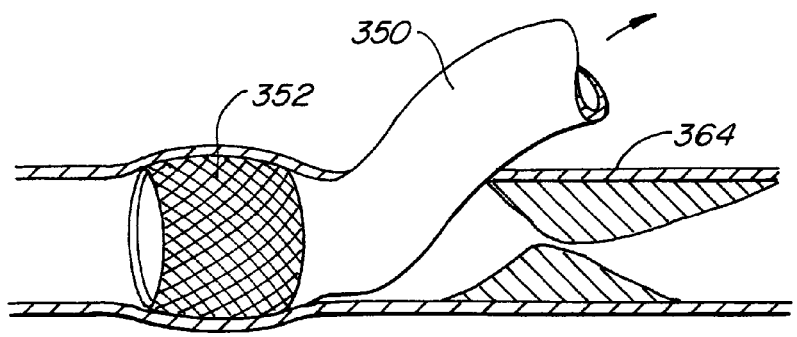
FIG. 66 shows the device of FIG. 63 with the tubular braid anchor member in a radially expanded state and the dilator and guide wire removed.
Figure 67:
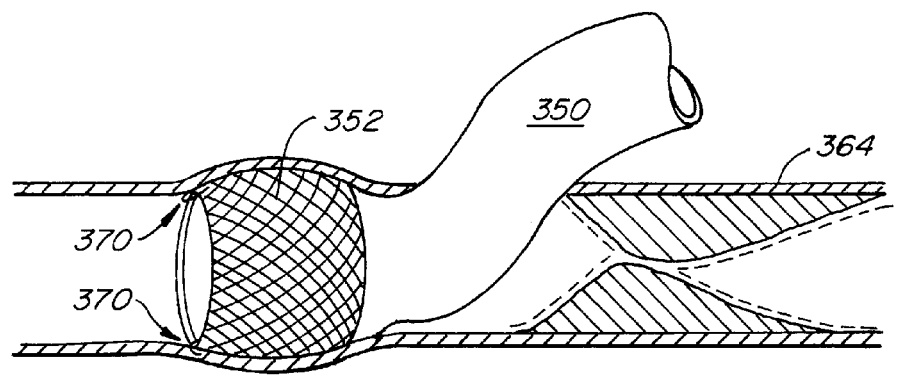
FIG. 67 is similar to FIG. 66 but shows the use of hooks to help secure the tubular braid anchor member to the tubular structure.

FIG. 63 illustrates the distal end of an anastomotic medical device 348 including a tube 350 having a tubular braid anchor member 352 secured to a first end 354 thereof. Device 348 also includes an actuator 355 extending through tube 350 past the second end 356 of tube 350, see FIGS. 64 and 65, and connected to the distal end 358 of anchor member 352. A dilator 360 passes through tube 350 and helps to guide medical device 348 through a relatively small opening 362 in tubular structure 364 of a patient. FIG. 63 illustrates device 348 passing into a blood vessel near the diseased obstruction 366. Finally, device 348 includes a guide wire 368 passing centrally through dilator 360. After being properly positioned, dilator 360 and guide wire 368 are removed and actuator 355 is pulled, as indicated in FIG. 65, to cause anchor member 352 to expand as shown in FIG. 66. If desired, anchor member 352 could be self expanding or expandable on the application of, for example, heat. FIG. 67 illustrates anchor member 352 including hooks 370 deployed to help secure anchor member 352 in place. Hooks 370 can be deployed by first pushing them distally and pulling them proximally to lock/hook tubular structure 364 or by axially contracting anchor member 352 to expose the hooks. Note that while tubular structure 364 is shown to be radially expanded when anchor member 352 is secured in place, such distention of the tubular structure may not be required.

Figure 68:
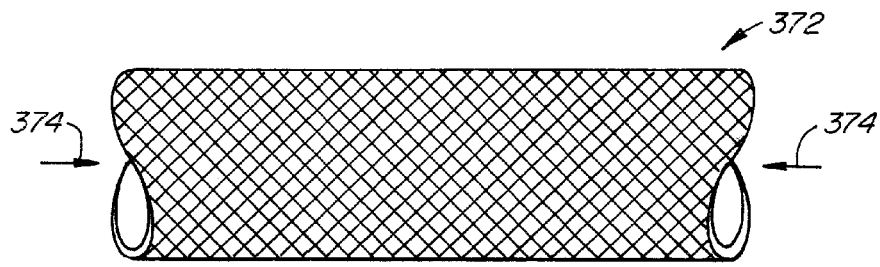
FIGS. 68 and 69 show a tubular mesh braid in axially compressed and axially expanded states.
Figure 69:
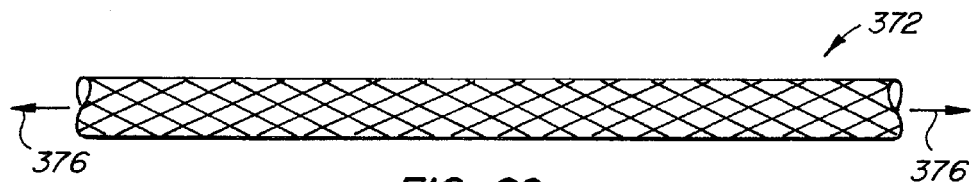
Figure 70:
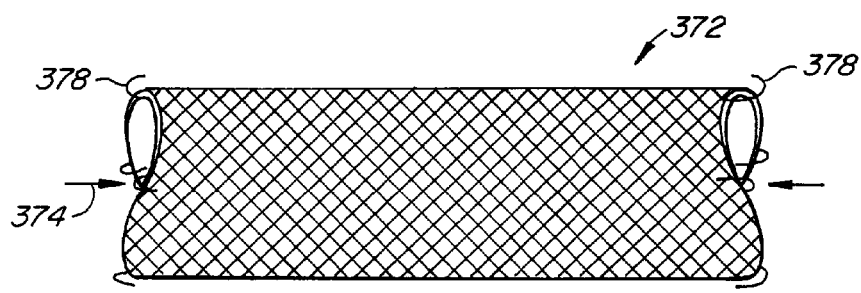
FIG. 70 is similar to FIG. 68 but shows the use of hooks to help secure the tubular mesh braid to a vessel wall.

An example of tubular mesh braid 372 is shown in FIGS. 68 and 69. Braid 372 can easily changed diameter by 1000% due to compression/tension forces as illustrated by arrows 374, 376 or due to a permanent set put into braid 372 during manufacturing. Alternatively, temperature change, or electrical, mechanical or magnetic forces, could be used to create the change in diameter as desired. FIG. 70 illustrates tubular mesh braid 372 including hooks 378. Hooks 378 can be deployed due to foreshortening of braid 372. This foreshortening may occur with other expandable mechanisms disclosed above so that hook deployment can be accomplished using such other expandable mechanisms.

Anastomotic medical device 348 may have second end 356 positioned externally of a patient's body and provide access to a single tubular structure. However, two anastomotic medical device 340 may be used in a patient and connected to two different tubular structures within a patient or may be used to bypass a portion of the same tubular structure. In either case, the second ends 256 of the two anastomotic medical devices 348 are secured to one another in an appropriate fashion. The following FIGS. 71-74 show various structures for joining the ends of a tubular structure of a patient; the structure may also be used to join second ends 356 in appropriate cases.

Figure 71:
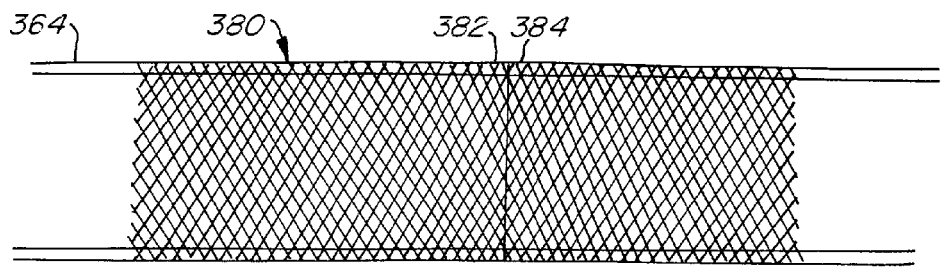
FIG. 71 illustrates a tubular braided type of anastomotic medical device covering the opposed ends of a severed tubular structure.
Figure 72:
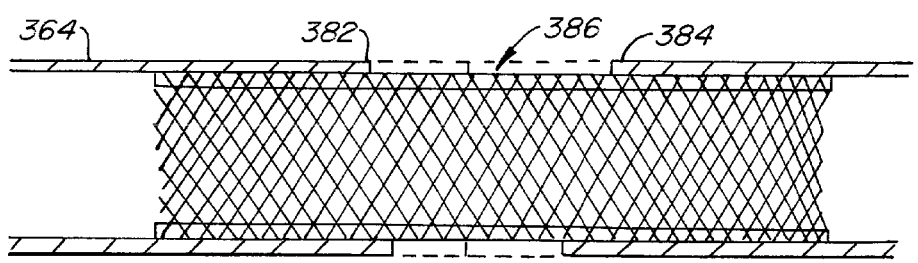
FIG. 72 illustrates an internally applied tubular braided type of anastomotic medical device used to secure the ends of a severed tubular structure.
Figure 73:
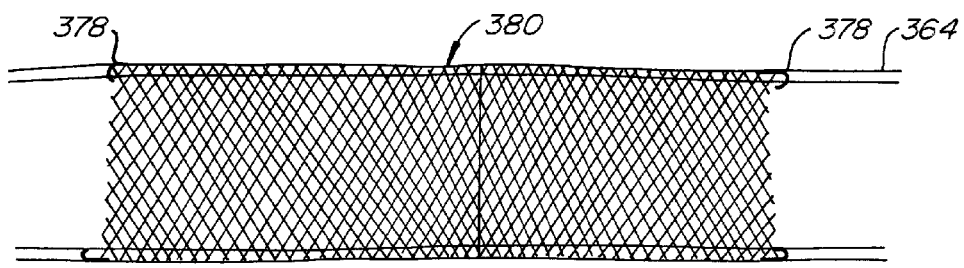
FIGS. 73 and 74 are similar to FIGS. 71 and 72 but include the use of hooks to help secure the anastomotic medical devices to the tubular structures.
Figure 74:
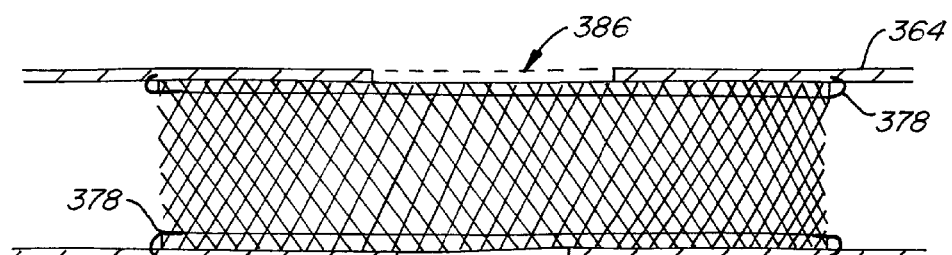

FIG. 71 illustrates a tubular braided type of anastomotic medical device 380 covering the opposed ends 382, 384 of a severed tubular structure 364. Ends 382, 384 are shown to be abutting but may be separated as well. The relaxed state of medical device 380 is a smaller diameter state so that device 380 squeezes tubular structure 364 to maintain ends 382, 384 in place. If desired, the central portion of device 380 could be made to be liquid impervious or the entire device may be liquid impervious. FIG. 72 illustrates the use of a radially outwardly expanding anastomotic medical device 386 within the interior of tubular structure 364 to join ends 382, 384. Ends 382, 384 may be spaced apart from one another or abutting, as indicated in dashed lines in FIG. 72. An appropriate portion of device 386 is typically liquid impervious to prevent leakage. If desired, a radially inwardly expanding device 380 could be used on the outside of tubular structure 364 and a radially outwardly expanding device 386 could be used on the inside of tubular structure 364 at the same junction. FIGS. 73 and 74 illustrate anastomotic medical devices 380, 386 but with the addition of hooks 378 to help secure the anastomotic medical devices in place. Various membranes, films, wovens, and coatings could be used to aid with the function of the mechanisms disclosed above. Multiple porosities may also be advantageous for different applications. Drugs and other therapeutic agents may also be used in association with the above anastomotic devices.

Figure 75:
FIGS. 75 and 76 show two different types of variable porosity anastomotic medical devices.
Figure 76:
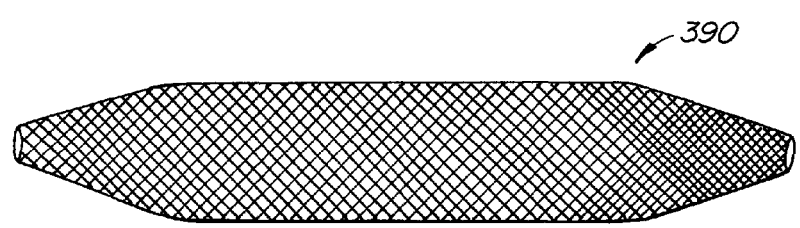

FIG. 75 illustrates a variable porosity anastomotic device 388 in the form of a straight tube. FIG. 76 illustrates a variable porosity anastomotic device 390 in the form of a tapered tube. If such structures were placed inside the body channel, it may be desired to have the smaller pores at the central portion and the larger pores at the outer ends. The materials used for the various anastomotic medical devices described above could be all non-absorbable/degradable, all absorbable/degradable or a combination of the two depending upon the particular anastomotic application.

Figure 77:
FIG. 77-80 illustrate malecot-type of anastomotic medical devices in radially expanded and radially contracted states.
Figure 78:
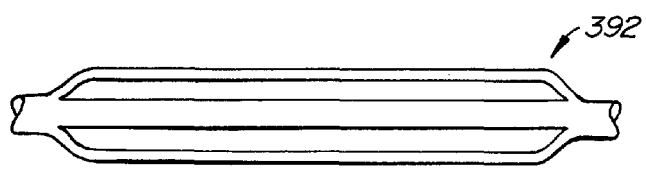
Figure 79:
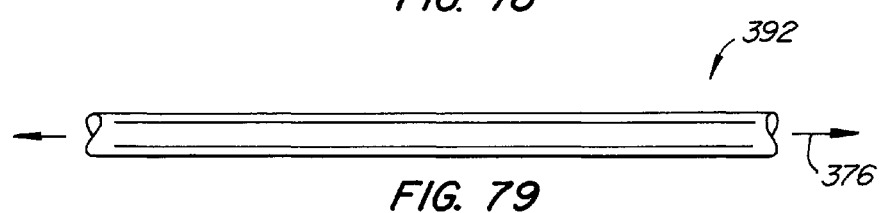
Figure 80:
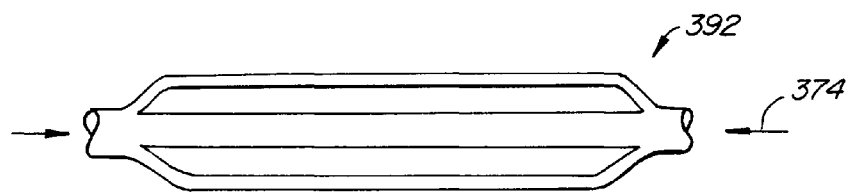
Figure 81:
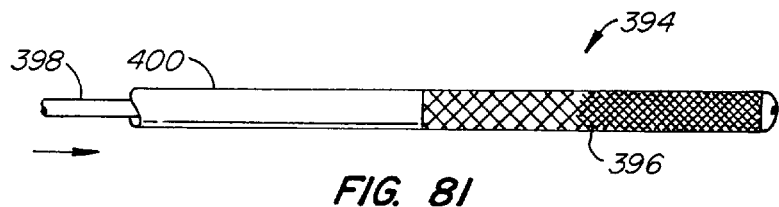
FIGS. 81 and 82 show a variable porosity expandable device in radially contracted and radially expanded states.
Figure 82:
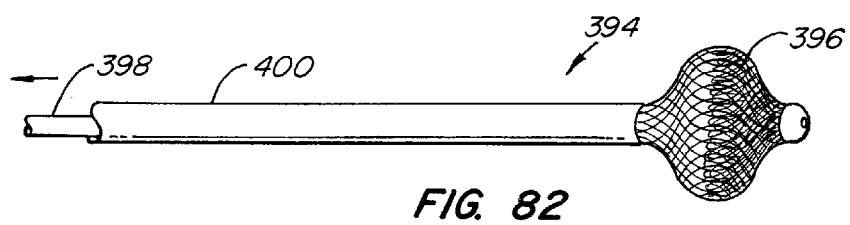

FIGS. 77 and 78 illustrate a malecot-type anastomotic device 392 and radially contracted and radially expanded states. Device 392 is shown having four slits 393, although two or more may suffice for radial expansion. FIGS. 79 and 80 illustrate the application of tension force, indicated by arrows 376, and compression force, indicated by arrows 374, to device 392 to place the device in radially contracted and radially expanded states FIGS. 81 and 80 illustrate a variable porosity expandable device 394 having a variable porosity braid 396 placeable in the radially contracted and radially expanded states of FIGS. 81 and 82 by sliding inner tube 398 within outer tube 400 as indicated by the arrows in the Figs.

Figure 83:
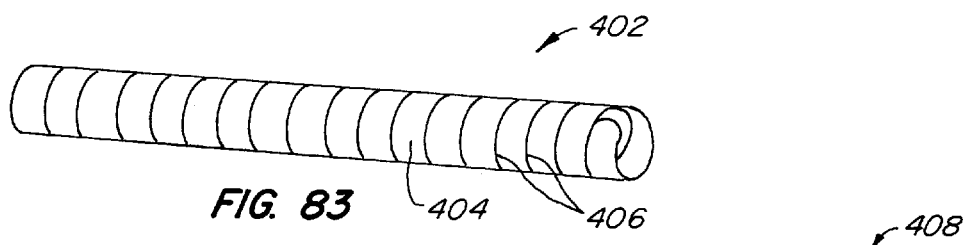
FIGS. 83 and 84 show a spiral ribbon type of radially expandable and contractible device in radially contracted and radially expanded states.
Figure 84:
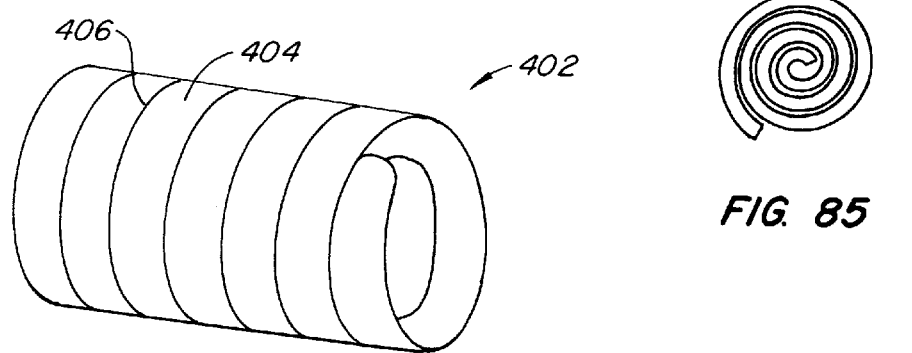
Figure 85:
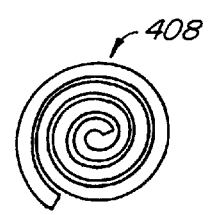
FIG. 85 is an end view of a coiled cylinder type of radially expandable and radially contractible device.

FIGS. 83 and 84 illustrate a variable diameter device 402 in a radially contracted state in FIG. 83 and a radially expanded state in FIG. 84. Device 402 includes a spiral ribbon 404 of material constructed so that the lateral edges 406 of spiral ribbon 404 are generally adjacent, that is close to one another or overlapping, to provide a generally continuous cylindrical surface so to approximate a solid cylinder. FIG. 85 is an end view of a coiled cylinder 408.

Figure 86:
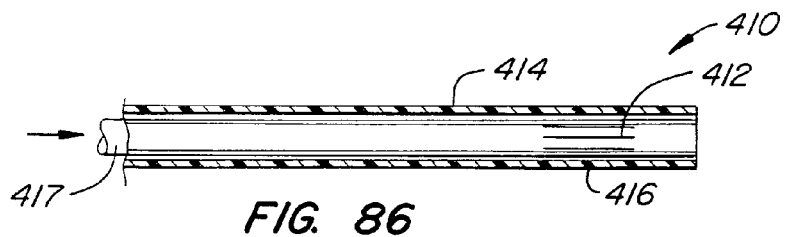
FIGS. 86-91 show different embodiments of a malecot-type of anastomotic medical device in radially expanded and radially contracted states.
Figure 87:
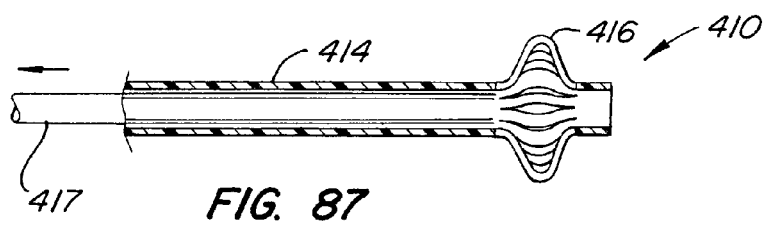
Figure 88:
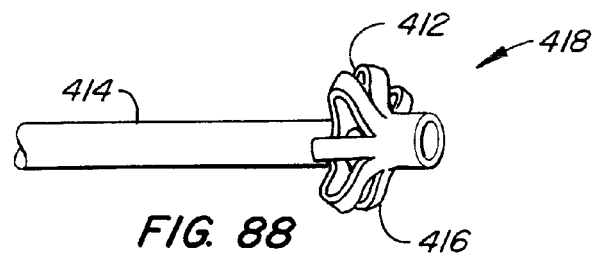
Figure 89:
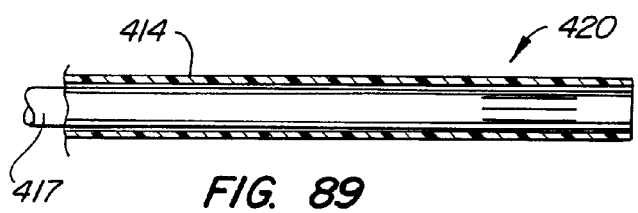
Figure 90:
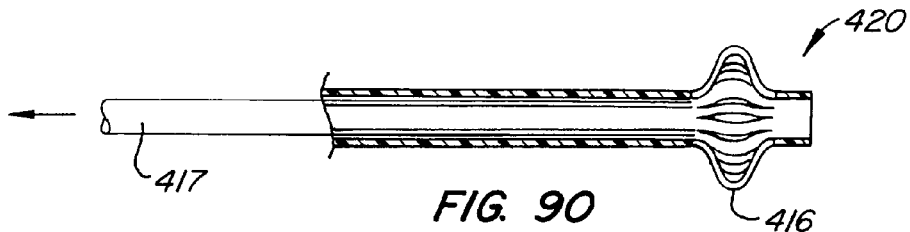
Figure 91:
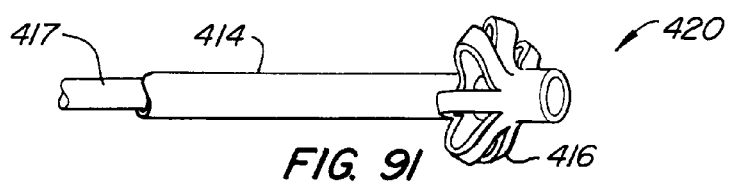

FIGS. 86-87 illustrate a self expanding, expandable channel anastomotic device 410 having two slits 412 formed in outer tube 414. The expandable end 416 of device 410 can be kept in its radially contracted state of FIG. 86 by pushing on inner tube 417, or allowed to assume its radially expanded state of FIG. 87 by permitting inner tube 417 to move in the direction of the arrow. FIG. 88 illustrates an anastomotic device 418 that naturally assumes the radially expanded state of FIG. 88 but is initially maintained in a radially contracted state by an outer tube, not shown. When expansion is desired, the outer tube is withdrawn or otherwise removed allowing expansion of expandable end 416 to occur. The anastomotic device 420 of FIGS. 89-91 is similar to the device of FIGS. 86 and 87 but naturally assumes the radially contracted state of FIG. 89. To place the device in a radially expanded state, inner tube 417 is pulled as indicated in FIG. 90. Although not illustrated, various membranes, films, etc. can be used to fill in all or part of the spaces created by slits 412 in the expandable ends 416 of the devices.

Figure 92:
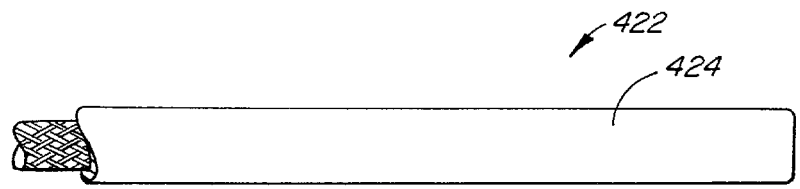
FIGS. 92 and 93 show a self expanding braided type of anastomotic medical device in a radially contracted state within an outer tube in FIG. 92 and in a radially expanded state after being extended from the outer tube in FIG. 93.
Figure 93:
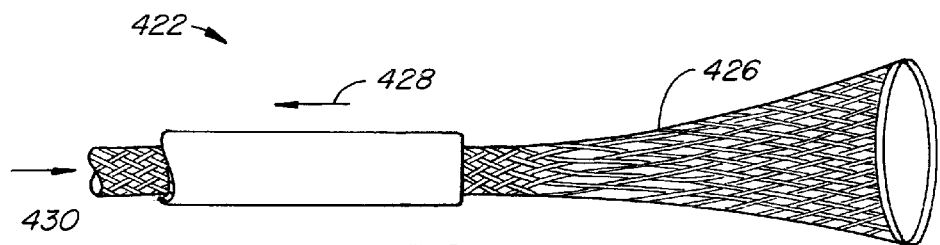

An anastomotic device 422 is shown FIGS. 92 and 93 to include an outer tube 424 and an inner, self expanding braided member 426. Braided member 426 is initially constrained by outer tube 424 that may be flexible and/or lubricated. Braided member 426 may be permitted to expand by sliding outer tube 424 in a retrograde fashion in the direction of arrow 428 or by pushing braided member 426 in the direction of arrow 430, or both. Other types of structures, including a malecot such as shown FIGS. 86 and 87, a coiled tubular device such as shown in FIGS. 83 and 84, or a coiled cylinder device such as shown in FIG. 85, could be mechanized in such a fashion.

Figure 94:
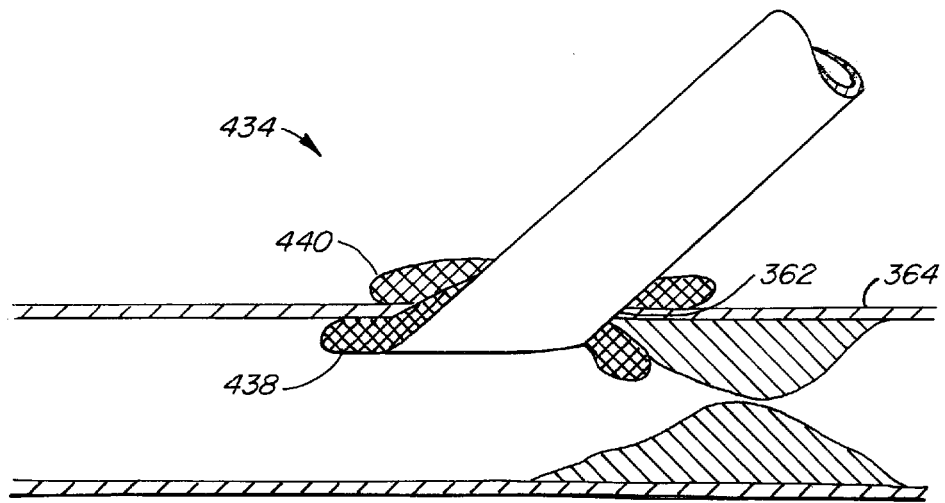
FIG. 94 illustrates an alternative to the tubular braid anchor member of FIG. 63 in which one or two radially expandable mechanisms are used to engage the periphery of the opening in the tubular structure.

FIG. 94 illustrates an alternative to the tubular braid anchor member 352 of FIGS. 63 and 66. Anastomotic device 434 includes a tube 436 having an inner expandable mechanism 438 or both an inner expandable mechanism 438 and an outer expandable mechanism 440 used to engage the periphery of opening 362 in tubular structure 364. Expandable mechanisms 438, 440 may be tubular mesh braid as shown or some other type of expandable device, such as an inflatable balloon, a malecot, a coiled tubular device or coiled cylindrical device.

Figure 95:
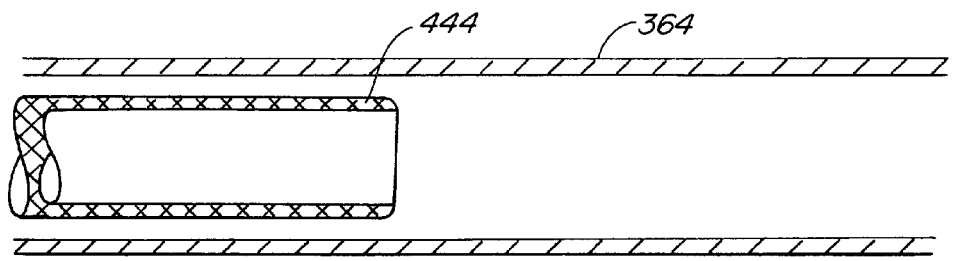
FIGS. 95-97 illustrate a tubular mesh braid at the distal end of an endo device at different states within a tubular structure.
Figure 96:
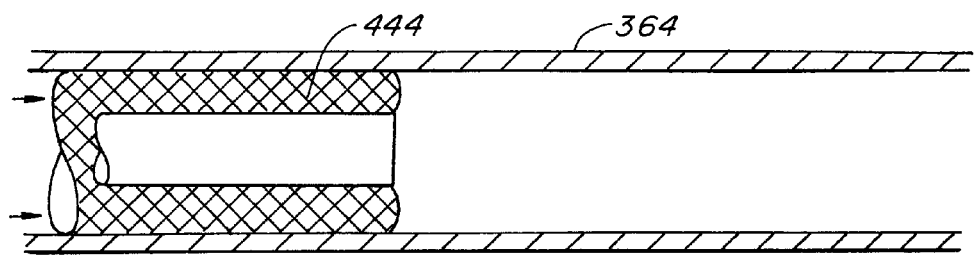
Figure 97:
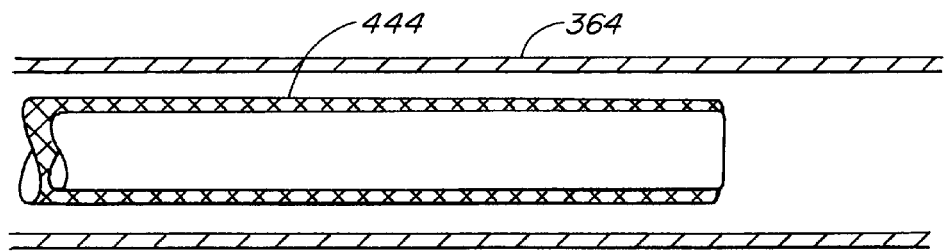

FIG. 95 illustrates a tubular mesh braid 444 mounted to the exterior of, for example, an endoscope or other elongate device within a tubular structure 364, for example the bowl or intestine. FIG. 96 illustrates braid 444 in an expanded state as result of pushing on the braid as indicated by the arrows. Advancing the endo device causes tubular braid 444 to contract down back on the endo device as shown in FIG. 97.

Other modification and variation can be made to the disclosed embodiments without departing from the subject of the invention as defined in following claims.

Any and all patents, patent applications and printed publications referred to above are incorporated by reference.

The invention claimed is:

1. A vessel-occluding and occlusion removal medical device for removing blockages in blood vessels for the treatment of cardiovascular disease in the human body, the device comprising:

an outer tube having a proximal end, a distal tip and a lumen extending from the distal tip towards the proximal end;

an inner tube within the lumen, the inner tube having a proximal end and a distal end, the inner and outer tubes movable between a first position, with the distal end positioned distally a first distance from the distal tip, towards one another to a second position, with the distal tip and distal end separated by a second distance, the second distance being shorter than the first distance; and a flexible tubular metal mesh braid sleeve having a radially contracted state and a radially expanded state, the tubular sleeve comprising multiple filaments, a first end joined to the distal tip of the outer tube, a second end joined to the distal end of the inner tube, and a coating disposed within and between the multiple filaments and covering only a first portion of the tubular sleeve, thus leaving a second portion of the tubular sleeve uncoated and porous to provide variable porosity along the tubular sleeve, the uncoated second portion comprising multiple pores between multiple filaments, wherein the tubular sleeve comprises a generally U-shaped, direction reversing region which is formed by, and which moves along the length of, the tubular sleeve when the inner and outer tubes move between the first and second positions, the direction reversing region separating the tubular sleeve into an outer portion and an inner portion and comprising a region of variable stiffness in the tubular sleeve configured to buckle more easily than the remainder of the tubular sleeve as the outer and inner tubes are moved between the first and second positions, wherein the tubular sleeve assumes the radially contracted state when the inner and outer tubes are in the first position, wherein the region of variable stiffness causes the tubular sleeve to tend to fold into the radially expanded state when the inner and outer tubes are in the second position, wherein, when the tubular sleeve is in the expanded state, the outer portion of the tubular sleeve overlies and is directly opposite the inner portion of the tubular sleeve and the tubular sleeve has a funnel shape with a conical proximal funnel portion and a cylindrical distal funnel portion having a substantially constant diameter, the distal funnel portion configured to contact and exert an outward radial force onto an inner wall of a blood vessel when the tubular sleeve is placed therein, the outward radial force being sufficient to seal the tubular sleeve against the inner wall and occlude the blood vessel, and wherein the tubular sleeve in the expanded state has a longitudinally-extending opening to permit material to pass therethrough for receipt of material into the inner tube.

2. The medical device according to claim 1, wherein the tubular metal mesh braid sleeve comprises a material selected from the group consisting of stainless steel, eligoy, nickel titanium alloy and platinum.

* * * * *